US008344121B2

(12) United States Patent
Lyakhov et al.

(10) Patent No.: US 8,344,121 B2
(45) Date of Patent: Jan. 1, 2013

(54) NANOPROBES FOR DETECTION OR MODIFICATION OF MOLECULES

(75) Inventors: Ilya G. Lyakhov, Frederick, MD (US); Thomas D. Schneider, Frederick, MD (US); Danielle Needle, Frederick, MD (US)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 1534 days.

(21) Appl. No.: 11/638,160

(22) Filed: Dec. 12, 2006

(65) Prior Publication Data
US 2010/0227913 A1    Sep. 9, 2010

Related U.S. Application Data

(60) Provisional application No. 60/749,729, filed on Dec. 12, 2005, provisional application No. 60/749,858, filed on Dec. 12, 2005.

(51) Int. Cl.
*C07H 21/04* (2006.01)
*C07H 21/02* (2006.01)
*G01N 33/48* (2006.01)
*A61K 48/00* (2006.01)
(52) U.S. Cl. .................. 536/24.31; 436/94; 514/44
(58) Field of Classification Search .................. 435/7.1, 435/7.7, 331, 344, 344.1, 345; 436/537, 436/800
See application file for complete search history.

(56) References Cited

U.S. PATENT DOCUMENTS

| | | |
|---|---|---|
| 4,711,955 A | 12/1987 | Ward et al. |
| 4,793,705 A | 12/1988 | Shera |
| 4,917,462 A | 4/1990 | Lewis et al. |
| 4,962,037 A | 10/1990 | Jett et al. |
| 5,017,009 A | 5/1991 | Schutt et al. |
| 5,047,519 A | 9/1991 | Hobbs, Jr. et al. |
| 5,064,754 A | 11/1991 | Mills |
| 5,105,305 A | 4/1992 | Betzig et al. |
| 5,124,247 A | 6/1992 | Ansorge |
| 5,151,507 A | 9/1992 | Hobbs, Jr. et al. |
| 5,221,518 A | 6/1993 | Mills |
| 5,242,796 A | 9/1993 | Prober et al. |
| 5,306,618 A | 4/1994 | Prober et al. |
| 5,332,666 A | 7/1994 | Prober et al. |
| 5,354,985 A | 10/1994 | Quate |
| 5,360,523 A | 11/1994 | Middendorf et al. |
| 5,389,779 A | 2/1995 | Betzig et al. |
| 5,405,747 A | 4/1995 | Jett et al. |
| 5,470,710 A | 11/1995 | Weiss et al. |
| 5,547,835 A | 8/1996 | Köster |
| 5,556,790 A | 9/1996 | Pettit |
| 5,614,386 A | 3/1997 | Metzker et al. |
| 5,625,048 A | 4/1997 | Tsien et al. |
| 5,654,176 A | 8/1997 | Smith |
| 5,661,028 A | 8/1997 | Foote |
| 5,674,743 A | 10/1997 | Ulmer |
| 5,707,804 A | 1/1998 | Mathies et al. |
| 5,763,594 A | 6/1998 | Hiatt et al. |
| 5,777,079 A | 7/1998 | Tsien et al. |
| 5,780,232 A | 7/1998 | Arlinghaus et al. |
| 5,800,996 A | 9/1998 | Lee et al. |
| 5,814,454 A | 9/1998 | Ju |
| 5,821,058 A | 10/1998 | Smith et al. |
| 5,866,336 A | 2/1999 | Nazarenko et al. |
| 5,886,177 A | 3/1999 | Cook et al. |
| 5,998,204 A | 12/1999 | Tsien et al. |
| 6,150,176 A | 11/2000 | Tsien et al. |
| 6,197,928 B1 | 3/2001 | Tsien et al. |
| 6,210,896 B1 | 4/2001 | Chan |
| 6,495,664 B1 | 12/2002 | Cubitt |
| 6,544,746 B2 | 4/2003 | Heyduk |
| 6,608,189 B1 | 8/2003 | Tsien et al. |
| 6,762,025 B2 * | 7/2004 | Cubicciotti .................. 435/6 |
| 6,766,183 B2 | 7/2004 | Walsh et al. |
| 6,790,632 B2 | 9/2004 | Zweig |

(Continued)

FOREIGN PATENT DOCUMENTS
EP         1 226 436 B1     4/2005
(Continued)

OTHER PUBLICATIONS

Allen et al., "Resonance Energy Transfer Measurements Between Substrate Binding Sites Within the Large (Klenow) Fragment of *Escherichia coli* DNA Polymerase I," *Biochem.* 28:9586-9593 (1989).

Ason et al., "A Model for *Escherichia coli* DNA Polymerase III Holoenzyme Assembly at Primer/Template Ends," *J. Biol. Chem.* 275:3006-3015 (2000).

Baubet et al., "Chimeric Green Fluorescent Protein-Aequorin as Bioluminiscent $Ca^{2+}$ Reporters at the Single-Cell Level," *Proc. Natl. Acad. Sci. USA* 97:7260-7265 (2000).

(Continued)

*Primary Examiner* — Amy Bowman
(74) *Attorney, Agent, or Firm* — Klarquist Sparkman, LLP

(57) ABSTRACT

The disclosure provides probes for one or more target molecules. In particular examples, the probes include a molecular linker and first and second functional groups linked and spaced by the molecular linker, wherein the functional groups are capable of interacting with one another or with the target biomolecule in a predetermined reaction, and wherein the molecular linker maintains the first and second functional groups sufficiently spaced from one another such that the functional groups do not substantially interact in an absence of the target biomolecule. In the presence of the target biomolecule the functional groups interact (with each other, with the target biomolecule, or both), and in some examples a detectable signal is produced. In some examples, the functional groups can detect or modify a target molecule. Also provided are methods of using the probes, for example to detect or modify a target molecule.

37 Claims, 22 Drawing Sheets

U.S. PATENT DOCUMENTS

| | | | |
|---|---|---|---|
| 6,890,556 | B1 | 5/2005 | Segura et al. |
| 6,908,736 | B1 | 6/2005 | Densham |
| 6,982,146 | B1 | 1/2006 | Schneider et al. |
| 7,018,792 | B2 * | 3/2006 | Swanson et al. ............ 435/5 |
| 7,033,764 | B2 | 4/2006 | Korlach et al. |
| 7,052,847 | B2 | 5/2006 | Korlach et al. |
| 7,056,661 | B2 | 6/2006 | Korlach et al. |
| 7,172,865 | B2 | 2/2007 | Heyduk |
| 2002/0164629 | A1 | 11/2002 | Quake et al. |
| 2002/0165364 | A1 | 11/2002 | Tsien et al. |
| 2002/0193672 | A1 | 12/2002 | Walsh et al. |
| 2003/0064366 | A1 | 4/2003 | Hardin et al. |
| 2003/0134807 | A1 | 7/2003 | Hardin et al. |
| 2003/0170767 | A1 | 9/2003 | Cubitt |
| 2003/0212265 | A1 | 11/2003 | Tsien et al. |
| 2004/0091931 | A1 | 5/2004 | Gold |
| 2004/0265902 | A1 | 12/2004 | Fricker et al. |
| 2005/0267326 | A1 | 12/2005 | Loeb et al. |
| 2006/0112440 | A1 | 5/2006 | Tsien et al. |
| 2006/0211075 | A1 | 9/2006 | Lawrence et al. |

FOREIGN PATENT DOCUMENTS

| | | |
|---|---|---|
| WO | WO 97/30366 A1 | 8/1997 |
| WO | WO 97/40191 A1 | 10/1997 |
| WO | WO 98/33939 A1 | 8/1998 |
| WO | WO 98/40477 A1 | 9/1998 |
| WO | WO 99/05315 A2 | 2/1999 |
| WO | WO 00/53805 A1 | 9/2000 |
| WO | WO 00/70073 A1 | 11/2000 |
| WO | WO 01/16375 A2 | 3/2001 |
| WO | WO 02/04680 A2 | 1/2002 |
| WO | WO 02/090987 A2 | 11/2002 |
| WO | WO 2004/074503 A2 | 9/2004 |
| WO | WO2005/077065 A2 | 8/2005 |

OTHER PUBLICATIONS

Beaucage et al., "Persistence Length of Isotactic Poly(hydroxy butyrate)," *Macromolecules* 30:4158-4162 (1997).

Blessing et al., "Different Strategies for Formation of Pegylated EGF-Conjugated PEI/DNA Complexes for Targeted Gene Delivery," *Bioconjugate Chem.* 12:529-537 (2001).

Blossey and Carlon, "Reparametrizing the Loop Entropy Weights: Effect on DNA Melting Curves," *Phys. Rev. E*68:061911 (2003).

Braslaysky et al., "Sequence Information can be Obtained from Single DNA Molecules," *Proc. Natl. Acad. Sci.* 100:3960-3964 (2003).

Burns et al., "Studies in Fluorescence Histochemistry. X. Optimum Conditions of the Acetic Anhydride-Salicylhydrazide-Zinc (or Fluorescent Ketone) Technique for Demonstrating C-Terminal Carboxyl Groups of Proteins," *Histochemie* 26:279-288 (1971).

Clegg, "Fluorescence Resonance Energy Transfer and Nucleic Acids," *Methods in Enzymol.* 211:353-388 (1992).

Delagrave et al., "Red-Shifted Excitation Mutants of the Green Fluorescent Protein," *Bio/Tech.* 13:151-154 (1995).

Ehrig et al., "Green-Fluorescent Protein Mutants with Altered Fluorescence Excitation Spectra," *FEBS Lett.* 367:163-166 (1995).

Fang and Tan, Ímaging Single Fluorescent Molecules at the Interface of an Optical Fiber Probe by Evanescent Wave Excitation, *Anal. Chem.* 71:3101-3105 (1999).

Funatsu et al., "Imaging of Single Fluorescent Molecules and Individual ATP Turnovers by Single Myosin Molecules in Aqueous Solution," *Nature* 374:555-559 (1995).

Furey et al., "Use of Fluorescence Resonance Energy Transfer to Investigate the Conformation of DNA Substrates Bound to the Klenow Fragment," *Biochemistry* 37:2979-2990 (1998).

Gordon et al., "Quantitative Fluorescence Resonance Energy Transfer Measurements Using Fluorescence Microscopy," *Biophys J.* 74:2702-2313 (1998).

Grant et al., "Development of Dual Receptor Biosensors: An Analysis of FRET Pairs," *Biosens. Bioelectron.* 16:231-237 (2001).

Grant et al., "Viability of a FRET Dual Binding Technique to Detect Calpastatin," *Biosens. Bioelectron.* 21:438-444 (2005).

Ha et al., Probing the Interaction Between Two Single Molecules: Fluorescence Resonance Energy Transfer Between a Single Donor and a Single Acceptor, *Proc. Natl. Acad. Sci. USA* 93:6264-6268 (1996).

Halpin and Harbury, "DNA Display II. Genetic Manipulation of Combinatorial Chemistry Libraries for Small-Molecule Evolution," *PLOS Biol.* 2:1022-1030 (2004).

Harada et al., "Mechanochemical Coupling in Actomyosin Energy Transduction Studied by in Vitro Movement Assay," *J. Mol. Biol.* 216:49-68 (1990).

Harms et al., "Single-Molecule Anisotrophy Imaging," *Biophys. J.* 77:2864-2870 (1999).

Hayashi et al., "A Single Expression System for the Display, Purification and Conjugation of Single-Chain Antibodies," *Gene* 160:129-130 (1995).

Hengen et al., "Molecular Flip-Flops Formed by Overlapping Fis Sites," *Nucl. Acid. Res.* 31:6663-6673 (2003).

Heyduk and Heyduk, "Architecture of a Complex Between the $\sigma^{70}$ Subunit of *Escherichia coli* RNA Polymerase and the Nontemplate Strand Oligonucleotide," *J. Biol. Chem.* 274:3315-3322 (1999).

Heyduk and Heyduk, "Thiol-Reactive, Luminescent Europium Chelates: Luminescence Probes for Resonance Energy Transfer Distance Measurements in Biomolecules," *Anal. Biochem.* 248:216-227 (1997).

Hung et al., "Cyanine Dyes with High Absorption Cross Section as Donor Chromophores in Energy Transfer Primers," *Anal. Biochem.* 243:15-27 (1996).

Inouye and Tsuji, "*Aequorea* Green Fluorescent Protein. Expression of the Gene and Fluorescence Characteristics of the Recombinant Protein," *FEBS Lett.* 341:277-280 (1994).

Itakura et al., "Force-Generating Domain of Myosin Motor," *Biochem. Biophys. Res. Comm.* 196:1504-1510 (1993).

Kaku et al., "Binding to the Naturally Occurring Double p53 Binding Site of the Mdm2 Promoter Alleviates the Requirement for p53 C-Terminal Activation," *Nucleic Acids Res.* 29:1989-1993 (2001).

Karger et al., "Multiwavelength Fluorescence Detection for DNA Sequencing Using Capillary Electrophoresis," *Nucleic Acids Res.* 19:4955-4962 (1991).

Kheterpal and Mathies, "Capillary Array Electrophoresis DNA Sequencing," *Analy. Chem. News & Features*, pp. 31A-37A (1999).

Khidekel et al., "A Chemoenzymatic Approach Toward the Rapid and Sensitive Detection of O-GlcNAc Posttranslational Modifications," *J. Am. Chem. Soc.* 125:16162-16163 (2003).

Kitamura et al., "A Single Myosin Head Moves Along an Actin Filament with Regular Steps of 5.3 Nanometres," *Nature* 397:129-134 (1999).

Knoll and Heyduk, "Unimolecular Beacons for Detection of DNA Binding Proteins," *Anal. Chem.* 76:1156-1164 (2004).

Ko and Grant, "A Novel FRET-Based Optical Fiber Biosensor for Rapid Detection of *Salmonella typhimurium*," *Biosens. Bioelectron.* 21:1283-1290 (2006).

Korlach et al., "Spontaneous Nucleotide Exchange in Low Molecular Weight GTPases by Fluorescently Labeled γ-Phosphate-Linked GTP Analogs," *Proc Natl. Acad. Sci. USA* 101:2800-2805 (2004).

Kozlov et al., "Efficient Strategies for the Conjugation of Oligonucleotides to Antibodies Enabling Highly Sensitive Protein Detection," *Biopolymers* 73:621-630 (2004).

Kumar et al., "Silanized Nucleic Acids: A General Platform for DNA Immobilization," *Nucleic Acids Res.* 28:e71 (2000).

Lemon and Grossman, "Localization of Bacterial DNA Polymerase: Evidence for a Factory Model of Replication," *Science* 282:1516-1519 (1998).

Marko and Siggia, "Stretching DNA," *Macromolecules* 28:8759-8770 (1995).

Marras et al., "Multiplex Detection of Single-Nucleotide Variations Using Molecular Beacons," *Genetic Analysis: Biomolecular Engineering* 14:151-156 (1999).

Mazzola and Fodor, "Imaging Biomolecule Arrays by Atomic Force Microscopy," *Biophys. J.* 68:1653-1660 (1995).

Minor and Kulesz-Martin, "DNA Binding Specificity of Proteins Derived from Alternatively Spliced Mouse p53 mRNAs," *Nucleic Acids Res.* 25:1319-1326 (1997).

Mitra et al., "Fluorescence Resonance Energy Transfer Between Blue-Emitting and Red-Shifted Excitation Derivatives of the Green Fluorescent Protein," *Gene 173:*13-17 (1996).

Müllner, et al., "A Strategy for the Chemical Synthesis of Nanostructures," *Science 268:*272-273 (1995).

Nakatani et al., "Highly Sensitive Detection of GG Mismatchd DNA by Surfaces Immobilized Naphthyridine Dimer Through Poly(ethylene oxide) Linkers," *Bioorganic Med. Chem. Lett. 14:*1105-1108 (2004).

Ng and Bergstrom, "Protein-DNA Footprinting by Endcapped Duplex Oligodexyribonucleotides," *Nucleic Acids Res. 32:*e107 (2004).

Niemeyer et al., "Oligonucleotide-Directed Self-Assembly of Proteins: Semisynthetic DNA—Streptavidin Hybrid Molecules as Connectors for the Generation of Macroscopic Arrays and the Construction of Supramolecular Bioconjugates," *Nucleic Acids Res. 22:*5530-5539 (1994).

Park et al., "Block Copolymer Lithography: Periodic Arrays of ~$10^{11}$ Holes in 1 Square Centimeter," *Science 276:*1401-1404 (1997).

Park and Raines, "Green Fluorescent Protein as a Signal for Protein-Protein Interactions," *Protein Science 6:*2344-2349 (1997).

Perkins et al., "Relaxation of a Single DNA Molecule Observed by Optical Microscopy," *Science 264:*822-826 (1994).

Pierce et al., "Imaging Individual Green Fluorescent Proteins," *Nature 388:*338 (1997).

Sinclair, "Sequence or Die—Automated Instrumentation for the Genome Era," *The Scientist*, pp. 18-20, Apr. 12, 1999.

Szöllosi et al., "Application of Fluorescence Resonance Energy Transfer in the Clinical Laboratory: Routine and Research," *Cytometry 34:*159-179 (1998).

Travis, "Physics Festival Brightens Rainy San Jose," *Science 268:*30-31 (1995).

Unger et al., "Single-Molecule Fluorescence Observed with Mercury Lamp Illumination," *BioTechniques 27:*1008-1014 (1999).

Wang et al., "Size, Shape, and Stability of InAs Quantum Dots on the GaAs(001) Substrate," *Phys. Rev. B 62:*1897-1904 (2000).

Weiss, "Fluorescence Spectroscopy of Single Biomolecules," *Science 283:*1676-1683 (1999).

Wenner et al., "Salt Dependence of the Elasticity and Overstretching Transition of Single DNA Molecules," *Biophys. J. 82:*3160-3169 (2002).

Zahavy et al., "Detection of Frequency Resonance Energy Transfer Pair on Double-Labeled Microsphere and *Bacillus anthraces* Spores by Flow Cytometry," *Appl. Environ. Microbiol. 69:*2330-2339 (2003).

Adair, "Colloidal Lessons Learned for Dispersion of Nanosize Particulate Suspensions," *Lessons in Nanotechnology from Traditional and Advanced Ceramics*, pp. 93-94, 2005.

Johnson et al., "Amino-Terminal Dimerization of an Erythropoietin Mimetic Peptide Results in Increased Erythropoietic Activity," *Chem. Biol. 4:*939-950, 1997.

Slate et al., "Engineering of Five 88-Residue Receptor-Adhesive Modular Proteins Containing a Parallel α-Helical Coiled Coil and Two RGD Ligand Sites," *Int. J. Peptide Protein Res. 45:*290-298, 1995.

\* cited by examiner

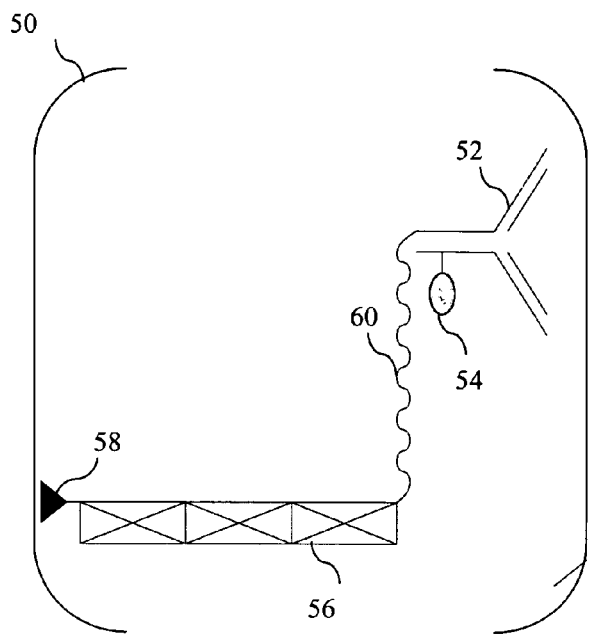
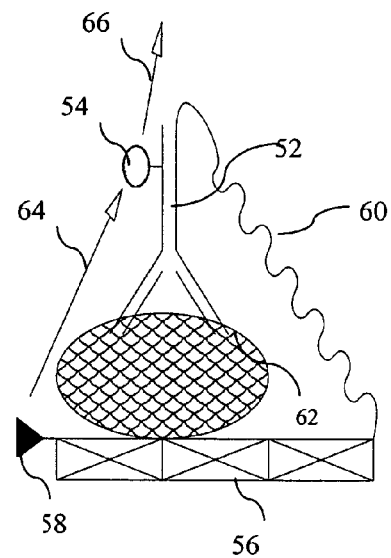
FIG. 2A  FIG. 2B
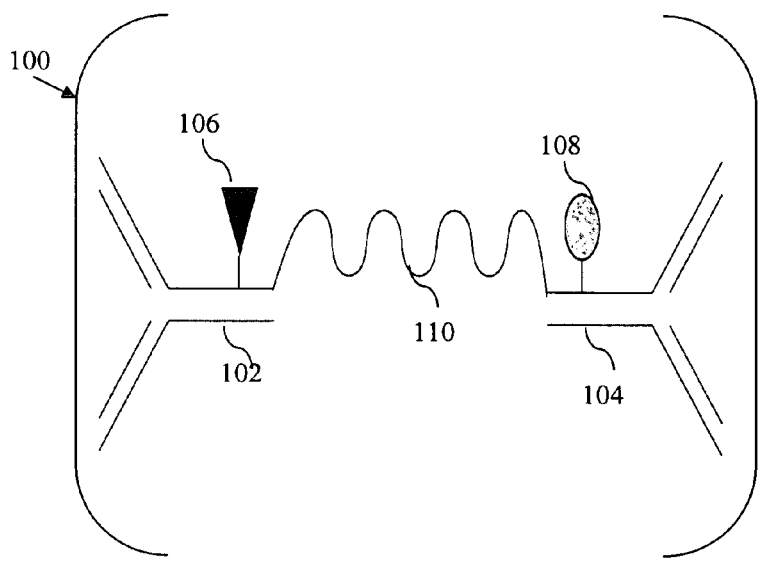
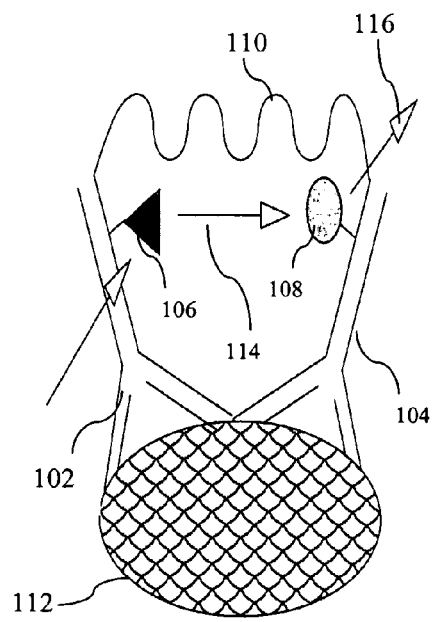
FIG. 3A  FIG. 3B

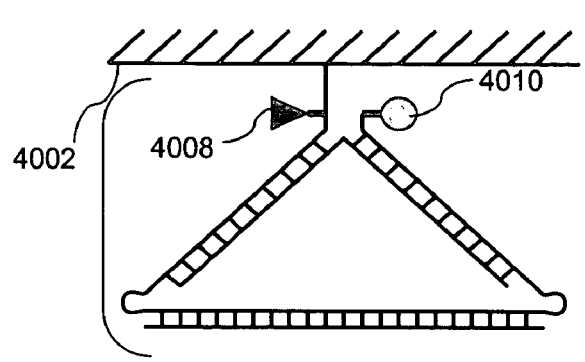
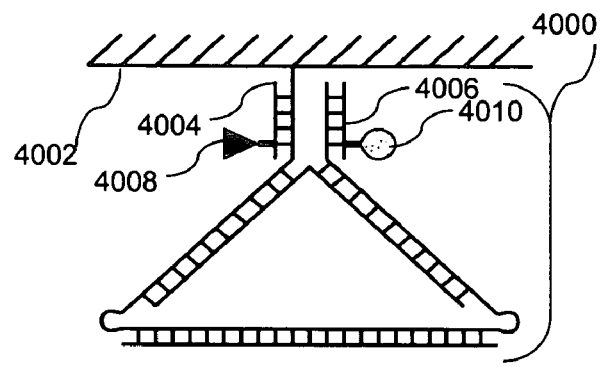
FIG. 19A  FIG. 19B
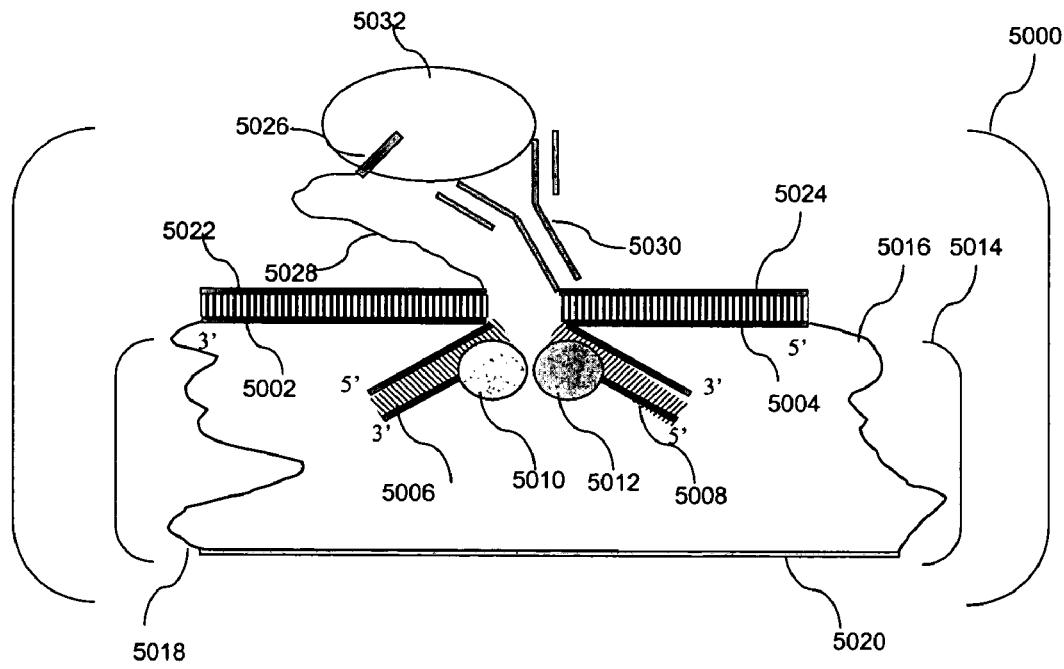
FIG. 20

SEQUENCE LISTING

```
<160> NUMBER OF SEQ ID NOS: 96

<210> SEQ ID NO 1
<211> LENGTH: 20
<212> TYPE: DNA
<213> ORGANISM: Homo sapiens

<400> SEQUENCE: 1
gaacatgccc gggcatgtcc                                                   20

<210> SEQ ID NO 2
<211> LENGTH: 21
<212> TYPE: DNA
<213> ORGANISM: Homo sapiens

<400> SEQUENCE: 2
gaacatgtcc caaacatgtt g                                                 21

<210> SEQ ID NO 3
<211> LENGTH: 19
<212> TYPE: DNA
<213> ORGANISM: Artificial sequence
<220> FEATURE:
<223> OTHER INFORMATION: p53 binding sequence
<220> FEATURE:
<221> NAME/KEY: misc_feature
<222> LOCATION: (1)..(3)
<223> OTHER INFORMATION: r is any purine
<220> FEATURE:
<221> NAME/KEY: misc_feature
<222> LOCATION: (5)..(6)
<223> OTHER INFORMATION: w is a or t
<220> FEATURE:
<221> NAME/KEY: misc_feature
<222> LOCATION: (8)..(10)
<223> OTHER INFORMATION: y is any pyrimidine
<220> FEATURE:
<221> NAME/KEY: misc_feature
<222> LOCATION: (11)..(13)
<223> OTHER INFORMATION: r is any purine
<220> FEATURE:
<221> NAME/KEY: misc_feature
<222> LOCATION: (15)..(16)
<223> OTHER INFORMATION: w is a or t
<220> FEATURE:
<221> NAME/KEY: misc_feature
<222> LOCATION: (18)..(19)
<223> OTHER INFORMATION: y is any pyrimidine

<400> SEQUENCE: 3 rrrcwgyyy rrrcwgyy                                                      19
```

-continued

```
<210> SEQ ID NO 4
<211> LENGTH: 47
<212> TYPE: DNA
<213> ORGANISM: Homo sapiens

<400> SEQUENCE: 4
ggacatgtcc ggacatgtcc gcgaagcgga catgtccgga catgtcc                  47

<210> SEQ ID NO 5
<211> LENGTH: 40
<212> TYPE: DNA
<213> ORGANISM: Artificial sequence
<220> FEATURE:
<223> OTHER INFORMATION: exemplary molecular rod sequence

<400> SEQUENCE: 5
gacgctagta tcttatgaag ctttcctgac tgcggcatta                          40

<210> SEQ ID NO 6
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: the nucleotide at position 1 is 5' linked to
      NH2-[PEG18][PEG18]

<400> SEQUENCE: 6
gacgctagta tcttatgaag ctttcctgac tgcggcatta                          40

<210> SEQ ID NO 7
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: the nucleotide at position 1 is 5' linked to
      NH2-[PEG18][PEG18]

<400> SEQUENCE: 7
taatgccgca gtcaggaaag cttcataaga tactagcgtc                          40

<210> SEQ ID NO 8
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (20)..(20)
<223> OTHER INFORMATION: the nucleotide at position 20 is 3' linked to
      6-FAM

<400> SEQUENCE: 8
gtgccgtcga attctcgcta                                                20

<210> SEQ ID NO 9
<211> LENGTH: 60
<212> TYPE: DNA
```

```
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: the nucleotide at position 1 is amino-modified
<220> FEATURE:
<221> NAME/KEY: misc_feature
<222> LOCATION: (20)..(21)
<223> OTHER INFORMATION: The linkage between nucleotide 20 and 21 is
      -[PEG18]-[PEG18]-

<400> SEQUENCE: 9
tagcgagaat tcgacggcac gacgctagta tcttatgaag ctttcctgac tgcggcatta      60

<210> SEQ ID NO 10
<211> LENGTH: 60
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: the nucleotide at position 1 is amino-modified
<220> FEATURE:
<221> NAME/KEY: misc_feature
<222> LOCATION: (20)..(21)
<223> OTHER INFORMATION: The linkage between nucleotide 20 and 21 is
      -[PEG18]-[PEG18]-

<400> SEQUENCE: 10
cgatagggat ccattactgc taatgccgca gtcaggaaag cttcataaga tactagcgtc      60

<210> SEQ ID NO 11
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (20)..(20)
<223> OTHER INFORMATION: the nucleotide at position 20 is 3' linked to
      Texas Red

<400> SEQUENCE: 11
gcagtaatgg atccctatcg                                                  20

<210> SEQ ID NO 12
<211> LENGTH: 46
<212> TYPE: DNA
<213> ORGANISM: Artificial sequence
<220> FEATURE:
<223> OTHER INFORMATION: exemplary target sequence

<400> SEQUENCE: 12
tctatacgga tccttacgct cacccagtct cgcgaattcc ggcctt                     46

<210> SEQ ID NO 13
<211> LENGTH: 120
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
```

```
<222> LOCATION: (40)..(41)
<223> OTHER INFORMATION: The linkeage between nucleotide 40 and 41 is
      -[PEG18]-[PEG18]-[PEG18]-
<220> FEATURE:
<221> NAME/KEY: misc_feature
<222> LOCATION: (80)..(81)
<223> OTHER INFORMATION: The linkeage between nucleotide 80 and 81 is
      -[PEG18]-[PEG18]-[PEG18]-

<400> SEQUENCE: 13
tagcgagaat tcgacggcac agcgtaagga tccgtataga gacgctagta tcttatgaag      60
ctttcctgac tgcggcatta aaggccggaa ttcgcgagac cgatagggat ccattactgc     120

<210> SEQ ID NO 14
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: the nucleotide at position 1 is 5' linked to
      [6-FAM]

<400> SEQUENCE: 14
gtgccgtcga attctcgcta                                                  20

<210> SEQ ID NO 15
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (20)..(20)
<223> OTHER INFORMATION: the nucleotide at position 20 is 3' linked to
      Texas Red

<400> SEQUENCE: 15
gcagtaatgg atccctatcg                                                  20

<210> SEQ ID NO 16
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 16
taatgccgca gtcaggaaag cttcataaga tactagcgtc                            40

<210> SEQ ID NO 17
<211> LENGTH: 30
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 17
ccgcagtcag gaaagcttca taagatacta                                       30

<210> SEQ ID NO 18
<211> LENGTH: 20
```

```
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 18
gtcaggaaag cttcataaga                                                    20

<210> SEQ ID NO 19
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 19
tctatacgga tccttacgct ccattgttca atatcgtccg                              40

<210> SEQ ID NO 20
<211> LENGTH: 41
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 20
tctatacgga tccttacgct tccattgttc aatatcgtcc g                            41

<210> SEQ ID NO 21
<211> LENGTH: 42
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 21
tctatacgga tccttacgct ttccattgtt caatatcgtc cg                           42

<210> SEQ ID NO 22
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 22
tcatctggac ctgggtcttc gtctcgcgaa ttccggcctt                              40

<210> SEQ ID NO 23
<211> LENGTH: 41
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 23
tcatctggac ctgggtcttc tgtctcgcga attccggcct t                            41

<210> SEQ ID NO 24
<211> LENGTH: 42
<212> TYPE: DNA
<213> ORGANISM: Artificial sequence
```

```
<220> FEATURE:
<223> OTHER INFORMATION: exemplary sequence that can be used in making
      a nanoprobe.

<400> SEQUENCE: 24
tcatctggac ctgggtcttc ttgtctcgcg aattccggcc tt                         42

<210> SEQ ID NO 25
<211> LENGTH: 40
<212> TYPE: DNA
<213> ORGANISM: Artificial sequence
<220> FEATURE:
<223> OTHER INFORMATION: exemplary target sequence

<400> SEQUENCE: 25
cgatagggat ccattactgc tagcgagaat tcgacggcac                            40

<210> SEQ ID NO 26
<211> LENGTH: 60
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: the nucleotide at position 1 is 5' linked to
      [6-FAM]
<220> FEATURE:
<221> NAME/KEY: misc_feature
<222> LOCATION: (20)..(21)
<223> OTHER INFORMATION: The linkeage between nucleotide 20 and 21 is
      -[PEG18]-[PEG18]-

<400> SEQUENCE: 26
gcagtaatgg atccctatcg taatgccgca gtcaggaaag cttcataaga tactagcgtc      60

<210> SEQ ID NO 27
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (21)..(21)
<223> OTHER INFORMATION: The t at position 21 is labeled with Texas Red
<220> FEATURE:
<221> NAME/KEY: misc_feature
<222> LOCATION: (21)..(22)
<223> OTHER INFORMATION: The linkage betwen nucleotide 21 and 22 is
      [PEG18][PEG18]

<400> SEQUENCE: 27
gtgccgtcga attctcgcta tgacgctagt atcttatgaa                            40

<210> SEQ ID NO 28
<211> LENGTH: 21
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: the nucleotide at position 1 is 5' linked to
      ligase-[peg18][peg18]

<400> SEQUENCE: 28
```

```
gctttcctga ctgcggcatt a                                            21

<210> SEQ ID NO 29
<211> LENGTH: 23
<212> TYPE: DNA
<213> ORGANISM: Artificial sequence
<220> FEATURE:
<223> OTHER INFORMATION: exemplary target sequence

<400> SEQUENCE: 29
cggacgatat tgaacaatgg ttc                                          23

<210> SEQ ID NO 30
<211> LENGTH: 23
<212> TYPE: DNA
<213> ORGANISM: Artificial sequence
<220> FEATURE:
<223> OTHER INFORMATION: exemplary target sequence

<400> SEQUENCE: 30
actgaagacc caggtccaga tga                                          23

<210> SEQ ID NO 31
<211> LENGTH: 23
<212> TYPE: DNA
<213> ORGANISM: Artificial sequence
<220> FEATURE:
<223> OTHER INFORMATION: exemplary target sequence

<400> SEQUENCE: 31
tcagctattt gcgtgtgagg aaa                                          23

<210> SEQ ID NO 32
<211> LENGTH: 23
<212> TYPE: DNA
<213> ORGANISM: Artificial sequence
<220> FEATURE:
<223> OTHER INFORMATION: exemplary target sequence

<400> SEQUENCE: 32
cttctggatg ctggtgattt gga                                          23

<210> SEQ ID NO 33
<211> LENGTH: 23
<212> TYPE: DNA
<213> ORGANISM: Artificial sequence
<220> FEATURE:
<223> OTHER INFORMATION: exemplary target sequence

<400> SEQUENCE: 33
gccagtaccg ccaactgaag acg                                          23

<210> SEQ ID NO 34
<211> LENGTH: 23
<212> TYPE: DNA
<213> ORGANISM: Artificial sequence
<220> FEATURE:
<223> OTHER INFORMATION: exemplary target sequence

<400> SEQUENCE: 34
gccgaggact atcaggccct gaa                                          23

<210> SEQ ID NO 35
<211> LENGTH: 23
<212> TYPE: DNA
<213> ORGANISM: Artificial sequence
```

-continued

```
<220> FEATURE:
<223> OTHER INFORMATION: exemplary target sequence

<400> SEQUENCE: 35
tggtgatgga cggcgtaatc tct                                              23

<210> SEQ ID NO 36
<211> LENGTH: 23
<212> TYPE: DNA
<213> ORGANISM: Artificial sequence
<220> FEATURE:
<223> OTHER INFORMATION: exemplary target sequence

<400> SEQUENCE: 36
gaccacgagt gtcaggagct gca                                              23

<210> SEQ ID NO 37
<211> LENGTH: 23
<212> TYPE: DNA
<213> ORGANISM: Artificial sequence
<220> FEATURE:
<223> OTHER INFORMATION: exemplary target sequence

<400> SEQUENCE: 37
tgggctttga caaacagctc tca                                              23

<210> SEQ ID NO 38
<211> LENGTH: 23
<212> TYPE: DNA
<213> ORGANISM: Artificial sequence
<220> FEATURE:
<223> OTHER INFORMATION: exemplary target sequence

<400> SEQUENCE: 38
caggacctgg ctgtcaacct cct                                              23

<210> SEQ ID NO 39
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 39
ccattgttca atatcgtccg                                                  20

<210> SEQ ID NO 40
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 40
tcatctggac ctgggtcttc                                                  20

<210> SEQ ID NO 41
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 41
cctcacacgc aaatagctga                                                  20
```

```
<210> SEQ ID NO 42
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 42
tccaaatcac cagcatccag                                                   20

<210> SEQ ID NO 43
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 43
cttcagttgg cggtactggc                                                   20

<210> SEQ ID NO 44
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 44
ttcagggcct gatagtcctc                                                   20

<210> SEQ ID NO 45
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 45
gattacgccg tccatcacca                                                   20

<210> SEQ ID NO 46
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 46
tgcagctcct gacactcgtg                                                   20

<210> SEQ ID NO 47
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 47
gagctgtttg tcaaagccca                                                   20

<210> SEQ ID NO 48
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 48
```

```
aggaggttga cagccaggtc                                               20

<210> SEQ ID NO 49
<211> LENGTH: 21
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: the nucleotide at position 1 is 5' linked to
      RNaseH-[PEG18][PEG18]

<400> SEQUENCE: 49
gctttcctga ctgcggcatt a                                             21

<210> SEQ ID NO 50
<211> LENGTH: 20
<212> TYPE: DNA
<213> ORGANISM: Artificial sequence
<220> FEATURE:
<223> OTHER INFORMATION: exemplary target sequence

<400> SEQUENCE: 50
ggacatgtcc ggacatgtcc                                               20

<210> SEQ ID NO 51
<211> LENGTH: 27
<212> TYPE: DNA
<213> ORGANISM: Artificial sequence
<220> FEATURE:
<223> OTHER INFORMATION: exemplary target sequence

<400> SEQUENCE: 51
ggacatgtcc ggacatgtcc gcgaagc                                       27

<210> SEQ ID NO 52
<211> LENGTH: 25
<212> TYPE: DNA
<213> ORGANISM: Artificial sequence
<220> FEATURE:
<223> OTHER INFORMATION: exemplary target sequence

<400> SEQUENCE: 52
tctcacacac gtacacacac gtgtc                                         25

<210> SEQ ID NO 53
<211> LENGTH: 32
<212> TYPE: DNA
<213> ORGANISM: Artificial sequence
<220> FEATURE:
<223> OTHER INFORMATION: exemplary target sequence

<400> SEQUENCE: 53
tctcacacac gtacacacac gtgtcgcgaa gc                                 32

<210> SEQ ID NO 54
<211> LENGTH: 20
<212> TYPE: DNA
<213> ORGANISM: Artificial sequence
<220> FEATURE:
<223> OTHER INFORMATION: exemplary target sequence

<400> SEQUENCE: 54
gggacattcc gggacattcc                                               20
```

<210> SEQ ID NO 55
<211> LENGTH: 27
<212> TYPE: DNA
<213> ORGANISM: Artificial sequence
<220> FEATURE:
<223> OTHER INFORMATION: exemplary target sequence

<400> SEQUENCE: 55
gggacattcc gggacattcc gcgaagc                                      27

<210> SEQ ID NO 56
<211> LENGTH: 25
<212> TYPE: DNA
<213> ORGANISM: Artificial sequence
<220> FEATURE:
<223> OTHER INFORMATION: exemplary target sequence

<400> SEQUENCE: 56
gtcgacattt cccgtaaatc gtcga                                        25

<210> SEQ ID NO 57
<211> LENGTH: 32
<212> TYPE: DNA
<213> ORGANISM: Artificial sequence
<220> FEATURE:
<223> OTHER INFORMATION: exemplary target sequence

<400> SEQUENCE: 57
gtcgacattt cccgtaaatc gtcgagcgaa gc                                32

<210> SEQ ID NO 58
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 58
ggacatgtcc ggacatgtcc                                              20

<210> SEQ ID NO 59
<211> LENGTH: 25
<212> TYPE: DNA
<213> ORGANISM: Artificial sequence
<220> FEATURE:
<223> OTHER INFORMATION: exemplary nanoprobe sequence

<400> SEQUENCE: 59
gacacgtgtg tgtacgtgtg tgaga                                        25

<210> SEQ ID NO 60
<211> LENGTH: 20
<212> TYPE: DNA
<213> ORGANISM: Artificial sequence
<220> FEATURE:
<223> OTHER INFORMATION: exemplary nanoprobe sequence

<400> SEQUENCE: 60
ggaatgtccc ggaatgtccc                                              20

<210> SEQ ID NO 61
<211> LENGTH: 25
<212> TYPE: DNA
<213> ORGANISM: Artificial sequence
<220> FEATURE:
<223> OTHER INFORMATION: exemplary nanoprobe sequence

```
<400> SEQUENCE: 61
tcgacgattt acgggaaatg tcgac                                          25

<210> SEQ ID NO 62
<211> LENGTH: 40
<212> TYPE: DNA
<213> ORGANISM: Artificial sequence
<220> FEATURE:
<223> OTHER INFORMATION: exemplary nanoprobe sequence
<220> FEATURE:
<221> NAME/KEY: misc_feature
<222> LOCATION: (1)..(1)
<223> OTHER INFORMATION: the nucleotide at position 1 is 5' linked to
      [PEG18][PEG18]
<220> FEATURE:
<221> NAME/KEY: misc_feature
<222> LOCATION: (40)..(40)
<223> OTHER INFORMATION: the nucleotide at position 40 is 3' linked to
      [PEG18][PEG18]-[Texas Red]

<400> SEQUENCE: 62
taatgccgca gtcaggaaag cttcataaga tactagcgtc                          40

<210> SEQ ID NO 63
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 63
ggcctccgtc ctcggcagta                                                20

<210> SEQ ID NO 64
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 64
tactgccgag gacggaggcc                                                20

<210> SEQ ID NO 65
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 65
cgataatgcc tgtcatgcat                                                20

<210> SEQ ID NO 66
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 66
atgcatgaca ggcattatcg                                                20
```

```
<210> SEQ ID NO 67
<211> LENGTH: 19
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 67
gaacgtctag acttatcgc                                                  19

<210> SEQ ID NO 68
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 68
gcgataagtc tagacgttcc                                                 20

<210> SEQ ID NO 69
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 69
ctctcgctcc gtgccgtaag                                                 20

<210> SEQ ID NO 70
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 70
cttacggcac ggagcgagag                                                 20

<210> SEQ ID NO 71
<211> LENGTH: 71
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 71
cgctcctgaa ttcgacgtac gctatatatt tagtatgttg taactaaagt ccagcgcgaa    60
gcttaatgac t                                                          71

<210> SEQ ID NO 72
<211> LENGTH: 71
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 72
attcagtctg caggaaggcc gactttagtt acaacatact aaatatatag ccagtaaggg    60
atccgatctc g                                                          71
```

```
<210> SEQ ID NO 73
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 73
gtacgtcgaa ttcaggagcg                                              20

<210> SEQ ID NO 74
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 74
cgagatcgga tcccttactg                                              20

<210> SEQ ID NO 75
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 75
agtcattaag cttcgcgctg                                              20

<210> SEQ ID NO 76
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 76
ggccttcctg cagactgaat                                              20

<210> SEQ ID NO 77
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: The nucleotide at position 1 is 5' linked to
      Rhodamine Red

<400> SEQUENCE: 77
ggcctccgtc ctcggcagta                                              20

<210> SEQ ID NO 78
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.
<220> FEATURE:
```

```
<221> NAME/KEY: misc_feature
<222> LOCATION: (20)..(20)
<223> OTHER INFORMATION: the nucleotide at position 20 is 3' linked to
      Cy3

<400> SEQUENCE: 78
cgataatgcc tgtcatgcat                                               20

<210> SEQ ID NO 79
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (20)..(20)
<223> OTHER INFORMATION: the nucleotide at position 20 is 3' linked to
      Texas Red.

<400> SEQUENCE: 79
ggaacgtcta gacttatcgc                                               20

<210> SEQ ID NO 80
<211> LENGTH: 20
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: the nucleotide at position 1 is 5' linked to
      Cy5

<400> SEQUENCE: 80
ctctcgctcc gtgccgtaag                                               20

<210> SEQ ID NO 81
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (20)..(21)
<223> OTHER INFORMATION: The linkeage between nucleotide 20 and 21 is
      -[PEG18]-[PEG18]-[PEG18]-
<220> FEATURE:
<221> NAME/KEY: misc_feature
<222> LOCATION: (40)..(40)
<223> OTHER INFORMATION: The nucleotide at position 40 is 3' linked to
      [PEG9]-NH2

<400> SEQUENCE: 81
gtacgtcgaa ttcaggagcg tactgccgag gacggaggcc                         40

<210> SEQ ID NO 82
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: The nucleotide at position 1 is 5' linked to
```

```
        NH2-[PEG9]
<220> FEATURE:
<221> NAME/KEY: misc_feature
<222> LOCATION: (20)..(21)
<223> OTHER INFORMATION: The linkeage between nucleotide 20 and 21 is
      -[PEG18]-[PEG18]-[PEG18]- [PEG18]-[PEG18]-[PEG18]

<400> SEQUENCE: 82
atgcatgaca ggcattatcg cgagatcgga tcccttactg                              40

<210> SEQ ID NO 83
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: The nucleotide at position 1 is 5' linked to
      NH2-[PEG9]
<220> FEATURE:
<221> NAME/KEY: misc_feature
<222> LOCATION: (20)..(21)
<223> OTHER INFORMATION: The linkeage between nucleotide 20 and 21 is
      [PEG18]-[PEG18]-[PEG18]

<400> SEQUENCE: 83
gcgataagtc tagacgttcc agtcattaag cttcgcgctg                              40

<210> SEQ ID NO 84
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (20)..(21)
<223> OTHER INFORMATION: The linkeage between nucleotide 20 and 21 is
      [PEG18]-[PEG18]-[PEG18]
<220> FEATURE:
<221> NAME/KEY: misc_feature
<222> LOCATION: (40)..(40)
<223> OTHER INFORMATION: The nucleotide at position 1 is 3' linked to
      [PEG9]-NH2
<220> FEATURE:
<221> NAME/KEY: misc_feature
<222> LOCATION: (40)..(40)
<223> OTHER INFORMATION: The nucleotide at position 40 is 3' linked to
      [PEG9]-NH2

<400> SEQUENCE: 84
ggccttcctg cagactgaat cttacggcac ggagcgagag                              40

<210> SEQ ID NO 85
<211> LENGTH: 71
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 85
cgctcctgaa ttcgacgtac gctatatatt tagtatgttg taactaaagt ccagcgcgaa        60
gcttaatgac t                                                             71

<210> SEQ ID NO 86
<211> LENGTH: 71
```

```
<212> TYPE: DNA
<213> ORGANISM: Artificial sequence
<220> FEATURE:
<223> OTHER INFORMATION: exemplary sequence that can be used in making
      a nanoprobe.

<400> SEQUENCE: 86
attcagtctg caggaaggcc gactttagtt acaacatact aaatatatag ccagtaaggg    60
atccgatctc g                                                         71

<210> SEQ ID NO 87
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (20)..(21)
<223> OTHER INFORMATION: The linkeage between nucleotide 20 and 21 is
      [PEG18]-[PEG18]-[PEG18]
<220> FEATURE:
<221> NAME/KEY: misc_feature
<222> LOCATION: (40)..(40)
<223> OTHER INFORMATION: The nucleotide at position 40 is 3' linked to
      [PEG9]-NH-POOH-O-POOH-CH2-POOH-deoxyadenosine

<400> SEQUENCE: 87
gtacgtcgaa ttcaggagcg tactgccgag gacggaggcc                          40

<210> SEQ ID NO 88
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (20)..(21)
<223> OTHER INFORMATION: The linkeage between nucleotide 20 and 21 is
      [PEG18]-[PEG18]-[PEG18]
<220> FEATURE:
<221> NAME/KEY: misc_feature
<222> LOCATION: (40)..(40)
<223> OTHER INFORMATION: The nucleotide at position 40 is 3' linked to
      [PEG9]-NH-POOH-O-POOH-CH2-POOH-deoxythymidine

<400> SEQUENCE: 88
ggccttcctg cagactgaat cttacggcac ggagcgagag                          40

<210> SEQ ID NO 89
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: The nucleotide at position 1 is 5' linked to
      deoxyguanosine-POOH-CH2-POOH-O-POOH-NH-[PEG9]
<220> FEATURE:
<221> NAME/KEY: misc_feature
<222> LOCATION: (20)..(21)
<223> OTHER INFORMATION: The linkeage between nucleotide 20 and 21 is
      [PEG18]-[PEG18]-[PEG18]

<400> SEQUENCE: 89
gcgataagtc tagacgttcc agtcattaag cttcgcgctg                          40
```

```
<210> SEQ ID NO 90
<211> LENGTH: 40
<212> TYPE: DNA
<213> ORGANISM: Artificial sequence
<220> FEATURE:
<223> OTHER INFORMATION: exemplary sequence that can be used in making
      a nanoprobe.
<220> FEATURE:
<221> NAME/KEY: misc_feature
<222> LOCATION: (1)..(1)
<223> OTHER INFORMATION: The nucleotide at position 1 is 5' linked to
      deoxycytidine-POOH-CH2-POOH-O-POOH-NH-[PEG9]
<220> FEATURE:
<221> NAME/KEY: misc_feature
<222> LOCATION: (20)..(21)
<223> OTHER INFORMATION: The linkeage between nucleotide 20 and 21 is
      [PEG18]-[PEG18]-[PEG18]-

<400> SEQUENCE: 90
atgcatgaca ggcattatcg cgagatcgga tcccttactg                           40

<210> SEQ ID NO 91
<211> LENGTH: 20
<212> TYPE: DNA
<213> ORGANISM: Artificial sequence
<220> FEATURE:
<223> OTHER INFORMATION: quencher oligonucleotide
<220> FEATURE:
<221> NAME/KEY: misc_feature
<222> LOCATION: (20)..(20)
<223> OTHER INFORMATION: The nucleotide at position 20 is 3' linked to
      Iowa Black FQ

<400> SEQUENCE: 91
tctatacgga tccttacgct                                                 20

<210> SEQ ID NO 92
<211> LENGTH: 20
<212> TYPE: DNA
<213> ORGANISM: Artificial sequence
<220> FEATURE:
<223> OTHER INFORMATION: quencher oligonucleotide
<220> FEATURE:
<221> NAME/KEY: misc_feature
<222> LOCATION: (1)..(1)
<223> OTHER INFORMATION: The nucleotide at position 1 is 5' linked to
      Iowa Black RQ

<400> SEQUENCE: 92
gtctcgcgaa ttccggcctt                                                 20

<210> SEQ ID NO 93
<211> LENGTH: 20
<212> TYPE: DNA
<213> ORGANISM: Artificial sequence
<220> FEATURE:
<223> OTHER INFORMATION: quencher oligonucleotide
<220> FEATURE:
<221> NAME/KEY: misc_feature
<222> LOCATION: (20)..(20)
<223> OTHER INFORMATION: The nucleotide at position 20 is 3' linked to
      Black Hole Quencher

<400> SEQUENCE: 93
tctatacgga tccttacgct                                                 20

<210> SEQ ID NO 94
<211> LENGTH: 20
<212> TYPE: DNA
<213> ORGANISM: Artificial sequence
```

-continued

```
<220> FEATURE:
<223> OTHER INFORMATION: quencher oligonucleotide
<220> FEATURE:
<221> NAME/KEY: misc_feature
<222> LOCATION: (1)..(1)
<223> OTHER INFORMATION: The nucleotide at position 1 is 5' linked to
      Black Hole Quencher

<400> SEQUENCE: 94
gtctcgcgaa ttccggcctt                                              20

<210> SEQ ID NO 95
<211> LENGTH: 20
<212> TYPE: DNA
<213> ORGANISM: Artificial sequence
<220> FEATURE:
<223> OTHER INFORMATION: quencher oligonucleotide
<220> FEATURE:
<221> NAME/KEY: misc_feature
<222> LOCATION: (20)..(20)
<223> OTHER INFORMATION: The nucleotide at position 20 is 3' linked to
      Tamra

<400> SEQUENCE: 95
tctatacgga tccttacgct                                              20

<210> SEQ ID NO 96
<211> LENGTH: 52
<212> TYPE: DNA
<213> ORGANISM: Artificial sequence
<220> FEATURE:
<223> OTHER INFORMATION: oligonucleotide

<400> SEQUENCE: 96
cccggacgat attgaacaat ggttcactga agacccaggt ccagatgaag ct          52
```

NANOPROBES FOR DETECTION OR MODIFICATION OF MOLECULES

CROSS-REFERENCE TO RELATED APPLICATIONS

This application claims priority to U.S. Provisional Application Nos. 60/749,729 and 60/749,858 both filed Dec. 12, 2005 and herein incorporated by reference.

FIELD

This application relates to probes that can be used to detect or modify molecules, such as proteins and nucleic acid molecules, as well as methods of their use.

BACKGROUND

Several methods are currently available for detecting proteins and other molecules (such as nucleic acid molecules). For example, proteins can be detected using western blotting, flow cytometry, and ELISA methods. In addition, nucleic acids can be detected using Southern or northern blotting, microarrays, quantitative or non-quantitative PCR, chemical footprinting, and other methods known in the art. However, these methods require multiple steps and long detection times. Therefore, agents that permit detection with fewer steps and less time are needed. In addition, agents that permit detection in vivo are needed.

Methods are also currently available for modifying proteins and nucleic acid molecules, such as the use of antisense or siRNA molecules. However, agents having broader applications are needed.

SUMMARY

The disclosure is directed to molecular agents (referred to herein as nanoprobes) that can be used for detecting (such as quantitating) or modifying (such as destroying) one or more target molecules, such as biomolecules, organic molecules, and other molecules such as nylon. For example, the probes can be used to detect or modify a protein or a nucleic acid molecule. Although the application provides probes to use for particular biomolecules, one skilled in the art will recognize that the disclosed probes can be adapted to detect or modify any molecule of interest, for example by using particular functional groups.

In one example, a probe for a target biomolecule includes a molecular linker and first and second functional groups linked and spaced by the molecular linker. The functional groups are capable of interacting with one another or with the target biomolecule in a predetermined reaction, wherein the molecular linker links the first and second functional groups sufficiently spaced from one another such that the functional groups do not substantially interact in an absence of the target biomolecule. In particular examples, the molecular linker links the first and second functional groups sufficiently spaced a distance from one another to avoid substantial entanglement of the first and second functional groups in an absence of the target biomolecule. In some examples, the molecular linker (or at least a portion thereof) is of sufficient rigidity to reduce interaction of the first and second functional groups in the absence of the target biomolecule. In particular examples, the molecular linker is of a sufficient length to substantially avoid interaction of the first and second functional groups in the absence of the target biomolecule, and allow interaction of the first and second functional groups in the presence of the target biomolecule.

The molecular linker (or a portion thereof, such as a molecular rod that is part of the molecular linker) has a sufficient length in view of its flexibility to space the functional groups sufficiently apart to avoid the undesired interaction in the absence of the target biomolecule, but retain sufficient flexibility to allow the functional groups to interact with each other or the target when one or more functional groups bind to the target. For example, at least part of the linker can have a persistence length that permits at least a portion of the molecular linker to be of sufficient rigidity and length to reduce interaction of the first and second functional groups in the absence of the target biomolecule, and allow interaction of the first and second functional groups in the presence of the target biomolecule. In particular examples, the total length of the molecular linker is different than (such as greater or less than) the persistence length of one or more components that make up the linker, such as a double- or single-stranded nucleic acid molecule. However, in particular examples, the total length of the molecular linker does not exceed a length beyond which significant interaction occurs between the first and second functional groups in the absence of the target biomolecule, while allowing significant interaction of the first and second functional groups in the presence of the target biomolecule. Such interactions can be measured using methods known in the art, for example by measuring acceptor emission fluorescence when one functional group includes a donor fluorophore and one or more other functional groups include a corresponding acceptor fluorophore of a FRET pair. In other examples, a functional group is substantially maintained at a distance of at least twice the Förster radius (such as a Förster radius of 22 to 90 Å) from the other functional group in the absence of the target.

Persistence length (lp) is the average local conformation for a linear chain, which reflects the sum of the average projections of all chain segments on a direction described by a given segment. Therefore, persistence length is a measure of the rigidity or stiffness of a polymer chain. In particular examples, persistence length is the degree of bending (and hence the effective stiffness of the chain) which, in effect, measures the contour distance over which there occurs, on the average, a 68.40° bend. Therefore, the persistence length will vary depending on the composition of the molecular linker. For example, the persistence length for a double-stranded DNA (dsDNA) molecule will differ from that of a single-stranded DNA (ssDNA) molecule and from polyethylene glycol (PEG). In particular examples, dsDNA has a persistence length of about 400-500 Å, and dsRNA has a persistence length of 700-750 Å, for example at an ionic strength of about 0.2 M and at a temperature of 20° C. In particular examples, ssDNA has a persistence length of about 40 Å (for example at 20° C.) (Clossey and Carlon, *Phys. Rev. E. Stat. Nonlin. Soft. Matter. Phys.* 68(6 Pt 1):061911, 2003). In particular examples, PEG has a persistence length of about 3.8 Å.

Particular examples of molecular linkers include, but are not limited to, tethers, molecular rods, or combinations thereof. For example, the molecular linker of sufficient rigidity can include a molecular rod, for example a molecular rod composed of a double-stranded DNA molecule (dsDNA). In some examples, the molecular linker of sufficient rigidity includes multiple molecular rods linked by tethers, or multiple tethers linked by molecular rods. One particular example of a tether is a molecule composed of (or in some examples consisting of) polyethylene glycol (PEG).

The functional groups include molecules that can interact with one another or with the target biomolecule (or both) to provide a predetermined reaction, such as a detectable signal or a modification of a target biomolecule. The functional groups can be linked in a spatially separated orientation by a molecular linker so that the functional groups do not interact to provide the reaction in the absence of the target molecule. However, the molecular linker permits the functional groups, under predetermined conditions, to be brought into sufficient proximity with one another to interact and produce a predetermined reaction, such as a detectable signal or modification of a target biomolecule to which the probe binds or hybridizes. For example, the functional groups can include a targeting moiety (such as an antibody, protein, or nucleic acid probe) that binds to one or more sites on the target biomolecule to bring the functional groups in sufficient proximity to one another (or in sufficient proximity to the target biomolecule) for the interaction to occur. In another example, the functional groups can include an activatable moiety, such as a labeling moiety or a biomolecule modifying moiety (such as a proteinase or RNase). For example, at least one of the labeling moieties can be activated when brought into sufficient proximity to another labeling moiety, such as the excitation of an acceptor fluorophore labeling moiety by a donor fluorophore labeling moiety when the donor and acceptor are in sufficient proximity with one another. However, the activatable moiety can have biological activity in the absence of the interaction of the functional group with the target biomolecule, but have increased biological activity towards the target biomolecule when the functional groups are in sufficient proximity with the target biomolecule. In particular examples, a functional group includes both a targeting moiety and an activatable moiety.

Particular examples of functional groups include, but are not limited to, targeting agents (such as nucleic acid molecules, protein detection agents (for example antibodies), proteins, and nucleotides), as well as activation agents (such as a label or biomolecule modifying agent, for example a proteinase or nuclease), or combinations thereof. For example, a functional group can include a labeled antibody. One specific example of a label includes a FRET donor or a FRET acceptor fluorophore. Nanoprobes that include donor and acceptor fluorophore labeling moieties, for example in combination with a targeting moiety, will ideally produce little or no detectable background fluorescence emission from the acceptor fluorophore in the absence of the target biomolecule. The targeting moieties are selected to recognize and bind selectively or substantially only to targets of the biomolecule that bring the labeling (or other activatable) moieties into sufficient proximity for the targeting reaction to occur and signal the presence of the biomolecule. In the presence of the biomolecule, one or more of the other functional groups (such as antibodies or nucleic acid molecules) interact with the target biomolecule, which brings the donor and acceptor fluorophore into sufficient proximity such that the resonance with the donor fluorophore can excite the acceptor fluorophore, thereby resulting in an acceptor fluorophore emission spectrum or decrease in donor emission that can be detected.

Also provided are methods of using the nanoprobes, for example to detect or modify a biomolecule, or both. For example, methods are provided for using a nanoprobe to treat a subject having a disease that could be treated by decreasing the activity or expression of the target biomolecule. In a particular example, methods are providing for using a nanoprobe to sequence a sample nucleic acid molecule.

The foregoing and other features and advantages of the disclosure will become more apparent from the following detailed description of a several examples which proceeds with reference to the accompanying figures.

BRIEF DESCRIPTION OF THE FIGURES

FIG. 2A is a schematic drawing showing an exemplary nanoprobe that can be used to detect a DNA binding protein.

FIG. 2B is a schematic drawing showing binding of the exemplary nanoprobe of FIG. 1A to a target DNA binding protein, thereby generating a detectable signal.

FIG. 3A is a schematic drawing showing an exemplary nanoprobe that can be used to detect an antigenic compound, such as a protein.

FIG. 3B is a schematic drawing showing binding of the exemplary nanoprobe of FIG. 2A to a target antigenic compound, thereby generating a detectable signal.

FIG. 19 is a schematic drawing showing a nanoprobe attached to a surface.

FIG. 20 is a schematic drawing showing a nanoprobe that includes a non-specific targeting moiety (such as dodecyl sulfate) and a specific targeting moiety (such as an antibody) that can be used to detect a target protein.

SEQUENCE LISTING

The nucleic acid sequences listed in the accompanying sequence listing are shown using standard letter abbreviations for nucleotide bases. In particular examples, only one strand of a nucleic acid sequence is shown, but the complementary strand is understood as included by any reference to the displayed strand (for example in the case of a dsDNA molecular rod).

SEQ ID NOS: 1-4 are exemplary nucleic acid sequences that include a p53 binding site.

SEQ ID NO: 5 is an exemplary molecular rod sequence.

Figure 4A:
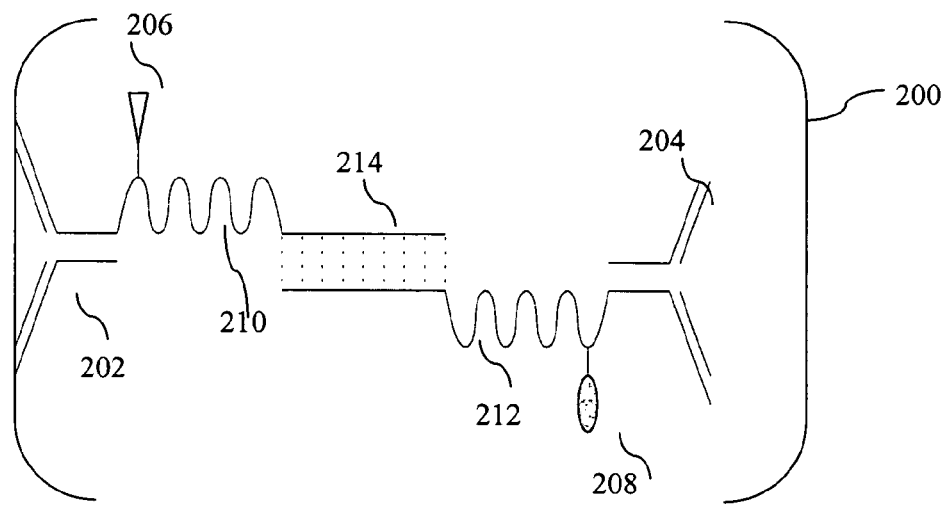
FIG. 4A is a schematic drawing showing an exemplary nanoprobe, which can be used to detect an antigenic compound, that further includes a molecular rod.

SEQ ID NOS: 6 and 7 are exemplary sequences that can be used to generate the nanoprobe shown in FIG. 4A.

Figure 5A:
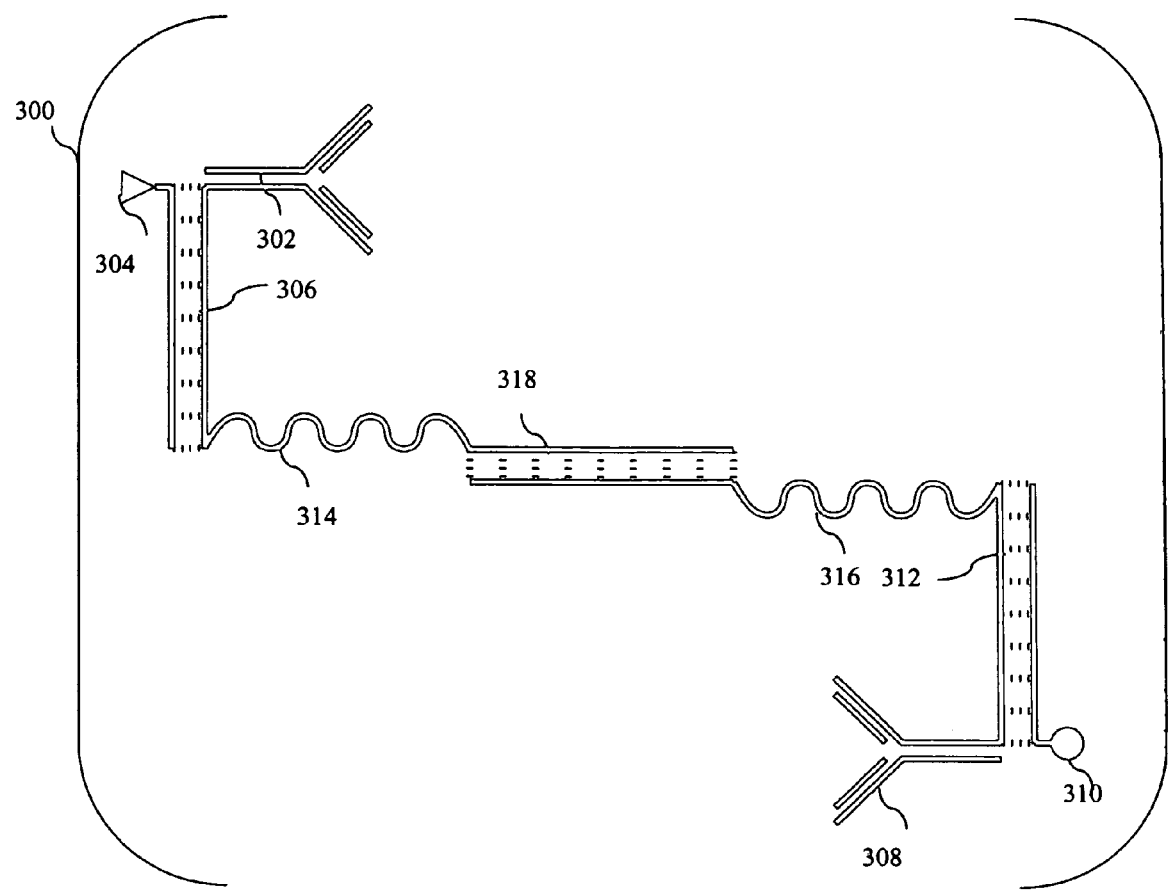
FIG. 5A is a schematic drawing showing an exemplary nanoprobe that includes multiple tethers and a molecular rod, which can be used to detect an antigenic compound.

SEQ ID NOS: 8-11 are exemplary sequences that can be used to generate the nanoprobe shown in FIG. 5A.

SEQ ID NO: 12 is an exemplary target nucleic acid sequence.

Figure 12A:
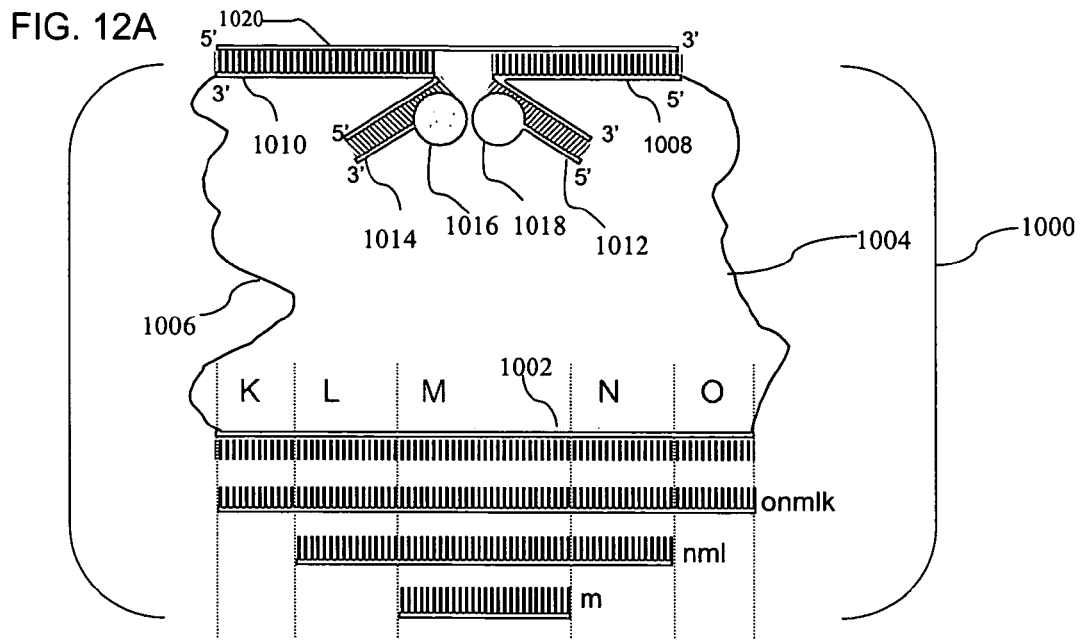
FIG. 12A is a schematic drawing showing an exemplary nanoprobe that includes antisense and fluorophore functional groups, which can be used to detect a target mRNA molecule.

SEQ ID NOS: 13-18 are exemplary sequences that can be used to generate the nanoprobe shown in FIG. 12A.

SEQ ID NOS: 16-18 are nucleic acid sequences that will specifically hybridize to a portion of SEQ ID NO: 12 to form different sized molecular rods (FIG. 12A, 1002).

Figure 14A:
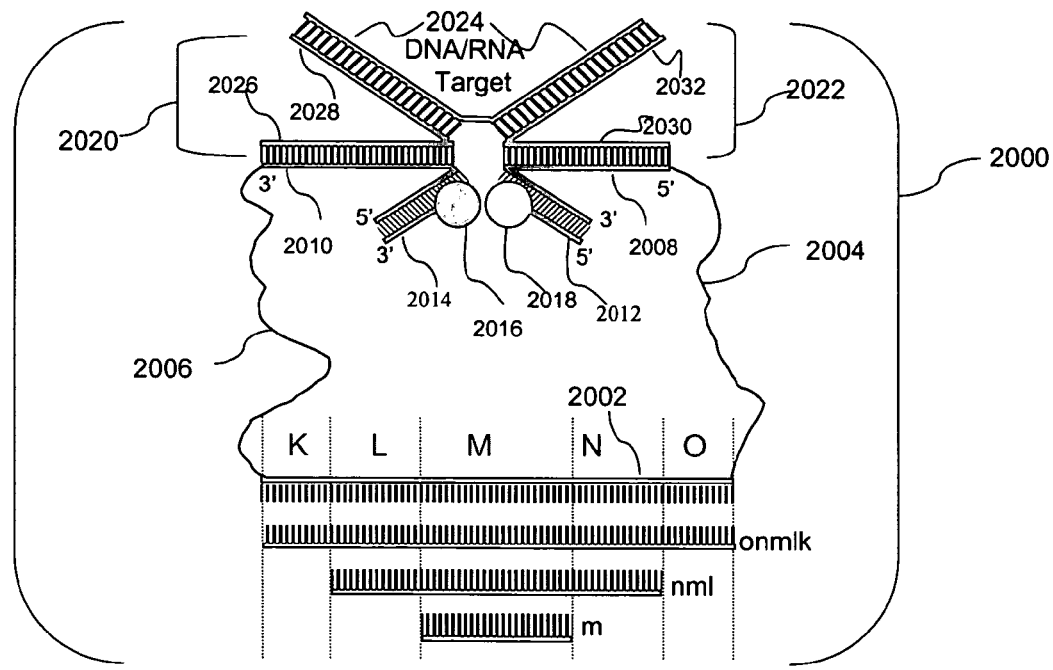
FIG. 14A is a schematic drawing showing an exemplary universal nanoprobe that includes antisense and fluorophore functional groups, which can be used to detect a target nucleic acid molecule.

SEQ ID NOS: 13-18 and 19-24 are exemplary sequences that can be used to generate the nanoprobe shown in FIG. 14A.

SEQ ID NO: 25 is an exemplary target nucleic acid sequence.

Figure 7:
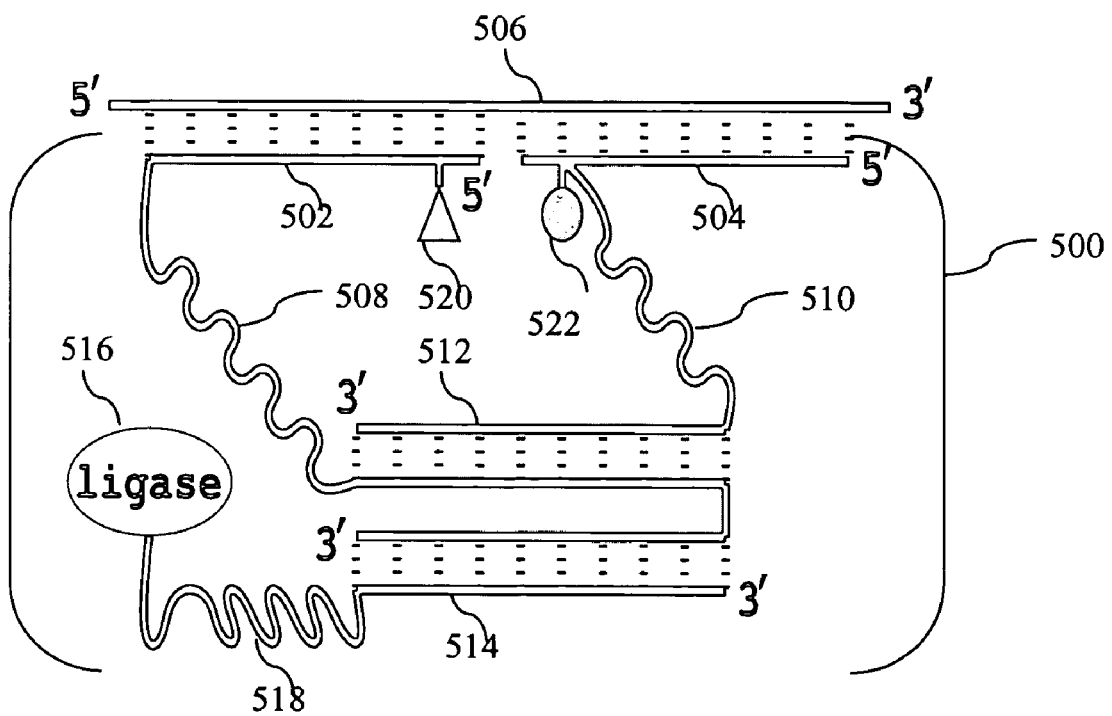
FIG. 7 is a schematic drawing showing an exemplary mRNA nanoprobe, which can be used to detect a target mRNA molecule, that includes antisense functional groups and a ligase. The ligase can "seal" the probe so that even if the target RNA has been destroyed or dissociates from the probe, the signal from the labeling moiety will continue.

SEQ ID NOS: 26-28 are exemplary sequences that can be used to generate the nanoprobe shown in FIG. 7.

SEQ ID NOS: 29-38 are exemplary target sequences that can be detected with the antisense sequence shown in SEQ ID NOS: 39-48, respectively.

Figure 11:
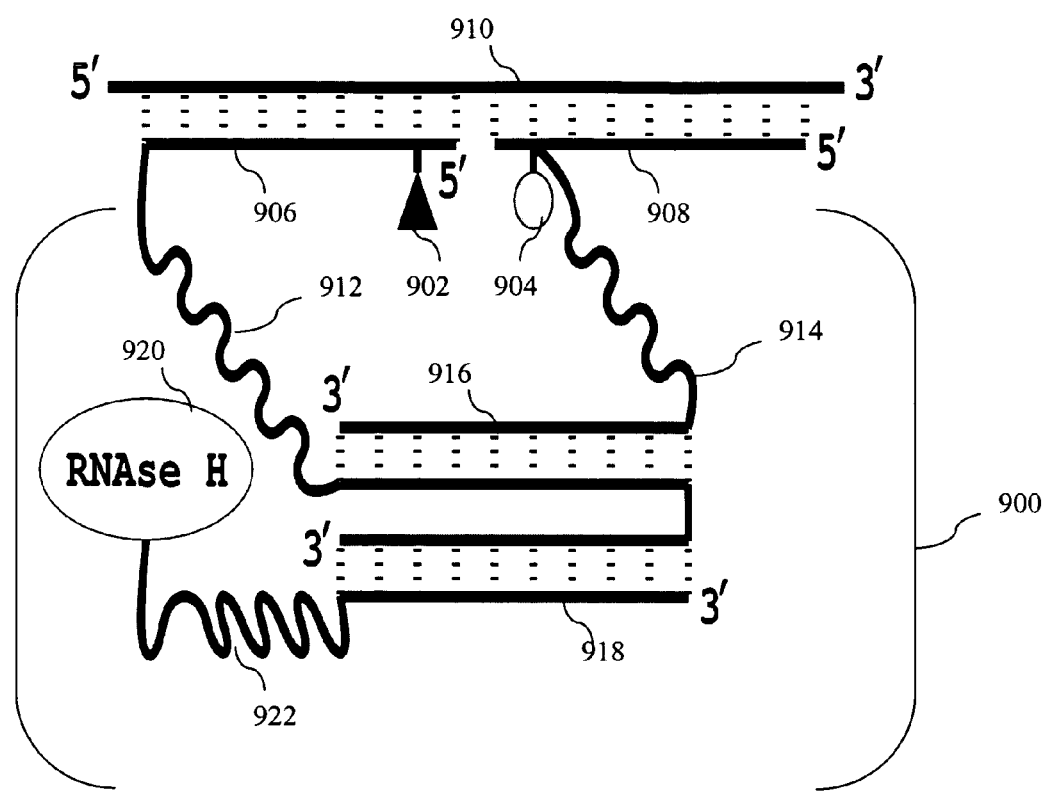
FIG. 11 is a schematic drawing showing an exemplary nanoprobe that includes antisense DNA and RNase H functional groups, which can be used to quantitate a target mRNA molecule.

SEQ ID NOS: 26-27 and 49 are sequences that can be used to generate the probe shown in FIG. 11.

SEQ ID NOS: 50-57 are exemplary DNA binding target sequences that can be detected with the sequence shown in SEQ ID NOS: 58-61, respectively.

Figure 10A:
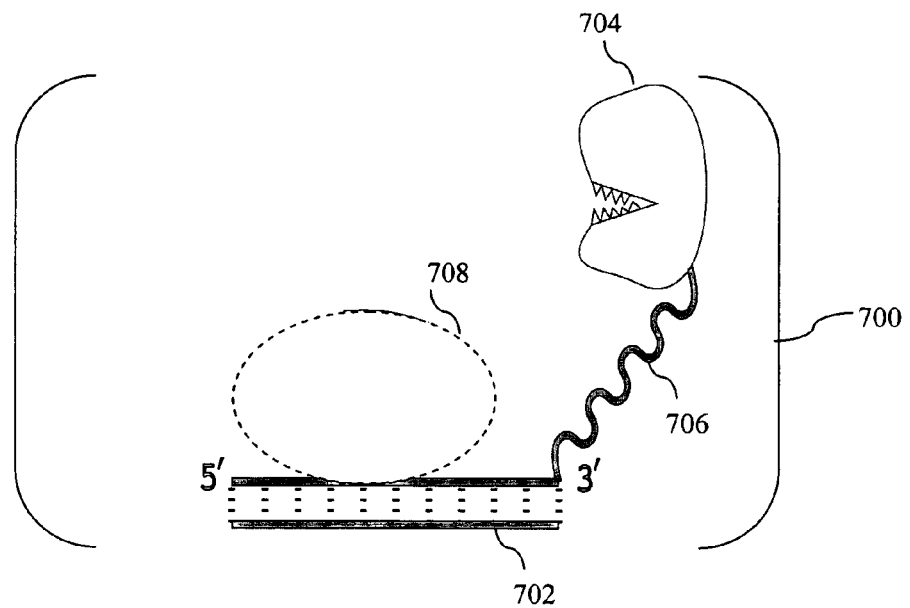
FIG. 10A is a schematic drawing showing an exemplary nanoprobe that includes a DNA binding region and proteinase K functional groups, which can be used to cleave a DNA binding protein.
Figure 10B:
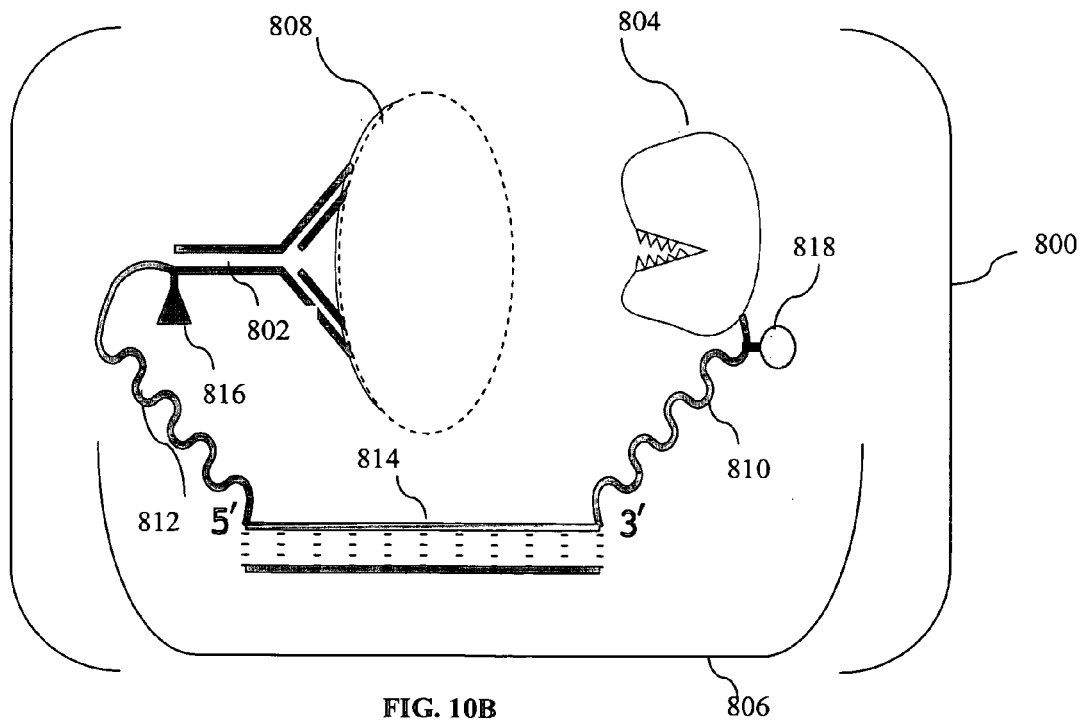
FIG. 10B is a schematic drawing showing an exemplary nanoprobe that includes a protein binding agent and proteinase K functional groups, which can be used to cleave a target protein.

SEQ ID NO: 62 is a sequence that can be used to generate the nanoprobe shown in FIG. 10B.

Figure 8A:
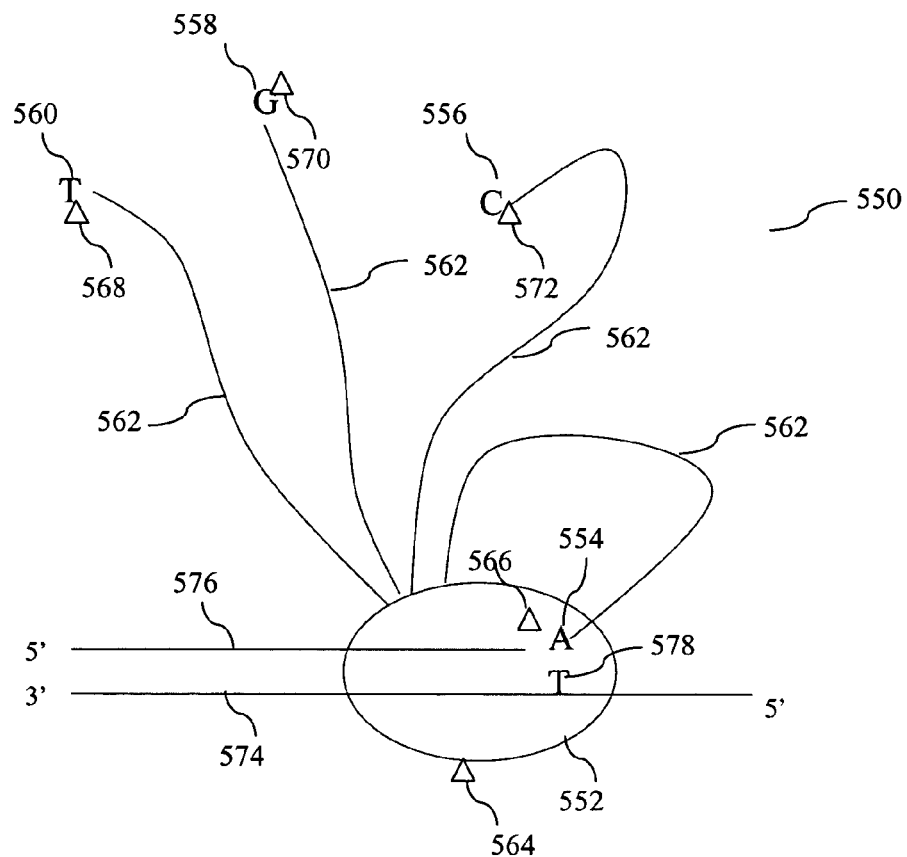
FIGS. 8A-C are schematic drawings showing an exemplary nanoprobes that can be used to sequence a nucleic acid molecule.
Figure 8B:
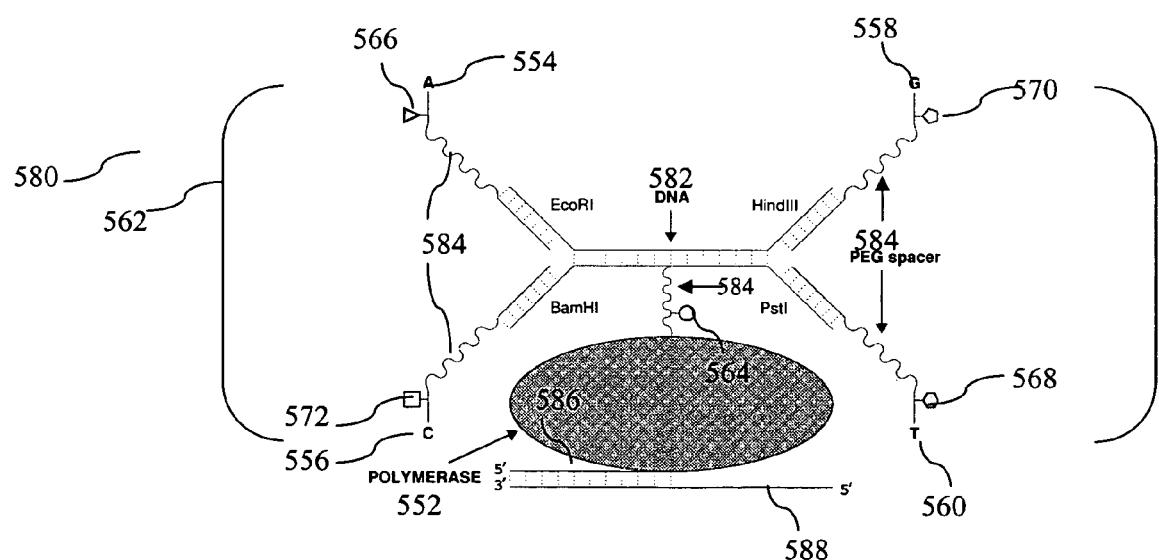
Figure 8C:
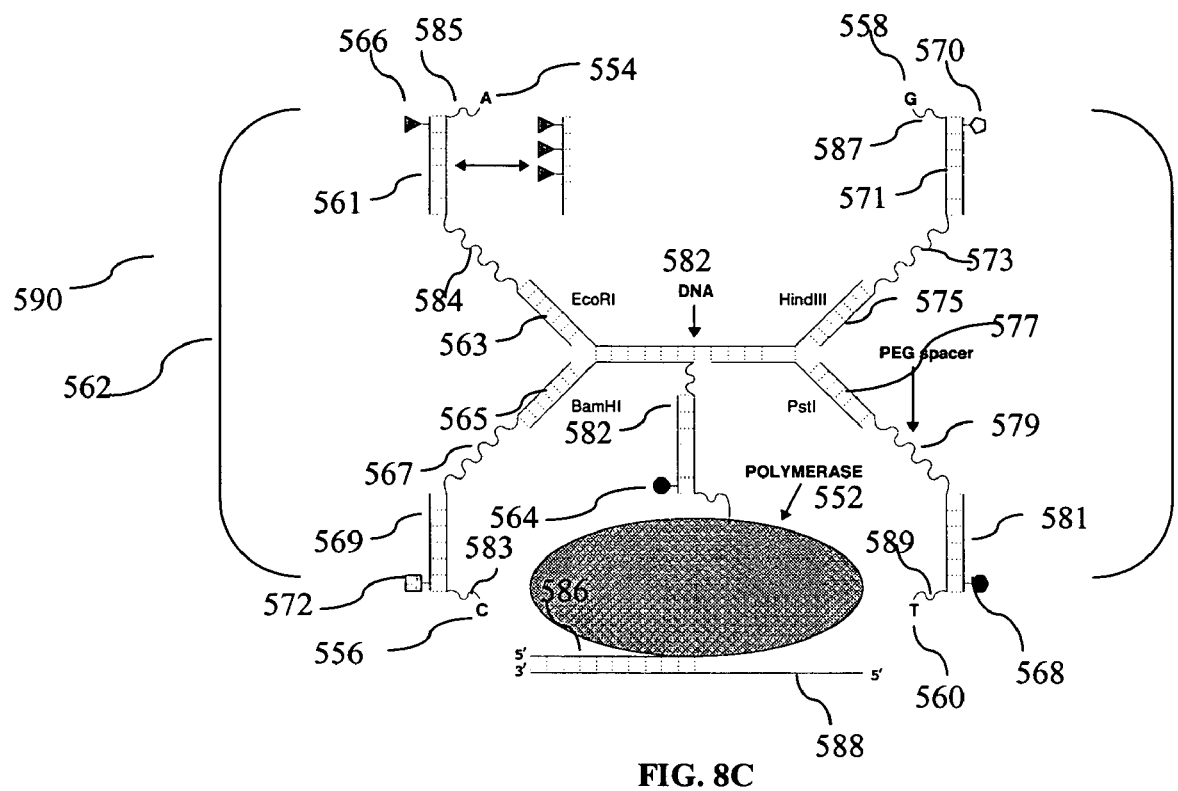

SEQ ID NOS: 63-90 are sequences that can be used to generate the nanoprobe shown in FIG. 8C.

SEQ ID NOS: 91-95 are exemplary quencher-containing oligonucleotides.

SEQ ID NO: 96 is an exemplary target p53 nucleic acid sequence.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. For example, reference to "a tether" includes one or a plurality of such tethers, and reference to "an antibody" includes reference to one or more antibodies and equivalents thereof known to those skilled in the art, and so forth. The term "or" refers to a single element of stated alternative elements or a combination of two or more elements, unless the context clearly indicates otherwise. For example, the phrase "detecting or modifying" refers to detecting, modifying, or a combination of both detecting and modifying.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features and advantages of the disclosure are apparent from the following detailed description and the claims.

Å angstrom
dsDNA double-stranded DNA
FRET Förster resonance energy transfer
GFP green fluorescent protein
LNA locked nucleic acid
PEG polyethylene glycol
PNA peptide nucleic acid
RT reverse transcriptase
ssDNA single-stranded DNA Acceptor fluorophore: Compounds which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher), than the maximum absorbance wavelength of the donor fluorophore, and have a fluorescence emission maximum at a wavelength ranging from about 400 to 900 nm. Acceptor fluorophores have an excitation spectrum which overlaps with the emission of the donor fluorophore, such that energy emitted by the donor can excite the acceptor. Ideally, an acceptor fluorophore is capable of being attached to the disclosed nanoprobes.

Exemplary acceptor fluorophores include, but are not limited to, rhodamine and its derivatives (such as N,N,N',N'-tetramethyl-6-carboxyrhodamine (TAMRA), 6-carboxy-X-rhodamine (ROX)), fluorescein derivatives (such as 5-carboxyfluorescein (FAM) and 2'7'-dimethoxy-4'5'-dichloro-6-carboxyfluorescein (JOE)), green fluorescent protein (GFP), BODIPY (4,4-difluoro-4-bora-3a,4a-diaza-s-indacene) and cyanine dyes.

In a particular example, an acceptor fluorophore is a dark quencher, such as, Dabcyl, Black Hole Quenchers™ from Glen Research, Eclipse™ Dark Quencher from Epoch Biosciences, Iowa Black™ from Integrated DNA Technologies. In such an example, instead of detecting an increase in emission signal from the acceptor fluorophore when in sufficient proximity to the donor fluorophore, a decrease in the emission signal from the donor fluorophore can be detected when in sufficient proximity to the quencher.

Activating or activatable moiety: A component of the functional group that acts on the target or with another functional group. For example, if the target is a protein, the activating moiety may be a protease. In another example, the activating moiety permits detection of the target biomolecule, for example a label moiety.

Administration: To provide or give a subject an agent, such as composition which includes the agent, by any effective route. In particular examples the agent includes one or more of the disclosed nanoprobes, alone or in the presence of a pharmaceutically acceptable carrier or other therapeutic agents. Exemplary routes of administration include, but are not limited to, oral, injection (such as subcutaneous, intramuscular, intradermal, intraperitoneal, and intravenous), sublingual, rectal, transdermal, intranasal, and inhalation routes.

Antibody: Immunoglobulin (Ig) molecules and immunologically active portions of Ig molecules, such as molecules that contain an antigen binding site which specifically binds (immunoreacts with) an antigen. Monoclonal and polyclonal immunoglobulin, as well as immunologically effective portions ("fragments") thereof, are encompassed by the disclosure. Antibodies can be used as functional groups in the disclosed nanoprobes.

An exemplary immunoglobulin is IgG. Naturally occurring IgG includes four polypeptide chains, two heavy chains and two light chains inter-connected by disulfide bonds. However, the antigen-binding function of an antibody can be performed by fragments of a naturally occurring antibody. Thus, these antigen-binding fragments are also intended to be designated by the term "antibody". Examples of binding fragments encompassed within the term antibody include (i) an Fab fragment that includes the variable light (VL), variable heavy (VH), constant light (CL) and constant heavy (CH1) domains; (ii) an Fd fragment that includes the VH and CH1 domains; (iii) an Fv fragment that includes the VL and VH domains of a single arm of an antibody, (iv) a dAb fragment that consists of a VH domain; and (v) an F(ab')$_2$ fragment, a bivalent fragment that includes two Fab fragments linked by a disulfide bridge at the hinge region.

In a particular example, an antibody is a humanized antibody (or immunologically effective portion thereof) or a chimeric antibody. Another particular example of an antibody is a nanobody (antibodies from camelids). Nanobodies have a heavy chain equivalent from which single-domain antibody fragments can be obtained, but not a light chain.

Antisense: Molecules that are specifically hybridizable (for example under highly stringent hybridization conditions) or specifically complementary to either RNA or the plus strand of DNA, for example a target mRNA or DNA sequence. In a particular example, one or more antisense molecules include one or more of the functional groups of the disclosed nanoprobes. Antisense molecules ideally contain a sufficient number of nucleotides to permit a specific interaction with a target nucleic acid sequence.

In particular examples, an antisense molecule is of a length that the melting temperature of the antisense:nucleic acid molecule hybrid formed is greater than about 45° C. For example, 20 base pairs provides a melting temperature of about 60° C. Therefore, at reaction temperatures of 25-45° C., the antisense:nucleic acid molecule hybrid formed would not sufficiently separate. Therefore, in particular examples, an antisense molecule includes at least 10 nucleotides, such as at least 12, at least 15, at least 20, at least 30, at least 40, or at least 50 nucleotides, for example 10-100 nucleotides (such as 10-50, 20-40, or 20-30 nucleotides).

Binding: An association between two or more molecules, such as the formation of a complex. Generally, the stronger the binding of the molecules in a complex, the slower their rate of dissociation. Specific binding refers to a preferential binding between an agent and a target.

Particular examples of specific binding include, but are not limited to, hybridization of one nucleic acid molecule to a complementary nucleic acid molecule, the association of an antibody with a peptide or other antigen, or the association of a protein with a target protein or target nucleic acid molecule.

In a particular example, a protein is known to bind to another protein or another biomolecule if a sufficient amount of the protein forms chemical bonds to the protein or other biomolecule, for example a sufficient amount to permit detection of that binding, such as detection using the disclosed nanoprobes.

In one example, an oligonucleotide molecule (such as an antisense molecule) is observed to bind to a target nucleic acid molecule if a sufficient amount of the oligonucleotide molecule forms base pairs or is hybridized to its target nucleic acid molecule to permit detection of that binding, for example detection using the disclosed nanoprobes. The binding between an oligonucleotide and its target nucleic acid molecule is frequently characterized by the temperature ($T_m$) at which 50% of the oligonucleotide is melted from its target. A higher ($T_m$) means a stronger or more stable complex relative to a complex with a lower ($T_m$).

In a particular example, binding is assessed by detecting labels present on the nanoprobe. For example, the fluorescent signal generated following the interaction of donor and acceptor fluorophores can be measured as an indication of binding between one or more functional groups on a nanoprobe and one or more target biomolecules.

In a particular example, an antibody specifically binds to a target biomolecule if the antibody specifically immunoreacts with the target biomolecule. Specific binding is typically determined from the reference point of the ability of the antibody to differentially bind the target biomolecule and an unrelated biomolecule, and therefore distinguish between two different biomolecules.

Biomolecule: An organic molecule, such as a macromolecule, present in living organisms, such as a mammal. Particular examples of biomolecules include, but are not limited to, proteins, nucleic acid molecules (such as DNA and RNA molecules), saccharides, vitamins, carbohydrates and lipids.

Detect: To determine if an agent is present or absent. In some examples this can further include quantification. For example, use of the disclosed nanoprobes in particular examples permits detection of one or more biomolecules in a sample. In particular examples, an emission signal from an acceptor fluorophore (such as the increase in the signal) is detected. In other particular examples, the emission signal from the donor fluorophore (such as the decrease in the signal) is detected.

Detection can be in bulk, so that a macroscopic number of molecules (such as at least $10^{23}$ molecules) can be observed simultaneously. Detection can also include identification of signals from single molecules using microscopy and such techniques as total internal reflection to reduce background noise. The spectra of individual molecules can be obtained by these techniques (Ha et al., *Proc. Natl. Acad. Sci. USA.* 93:6264-8, 1996).

Donor Fluorophore: Fluorophores or luminescent molecules capable of transferring energy to an acceptor fluorophore, thereby generating a detectable fluorescent signal. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$. A variety of compounds can be employed as donor fluorescent components, including fluorescein (and derivatives thereof), rhodamine (and derivatives thereof), GFP, phycoerythrin, BODIPY, DAPI (4',6-diamidino-2-phenylindole), Indo-1, coumarin, dansyl, and cyanine dyes. In particular examples, a donor fluorophore is a chemiluminescent molecule, such as aequorin.

DNA-binding protein: Any protein that can specifically bind to double- or single-stranded DNA. Examples include many proteins involved in the regulation of gene expression (including transcription factors), proteins involved in the packaging of DNA within the nucleus (such as histones), nucleic acid-dependent polymerases involved in DNA replication and transcription, or any of many accessory proteins which are involved in these processes. Other particular examples of DNA binding proteins include, but are not limited to p53, Tus (terminal utilization substance which binds to Ter, the terminus region in *E. coli*), Fis (factor for inversion stimulation which controls many genetic systems in *E. coli*), Lambda repressor, and Lac repressor.

Emission signal: The light of a particular wavelength generated from a fluorophore after the fluorophore absorbs light at its excitation wavelengths.

Emission spectrum: The energy spectrum which results after a fluorophore is excited by a specific wavelength of light. Each fluorophore has a characteristic emission spectrum. In one example, individual fluorophores (or unique combinations of fluorophores) are attached to nucleotides and the emission spectra from the fluorophores provide a means for distinguishing between the different nucleotides.

Entangled: To be twisted together, for example in a tangled mass. In particular examples, entanglement of a nanoprobe would reduce or prevent the functional groups from interacting with one another or from interacting with a target biomolecule, in the presence of the target biomolecule. In other particular examples, entanglement of a nanoprobe results in an undesirable interaction between the functional groups, for example an interaction that prevents interaction with, modification of, or detection of the target biomolecule.

Excitation or excitation signal: The light of a particular wavelength necessary to excite a fluorophore to a state such that the fluorophore will emit a different, such as longer, wavelength of light.

Fluorophore: A chemical compound, which when excited by exposure to a particular stimulus such as a defined wavelength of light, emits light (fluoresces), for example at a different wavelength.

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules eliminates the need for an external source of electromagnetic radiation, such as a laser. Examples of chemiluminescent molecules include, but are not limited to, aequorin (Tsien, 1998, *Ann. Rev. Biochem.* 67:509).

Examples of particular fluorophores that can be used in the nanoprobes disclosed herein are provided in U.S. Pat. No. 5,866,366 to Nazarenko et al., such as 4-acetamido-4'-isothiocyanatostilbene-2,2'disulfonic acid, acridine and derivatives such as acridine and acridine isothiocyanate, 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron.RTM. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include thiol-reactive europium chelates which emit at approximately 617 nm (Heyduk and Heyduk, *Analyt. Biochem.* 248:216-27, 1997; *J. Biol. Chem.* 274:3315-22, 1999), as well as GFP, Lissamine™, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. In one example, the fluorophore is a large Stokes shift protein (see Kogure et al., *Nat. Biotech.* 24:577-81, 2006). Other fluorophores known to those skilled in the art can also be used, for example those available from Molecular Probes (Eugene, Oreg.).

In particular examples, a fluorophore is used as a donor fluorophore or as an acceptor fluorophore. Ideally, fluorophores have the ability to be attached to a nanoprobe component without sufficiently interfering with the ability of the nanoprobe to interact with the target biomolecule, are stable against photobleaching, and have high quantum efficiency. In examples where multiple acceptor fluorophores are used, for example on a single nanoprobe or for example on different nanoprobes that are used together, the fluorophores are advantageously selected to have distinguishable emission spectra, such that emission from one fluorophore (or combination of two or more fluorophores) is distinguishable from another fluorophore (or combination of two or more fluorophores).

Förster (or fluorescence) resonance energy transfer (FRET): A process in which an excited fluorophore (the donor) transfers its excited state energy to a lower-energy light absorbing molecule (the acceptor). This energy transfer is non-radiative, and due primarily to a dipole-dipole interaction between the donor and acceptor fluorophores. This energy can be passed over a distance, for example a limited distance such as 10-100 Å. FRET efficiency drops off according to $1/(1+(R/R0)^6)$ where R0 is the distance at which the FRET efficiency is 50%.

FRET pairs: Sets (such as pairs) of fluorophores that can engage in fluorescence resonance energy transfer (FRET). Examples of FRET pairs that can be used are listed below. However, one skilled in the art will recognize that numerous other combinations of fluorophores can be used.

FAM is most efficiently excited by light with a wavelength of 488 nm, emits light with a spectrum of 500 to 650 nm, and has an emission maximum of 525 nm. FAM is a suitable donor fluorophore for use with JOE, TAMRA, and ROX (all of which have their excitation maxima at 514 nm, and will not be significantly stimulated by the light that stimulates FAM).

The GFP mutant H9-40 (Tsien, 1998, *Ann. Rev. Biochem.* 67:509), which is excited at 399 nm and emits at 511 nm, can serve as a suitable donor fluorophore for use with BODIPY, fluorescein, rhodamine green and Oregon green. In addition, the fluorophores tetramethylrhodamine, Lissamine™, Texas Red and naphthofluorescein can be used as acceptor fluorophores with this GFP mutant.

The fluorophore 3-($\epsilon$-carboxy-pentyl)-3'-ethyl-5,5'-dimethyloxacarbocyanine (CYA) is maximally excited at 488 nm and can therefore serve as a donor fluorophore for rhodamine derivatives (such as R6G, TAMRA, and ROX) which can be used as acceptor fluorophores (see Hung et al., *Analytical Biochemistry*, 243:15-27, 1996). However, CYA and FAM are not examples of a good FRET pair, because both are excited maximally at the same wavelength (488 nm).

One of ordinary skill in the art can easily determine, using art-known techniques of spectrophotometry, which fluorophores will make suitable donor-acceptor FRET pairs. In addition, Grant et al. (*Biosens Bioelectron.* 16:231-7, 2001) provide particular examples of FRET pairs that can be used in the nanoprobes disclosed herein.

Functional group: Any agent that can be used to detect (such as quantitate) or modify (or both) a biomolecule. Particular examples include, but are not limited to, targeting moieties and activating moieties that are brought into activating proximity when the targeting moiety binds to the target biomolecule. The targeting moiety, for example, brings the activatable moiety into sufficient proximity to the target for the activatable moiety to act on the target (for example when the activatable moiety is a non-specific proteinase that is brought sufficiently close to a protein target biomolecule to cleave or degrade the target protein). In other examples, each of the functional groups includes a targeting moiety and an activating moiety, and the targeting moiety binds to the target at a distance that selectively activates the activatable moiety. For example, each functional group can include an antibody or probe that binds to the target, and each functional group can include a labeling moiety, such a member of a FRET donor and acceptor fluorophore pair, wherein the acceptor is activated by the donor to emit a fluorescent signal when the target protein binds and brings the FRET pair into sufficient proximity to emit a detectable characteristic signal from the acceptor.

Particular examples of targeting moieties include, but are not limited to, antibodies, proteins, nucleotides and nucleic acid molecules (such as DNA binding molecules, PNAs or LNAs). Particular examples of activating moieties include, but are not limited to, labels (such as fluorophores) and modifying agents (such as enzymes, for example nucleases, ligases, or proteases, and a crosslinkable group such as psoralen).

Green fluorescent protein (GFP): The source of fluorescent light emission in *Aequorea victoria*. As used herein, GFP refers to both the wild-type protein, and spectrally shifted mutants thereof, for example as described in Tsien, 1998, *Ann. Rev. Biochem.* 67:509 and in U.S. Pat. Nos. 5,777,079 and 5,625,048 to Tsien and Heim, herein incorporated by reference. In particular examples, GFP is excited using a laser. In other examples, GFP is excited using aequorin, for example using a GFP-aequorin fusion protein.

Hybridization: To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)

| Hybridization: | 5x SSC at 65° C. for 16 hours |
| --- | --- |
| Wash twice: | 2x SSC at room temperature (RT) for 15 minutes each |
| Wash twice: | 0.5x SSC at 65° C. for 20 minutes each |

High Stringency (Detects Sequences that Share at Least 80% Identity r)

| Hybridization: | 5x-6x SSC at 65° C.-70° C. for 16-20 hours |
| --- | --- |
| Wash twice: | 2x SSC at RT for 5-20 minutes each |
| Wash twice: | 1x SSC at 55° C.-70° C. for 30 minutes each |

Low Stringency (Detects Sequences that Share at Least 50% Identity)

| Hybridization: | 6x SSC at RT to 55° C. for 16-20 hours |
| --- | --- |
| Wash at least twice: | 2x-3x SSC at RT to 55° C. for 20-30 minutes each. |

20×SSC is 3.0 M NaCl/0.3 M trisodium citrate.

Label: An agent capable of detection, for example by spectrophotometry, flow cytometry, or microscopy. For example, one or more labels can be attached to a nanoprobe, thereby permitting detection of the target biomolecule. Exemplary labels include radioactive isotopes, fluorophores, ligands, chemiluminescent agents, enzymes, and combinations thereof.

Ligase: An enzyme that can catalyse the joining of two molecules ("ligation") by forming a new chemical bond. An exemplary ligase is DNA ligase, which can link two nucleic acid molecules by forming a phosphodiester bond between the two molecules.

Linker or molecular linker: A structure that joins one molecule to other, such as one functional group to another functional group, wherein one portion of the linker is operably linked to a first functional group, and wherein another portion of the linker is operably linked to two or more other functional groups. Particular examples of linkers that can be used in a nanoprobe include, but are not limited to, tethers, molecular rods, or combinations thereof.

Locked Nucleic Acid (LNA™): A bicyclic nucleic acid where a ribonucleoside is linked between the 2'-oxygen and the 4'-carbon atoms with a methylene unit. This link restricts the flexibility of the ribofuranose ring of the nucleotide analog and locks it into the rigid bicyclic N-type conformation. The LNA also induces adjacent bases to adopt a conformation of the more thermodynamically stable form of the A duplex.

LNA oligonucleotides can be synthesized by standard phosphoramidite chemistry using DNA-synthesizers. In addition, LNA can be mixed with DNA, RNA as well as other nucleic acid analogs. In particular examples, LNA includes a functional group, such as an acceptor fluorophore.

Luminescence Resonance Energy Transfer (LRET): A process similar to FRET, in which the donor molecule is itself a luminescent molecule, or is excited by a luminescent molecule, instead of for example by a laser. Using LRET can decrease the background fluorescence. In particular examples, a chemiluminescent molecule can be used to excite a donor fluorophore (such as GFP), without the need for an external source of electromagnetic radiation. In other examples, the luminescent molecule is the donor, wherein the excited resonance of the luminescent molecule excites one or more acceptor fluorophores.

An example of luminescent molecule that can be used includes, but is not limited to, aequorin. The bioluminescence from aequorin, which peaks at 470 nm, can be used to excite a donor GFP fluorophore (Tsien, 1998, *Ann. Rev. Biochem.* 67:509; Baubet et al., 2000, *Proc. Natl. Acad. Sci. U.S.A.*, 97:7260-5). GFP then excites an acceptor fluorophore disclosed herein. In this example, both aequorin and GFP can be attached to a nanoprobe.

Modify: To change an agent, for example to decrease the biological activity of a biomolecule. For example, use of the disclosed nanoprobes in particular examples permits modification (such as cleavage or ligation) of one or more biomolecules in a sample.

Nanoprobe or probe: A molecular device that can be used to detect or modify (for example cleave or ligate) a target biomolecule, such as a protein or nucleic acid molecule. In particular examples, a nanoprobe or probe includes one or more labels that permit detection of the probe, such as an acceptor and donor fluorophore pair.

Nucleic acid molecule (or sequence): A deoxyribonucleotide or ribonucleotide polymer including without limitation, cDNA, mRNA, genomic DNA, and synthetic (such as chemically synthesized) DNA or RNA. The nucleic acid molecule can be double stranded (ds) or single stranded (ss). Where single stranded, the nucleic acid molecule can be the sense strand or the antisense strand. Nucleic acid molecules can include natural nucleotides (such as A, T/U, C, and G), and can also include analogs of natural nucleotides.

Nucleotide: Includes, but is not limited to, a monomer that includes a base, such as a pyrimidine, purine, or synthetic analogs thereof, linked to a sugar and one or more phosphate groups. A set of bases linked to a peptide backbone, as in a peptide nucleic acid (PNA), can be used as a substitute for a nucleic acid molecule. A nucleotide is one monomer in a polynucleotide. A nucleotide sequence refers to the sequence of bases in an oligonucleotide.

Nucleotide analog: A nucleotide containing one or more modifications of the naturally occurring base, sugar, phosphate backbone, or combinations thereof. Such modifications can result in the inability of the nucleotide to be incorporated into a growing nucleic acid chain. A particular example includes a non-hydrolyzable nucleotide. Non-hydrolyzable nucleotides include mononucleotides and trinucleotides in which the oxygen between the alpha and beta phosphates has been replaced with nitrogen or carbon (Jena Bioscience). HIV-1 reverse transcriptase cannot hydrolyze dTTP with the oxygen between the alpha and beta phosphates replaced by nitrogen (Ma et al., *J. Med. Chem.*, 35: 1938-41, 1992).

A "type" of nucleotide analog refers to one of a set of nucleotide analogs that share a common characteristic that is to be detected. For example, the sets of nucleotide analogs can be divided into four types: A, T, C and G analogs (for DNA) or A, U, C and G analogs (for RNA). In this example, each type of nucleotide analog can be associated with a unique tag, such as one or more acceptor fluorophores, so as to be distinguishable from the other nucleotide analogs in the set (for example by fluorescent spectroscopy or by other optical means).

An exemplary nucleotide analog that can be used in place of "C" is a G-clamp (Glen Research). G-clamp is a tricyclic Aminoethyl-Phenoxazine 2'-deoxyCytidine analogue (AP-dC). The G-clamp is available as a phosphoramidite and so can be synthesized into DNA structures. Such an analog can be used in the nanoprobes provided herein (for example the dCTP 556 shown in FIG. 8A can be substituted with a G-clamp).

Oligonucleotide: A linear polynucleotide (such as DNA or RNA) sequence, for example of at least 6 nucleotides, for example at least 9, at least 15, at least 18, at least 24, at least 30, at least 50, at least 100, at least 200 or even at least 500 nucleotides long. In particular examples, an oligonucleotide is about 6-50 bases, for example about 10-25 bases, such as 12-20 bases.

An oligonucleotide can contain non-naturally occurring portions, such as altered sugar moieties or inter-sugar linkages, such as a phosphorothioate oligodeoxynucleotide. In particular examples, an oligonucleotide containing non-naturally occurring portions can bind to RNA or DNA, and include peptide nucleic acid (PNA) molecules.

Peptide Nucleic Acid (PNA): A class of informational molecules containing a neutral peptide-like backbone with nucleobases allowing it to hybridize to complementary RNA or DNA with higher affinity and specificity than conventional oligonucleotides. The structure of a PNA molecule is analogous with DNA, wherein the deoxyribose phosphate backbone has been replaced by a backbone similar to that found in peptides. In particular examples, PNA is resistant to nucleases and proteases. PNAs can include a functional group at the N(5)-terminus, such as a fluorophore (for example an acceptor fluorophore).

Persistence length (lp): The average local conformation for a linear chain, reflecting the sum of the average projections of all chain segments on a direction described by a given segment. In particular examples, persistence length is the degree of bending (and hence the effective stiffness of the chain) which, in effect, measures the contour distance over which there occurs, on the average, a 68.40° bend.

Polyethylene glycol (PEG): A polymer of ethylene compounds, $H(OCH_2CH_2)_nOH$. Pegylation is the act of adding a PEG structure to another molecule, for example, a functional molecule such as a targeting or activatable moiety. PEG is soluble in water, methanol, benzene, dichloromethane and is insoluble in diethyl ether and hexane.

Particular examples of PEG that can be used in the disclosed nanoprobes include, but are not limited to: 1-7 units of Spacer 18 (Integrated DNA Technologies, Coralville, Iowa), such as 3-5 units of Spacer 18, C3 Spacer phosphoramidite (such as 1-10 units), Spacer 9 (such as 1-10 units), PC (Photo-Cleavable) Spacer (such as 1-10 units), (all available from Integrated DNA Technologies). In other examples, lengths of PEG that can be used in the disclosed nanoprobes include, but are not limited to, 1 to 40 monomers of PEG.

Polymerase: An enzyme which synthesizes a nucleic acid strand complementary to a nucleic acid template. Examples of polymerases that can be used to sequence a nucleic acid molecule include, but are not limited to, the *E. coli* DNA polymerase I, specifically the Klenow fragment which has 3' to 5' exonuclease activity, Taq polymerase, reverse transcriptase (such as HIV-1 RT), *E. coli* RNA polymerase, and wheat germ RNA polymerase II.

The choice of polymerase is dependent on the nucleic acid to be sequenced. If the template is a single-stranded DNA molecule, a DNA-directed DNA or RNA polymerase can be used; if the template is a single-stranded RNA molecule, then a reverse transcriptase (such as an RNA-directed DNA polymerase) can be used.

Proteinase K: An endolytic protease that cleaves peptide bonds at the carboxylic sides of aliphatic, aromatic or hydrophobic amino acids. Proteinase K is classified as a serine protease. The smallest peptide to be hydrolyzed is a tetrapeptide. Proteinase K is commercially available, for example from Fermentas (Hanover, Md.; #EO0491).

Quantum dots: Engineered, inorganic semiconductor crystalline nanoparticles that fluoresce stably and possess a uniform surface area that can be chemically modified to attach biomolecules (such as one or more nanoprobes) to them. Although generally spherical, quantum dots attached to nanoprobes of the present disclosure can be of any shape (such a spherical, tubular, pyramidal, conical or cubical), but particularly suitable nanoparticles are spherical. The spherical surface provides a substantially smooth and predictably oriented surface for the attachment of specific binding agents such as antibodies, with the binders extending substantially radially outwardly from the surface of the sphere.

Generally, quantum dots can be prepared with relative monodispersity (for example, with the diameter of the core varying approximately less than 10% between quantum dots in the preparation), as has been described previously (Bawendi et al., *J. Am. Chem. Soc.* 115:8706, 1993). Quantum dots known in the art have, for example, a core selected from the group consisting of CdSe, CdS, and CdTe (collectively referred to as "CdX").

Recombinant: A recombinant nucleic acid or protein sequence is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acid or protein sequences, for example by genetic engineering techniques. In particular examples, a molecular rod composed of a dsDNA is a recombinant molecule.

RNase H (Ribonuclease H): A ribonuclease (EC 3.1.26.4) that cleaves the 3'-O-P-bond of RNA in a DNA/RNA duplex to produce 3'-hydroxyl and 5'-phosphate terminated products. RNAse H does not degrade DNA or unhybridized RNA. To terminate the reaction, a chelator, such as EDTA, can be added to sequester the required metal ions in the reaction mixture.

Members of the RNase H family can be found in nearly all organisms. RNase H proteins can be produced using commercially available clones (for example from the *E. coli* Genome Project, University of Wisconsin, Madison, Wis., such as clone pEKGb0214; from NEB, Ambion, and Roche). In one example, MuLV RNAse H is used for the nanoprobe (for example see Than and Crouch, *J. Biol. Chem.*, 272:22023-9, 1997).

Rod or molecular rod: A structure that can be included in a nanoprobe's molecular linker to increase the rigidity of a portion of the nanoprobe, thereby reducing the interaction of functional groups, labels (such as donor and acceptor fluorophores), or combinations thereof, in the absence of the target biomolecule. In addition, molecular rods are of a length that permits the functional groups, labels, or combinations thereof to interact in the presence of the target biomolecule.

In a particular example, a molecular rod present in a molecular linker has a length shorter than its persistence length. In the absence of the target biomolecule, the rod significantly reduces the interaction of the first and second functional groups joined by the molecular linker that contains the rod. In one example, a molecular rod consisting of dsDNA has a length of 10-140 nucleotides, which is shorter than the persistence length of dsDNA, about 150 nucleotides.

Exemplary molecular rods include, but are not limited to, dsDNA molecules, peptide nucleic acids (PNAs), carbon nanotubes, locked nucleic acid molecules (LNAs), a microtubule, a bacterium, a linear virus particle, virus tail fibers or other protein structures (such as protein components containing alpha helices or beta barrels or other protein structures, such as a leucine zipper structure). A molecular rod can be a portion of a three-dimensional molecular construct, such as a cube or octahedron built from DNA (for example see Seeman, *Sci. Am.* 290:64-9 and 72-5, 2004). In a particular example, a molecular rod is a dsDNA molecule of at least 10 nucleotides, at least 35 nucleotides, or 150 nucleotides or less, such as 10-150 nucleotides, 10-140 nucleotides, 20-100 nucleotides, 20-50 nucleotides, 20-40 nucleotides, 30-50 nucleotides, or about 20, 30, or 40 nucleotides.

Sample: Biological specimens such as samples containing biomolecules, such as nucleic acid molecules (for example genomic DNA, cDNA, RNA, or mRNA) or proteins. Exemplary samples are those containing cells or cell lysates from a subject, such as those present in peripheral blood (or a fraction thereof such as serum), urine, saliva, tissue biopsy, surgical specimen, fine needle aspirates, amniocentesis samples and autopsy material.

Signal: A detectable change or impulse in a physical property that provides information. In the context of the disclosed methods, examples include electromagnetic signals such as light, for example light of a particular quantity or wavelength. In certain examples the signal is the disappearance of a physical event, such as quenching of light.

Subject: Living multi-cellular vertebrate organisms, including human and veterinary subjects, such as cows, pigs, horses, dogs, cats, birds, reptiles, and fish.

Target biomolecule: A biomolecule (such as a nucleic acid molecule, protein, or antigenic compound) whose detection, modification (such as inactivation or ligation), quantitation, qualitative detection, or a combination thereof, is intended. The biomolecule need not be in a purified form. Various other biomolecules can also be present with the target biomolecule. For example, the target biomolecule can be a specific nucleic acid molecule or a protein in a cell (which can include host RNAs (such as mRNA), DNAs (such as genomic or cDNA), and proteins), the detection or modification of which is intended.

Targeting moiety: A functional group component that binds a functional group to the target biomolecule. Examples include antibodies that recognize protein targets, and nucleic acid molecules that bind to nucleic acid target sequences.

Tether: A structure that can be included in a nanoprobe to link one functional group to another, directly or indirectly. For example a tether can be used to directly link one functional group to another, such as a tether of 120 to 240 Å. In another example, one or more tethers, in combination with one or more molecular rods, are used to link one functional group to another. Ideally, the tether is a length that reduces the likelihood that the tether will tangle with itself or with other components of the nanoprobe, while still allowing the functional groups, labels, or combinations thereof to interact in the presence of the target biomolecule.

Exemplary tethers disclosed herein include water soluble long chain molecules, such as PEG, peptides (such as a peptide of at least 30 amino acids, for example at least 30 contiguous amino acids of the RecB protein 70-amino acid-long flexible tether connecting the helicase to the nuclease (Singleton et al., *Nature* 432:187-93, 2004)), sugar chains (such as 2000-14000 residues), abasic phosphodiester spacers (such as the IDT 5' dSpacer), carbohydrate chains (such as at least 10 sugar molecules), and polycaprolactone chains (such as at least 10 monomers). In a particular example, a tether is composed of PEG, for example a PEG length of about 23-600 Å, such as 23-400 Å, or 23-164 Å.

Therapeutically effective amount: An amount of an agent (alone or in combination with other therapeutically effective agents) sufficient to achieve a desired biological effect, for example an amount that is effective to decrease the activity of a target biomolecule by at least a desired amount. In a particular example, it is an amount of a nanoprobe disclosed herein that is effective to decrease the activity of a target biomolecule by at least 25%, at least 50%, at least 75%, or at least 90%, for example as compared to an amount of activity prior to treatment.

In some examples, it is an amount of a therapeutic nanoprobe (alone or in combination with other therapeutically effective agents) that can decrease the activity of a target biomolecule to improve signs or symptoms of a disease caused by activity or expression of a target biomolecule. An effective amount of a nanoprobe that decreases the activity of a target biomolecule can be administered in a single dose, or in several doses (for example daily, weekly, or monthly) during a course of treatment. However, the effective amount of agent may be dependent on the source of agent administered, the subject being treated, the severity and type of disease being treated, and the manner of administration.

Treating a disease: "Treatment" refers to a therapeutic intervention that ameliorates a sign or symptom of a disease or pathological condition, such as a sign or symptom of cancer. Treatment can also induce remission or cure of a condition, such as cancer. In particular examples, treatment includes preventing a disease, for example by inhibiting the full development of a disease, such as preventing development of cancer (for example preventing metastasis of the cancer). Prevention of a disease does not require a total absence of disease. For example, a decrease of at least 10%, at least 25% or at least 50% can be sufficient.

Under conditions sufficient for: A phrase that is used to describe any environment that permits the desired activity.

An example includes contacting a nanoprobe with a sample sufficient to allow the desired activity. In particular examples, the desired activity is the detection or modification of one or more target biomolecules in the sample. In other particular examples, the desired activity further includes quantitation of one or more target biomolecules in the sample.

Unique Emission Signal: An emission signal that conveys information about a specific event, such as the emission spectrum for a particular fluorophore, which can be distinguished from other signals (such as other emission spectrum signals). Examples in association with the disclosed methods include attaching one or more individual fluorophores or other labels to different types of nanoprobes, where each different type of nanoprobe (for example nanoprobes that are specific for different mutations of the same protein) has its own individual or own combination of signals (such as fluorophores that emit at different unique wavelengths). Each nanoprobe class will have a unique emission signal that in the examples is based on the fluorophore(s) present on that class of nanoprobe. This signal can be used to determine which nanoprobe is interacting with a target biomolecule. Similarly, by attaching one or more individual fluorophores or other labels to each type of nucleotide, each different type of nucleotide (A, T/U, C or G) has its own individual or own combination of signals (such as fluorophores that emit at different unique wavelengths). Each nucleotide class will have a unique emission signal that in the examples is based on the fluorophore(s) present on that class of nucleotide. This signal can be used to determine which type of nucleotide (A, T/U, C or G) will be added to a growing complementary strand of nucleic acid, and these signals in combination indicate the nucleic acid sequence.

A signal can be characterized not only by different wavelengths but also by different intensities at various wavelengths, to form a unique spectrum. In particular, two signals having the same set of wavelengths can be distinguished if they have some different intensities at particular wavelengths.

General Strategy

The disclosed nanoprobes include a linker that spaces functional groups. The linker has a combination of length and flexibility that substantially maintains the functional groups spaced a desired distance in the absence of the target biomolecule, but permits them to substantially interact in the presence of the target biomolecule. Each functional group can include a targeting moiety or an activating moiety (such as a labeling moiety), or combinations thereof. The following table illustrates some such combinations.

TABLE 1

Exemplary functional group combinations.

| Target | Functional group 1 | Functional Group 2 |
|---|---|---|
| Protein | Antibody/Donor* | Antibody/Acceptor |
| Protein | Antibody/Acceptor | Antibody/Donor |
| Protein | Antibody/Donor | Nucleic acid sequence/Acceptor |
| Protein | Antibody/Acceptor | Nucleic acid sequence/Donor |
| Protein | Antibody | Proteinase |
| Protein | Antibody/Acceptor | Proteinase/Donor |
| Protein | Antibody/Donor | Proteinase/Acceptor |
| Protein | Nucleic acid sequence | Proteinase |
| Protein | Nucleic acid sequence/Donor | Proteinase/Acceptor/Antibody |
| DNA | Nucleic acid probe | nuclease |
| DNA | Nucleic acid probe/donor | Nucleic acid probe/acceptor |
| DNA | Nucleic acid probe/acceptor | Nucleic acid probe/donor |
| DNA | Polymerase/donor | Non-hydrolyzable dNTPs/acceptors |
| RNA | Nucleic acid probe | RNase H |
| RNA | Nucleic acid probe/acceptor Nucleic acid probe/donor | RNase H |
| RNA | Nucleic acid probe/donor | Nucleic acid probe/acceptor |
| RNA | Nucleic acid probe/acceptor | Nucleic acid probe/donor |

*donor is a donor fluorophore, acceptor is an acceptor fluorophore

The multi-component nanoprobes need only to maintain potentially interacting components of the functional group outside of a minimum distance. Also, since the location of the molecular components can only be expressed in terms of statistical probabilities, it is understood that absences of interaction are not absolute but instead refer to restriction of dynamic molecular movements in a manner that reduces undesired interactions between functional groups to a desired level. Once the probe binds to a target molecule (for example by protein/antibody interaction or nucleic acid/nucleic acid hybridization) the flexibility of the linker is sufficient to permit the functional groups to interact (for example in a donor/acceptor fluorophore interaction) or the target and unbounded functional group to interact (for example in a protein/protein interaction). When each functional group includes a labeling moiety (such as a donor/acceptor) and targeting moiety (such as an antibody) the first targeting moiety binds to the target. With the first targeting moiety bound to the target at the first site, the second targeting moiety then has an increased statistical probability of interacting with the target at a preselected second site. With both targeting moieties bound to the target, the donor/acceptor moieties are maintained in sufficient proximity for a period of time that permits the donor/acceptor interaction to occur and emit a detectable signal (or result in quenching of a detectable signal).

Nanoprobes for Detection or Modification of a Biomolecule

The present disclosure provides nanoprobes for one or more target biomolecules. In particular examples, the disclosed nanoprobes are used in vitro, ex vivo, or even in vivo to detect or modify the target biomolecule. For example, one or more nanoprobes can be attached to a surface (such as a glass or plastic slide or a microarray surface), such as via a linker, a biological sample incubated with the surface, wherein detection of a signal from the nanoprobe indicates the presence or absence of a target molecule. The nanoprobes include two or more functional groups that are selected based on the target biomolecule. Particular examples of biomolecules that can be targeted include, but are not limited to, nucleic acid molecules (such as RNA or DNA molecules), antigenic compounds (such as an antigenic protein), as well as proteins.

In particular examples, nanoprobes provide benefits over currently available technologies, such as ELISA. For example, the nanoprobes can provide a rapid method of detecting or modifying a target biomolecule, are relatively inexpensive to use and manufacture, can be built using modular designs with interchangeable parts, and can permit measurement of several parameters simultaneously.

Figure 1A:
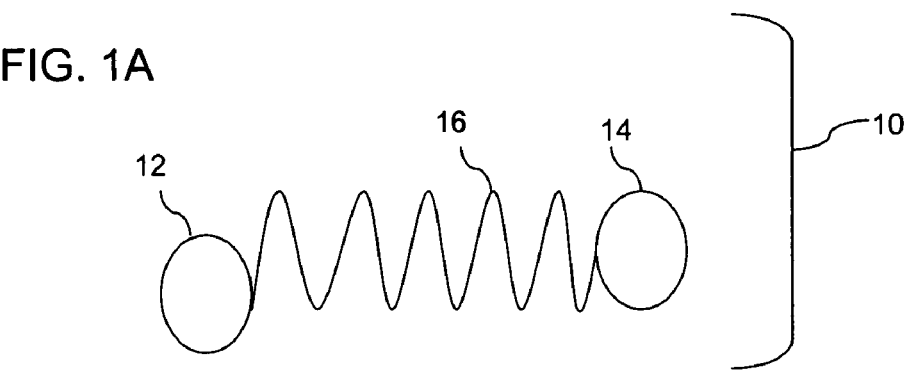
FIG. 1A is a schematic drawing showing an exemplary nanoprobe that includes functional groups linked by a tether.

One particular example of a probe for a target biomolecule includes a molecular linker and first and second functional groups linked and spaced by the molecular linker. For example, FIG. 1A shows a nanoprobe 10 that includes first and second functional groups 12, 14 that are linked and spaced by the molecular linker 16. The functional groups are capable of interacting with one another or with the target biomolecule in a predetermined reaction, wherein the molecular linker maintains the first and second functional groups sufficiently spaced from one another such that the functional groups do not substantially interact in an absence of the target biomolecule. In particular examples, they are spaced a distance from one another to avoid substantial entanglement of the first and second functional groups in an absence of the target biomolecule. However, in the presence of the target biomolecule, the molecular linker permits the first and second functional groups to sufficiently interact with one another or with the target biomolecule in the predetermined reaction. For example, in the presence of the target biomolecule the first and second functional groups attach to the target in sufficient proximity to permit the functional groups to interact and yield a signal (such as light) or a target modifying effect (such as target lysis or degradation).

As noted above, in particular examples the length of the molecular rod is one that maintains the first and second functional groups sufficiently spaced from one another such that the functional groups do not substantially interact in an absence of the target biomolecule.

Methods are known in the art for determining whether one functional group interacts with one or more other functional groups, for example in the presence or absence of a target molecule. In one example, to determine if a particular length molecular linker is appropriate, a probe of the present disclosure having a particular molecular linker length is generated using the methods disclosed herein. In particular examples, multiple probes are generated, each having a different molecular linker length. To identify lengths of molecular linkers that are suitable for use, a donor fluorophore is attached to one end of the molecular linker and an appropriate acceptor fluorophore is attached to the other end of the molecular linker. In particular examples, the probe includes a FRET pair. To determine if the ends of the molecular linkers are capable of interacting with one another, the molecular linker can be placed in a solution in the presence and absence of the target biomolecule, and acceptor emission fluorescence detected, for example by spectrophotometry or fluorescence microscopy. In particular examples, lengths of molecular linkers that only produce significant acceptor emission fluorescence (for example above a predetermined threshold) when the target biomolecule is present, and produce no more than background levels of acceptor emission fluorescence in the absence of the target biomolecule, can be used in the probes of the present disclosure. In contrast, in particular examples, lengths of molecular linkers that do not produce significant acceptor emission fluorescence when the target biomolecule is present, or produce levels of acceptor emission fluorescence that are significantly above background in the absence of the target biomolecule, are not used in the probes of the present disclosure. In some examples, the length of the molecular linker that produces a desirable result can vary depending on the particular FRET pair used. For example, the length of the molecular linker used if a GFP/fluorescein FRET pair is part of the probe, may be different than the length of the molecular linker used if an Alexa Fluor 430/BODIPY 630 FRET pair is part of the probe.

In particular examples, the molecular linker (or at least a portion thereof, such as a portion that includes a molecular rod) is of a sufficient rigidity to reduce interaction of the first and second functional groups in the absence of the target biomolecule. For example, a portion of the molecular linker can have a persistence length that permits that part of the molecular linker to be of sufficient rigidity to reduce the interaction of the first and second functional groups in the absence of the target biomolecule, while other portions of the molecular linker (such as a tether) allow interaction of the first and second functional groups (or interaction of one or more functional groups with the target biomolecule) in the presence of the target biomolecule.

The total length of the molecular linker can be the same or a different length than the persistence length for a particular component of the molecular linker, as long as the length differential is insufficient to yield undesired interaction of the functional groups. For example, if the molecular linker includes a molecular rod that has a particular persistence length, the molecular linker can be shorter or longer than that persistence length. For example, if the persistence length of dsDNA is greater than 150 nt, the total length of the linker can be greater than 150 nt, for example by having tethers or additional rods. Similarly, the linker can be shorter than 150 nt, for example by having a rod of 40 nt, and a tether of 2-4 or 3-4 PEG spacer 18 moieties. In addition, the molecular rod length itself can be shorter or greater than the persistence length of the polymer used to generate the molecular rod. In particular examples, a molecular linker includes a molecular rod, and the total length of the rod is shorter than the persistence length of the molecule composing the molecular rod (such as 0.1-times, 0.5-times, or 1-times the persistence length of the molecule composing the molecular rod). In yet other particular examples, the length of the linker can be greater or less than the persistence length of any one of its components. For example, for a molecular linker that includes a molecular rod, the total length of the molecular linker is not more than 5-times shorter or longer than the persistence length of the molecule composing the molecular rod (such as 1-5 times, 1-4 times, or 1-3 times the persistence length of the molecular linker that contains the molecular rod). In one example, the molecular rod is composed of dsDNA, which has a persistence length of 400-500 Å, and the length of the molecular rod is greater than 400-500 Å (such as 550-700 Å or 550-1000 Å) or shorter than the persistence length (such as 100-350 Å, for example 200-350 Å).

Those skilled in the art will recognize that at one persistence length the far end of a rod is often still substantially pointing in the same direction)(68.40°) as the original direction and that a rod of this length, and hence flexibility, can still provide a useful functional rigidity. Rods of lengths greater than the persistence length provide a further degree of flexibility that can be acceptable in some applications. In other applications a single linker can consist of a single molecule of a uniform kind (as 1000 by of dsDNA, which is substantially longer than the persistence length) wherein certain portions of that linker are sufficiently close (for example 40 bp) that they may act as molecular rods locally and provide nanoprobe functions locally, while longer portions of the linker are sufficiently far apart as to act as molecular tethers that allow the parts to come together or not depending on Brownian motion and the presence of target molecules that can be bound. Such a situation occurs when local transcription factors bind to DNA in essentially rigid positions relative to each other, while further pieces of DNA can 'loop' around to supply, for example, an enhancer, activator or repressor (as for example in the GalR binding sites of *E. coli*, Semsey et al., *Genes Dev.* 18:1898-907, 2004). Although such nanoprobe constructions are possible, in general the constructions described herein distinguish clearly between molecular rods as being not substantially larger than the persistence length and molecular tethers as being substantially longer than their corresponding persistence length. Unlike the dsDNA transcriptional control systems found in nature, generally in the nanoprobes described herein the molecular rods and tethers are constructed by connecting different kinds of molecules that have substantially different persistence lengths as for example dsDNA with PEG.

The persistence length will vary depending on the composition. For example, the persistence length for a double-stranded DNA (dsDNA) molecule differs from that of a single-stranded DNA (ssDNA) molecule and from polyethylene glycol (PEG). For example, dsDNA has a persistence length of 400-500 Å. In particular examples, ssDNA has a persistence length of about 40 Å. In particular examples, PEG has a persistence length of about 3.8±0.02 Å (Kienberger et al., *Single Molecules* 1:123-8, 2000).

To substantially avoid interaction of the first and second functional groups in the absence of the target biomolecule, and allow interaction of the first and second functional groups in the presence of the target biomolecule, the length of the linker is at least sufficient to maintain the functional groups spaced at least the Forster radius for the particular donor and acceptor fluorophores used, such as a distance of 22 to 90 Å. In some examples, the length of the linker is sufficient to separate charges on the functional groups, such as a distance of 10 to 1000 Å. In particular examples, the total length of the molecular linker is about 10 to 500 Å, such as 10 to 300 Å, 10 to 200 Å, 20 to 200 Å, 20 to 187 Å, 20 to 150 Å, 60 to 120 Å, or 60 to 200 Å.

Figure 1B:
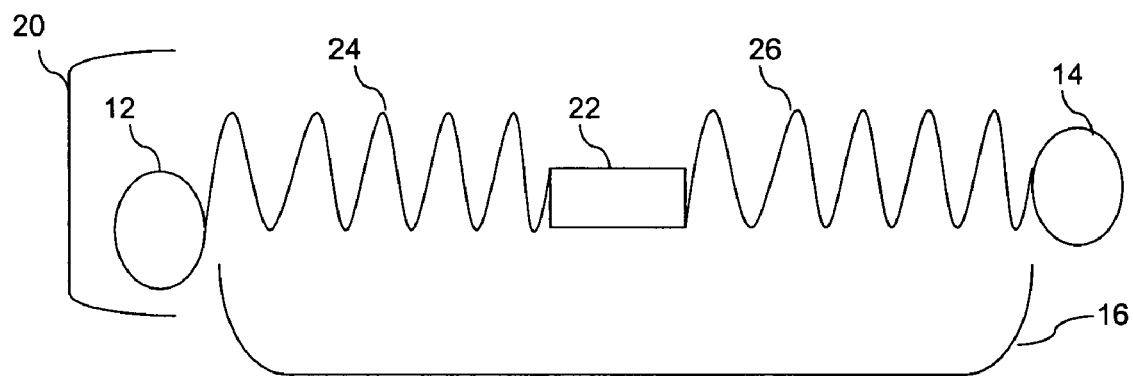
FIG. 1B is a schematic drawing showing an exemplary nanoprobe that includes functional groups linked by a molecular rod and tethers.
Figure 1C:
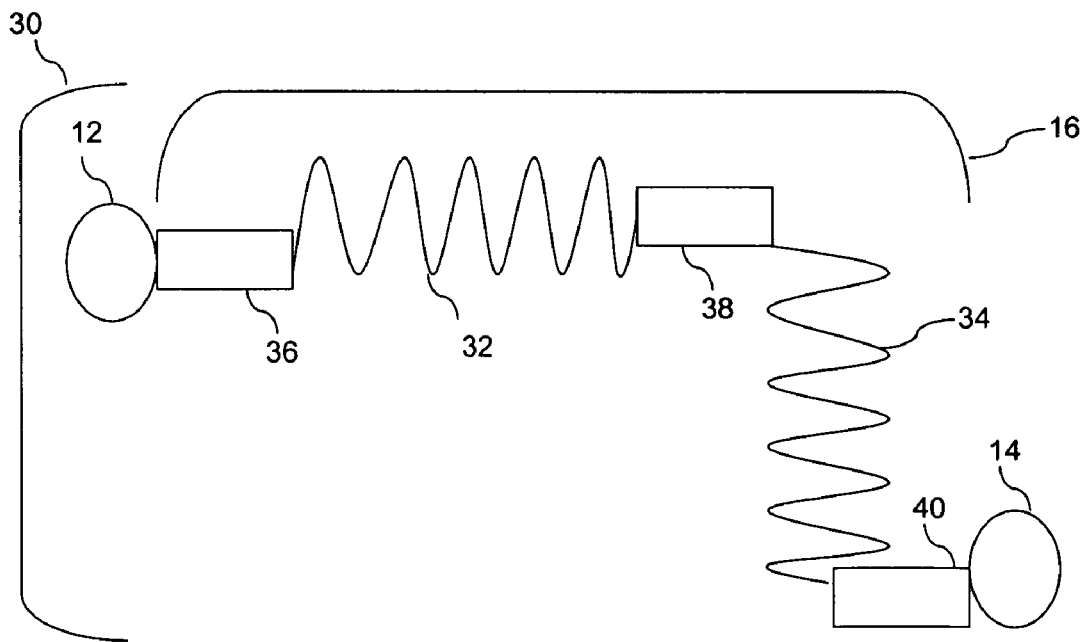
FIG. 1C is a schematic drawing showing an exemplary nanoprobe that includes functional groups linked by multiple molecular rods and tethers.

Examples of molecular linkers include, but are not limited to, tethers, molecular rods, or combinations thereof. For example, the molecular linker can include multiple molecular rods linked by tethers or multiple tethers linked by molecular rods. One particular example is shown in FIG. 1B, where the nanoprobe 20 includes first and second functional groups 12, 14 that are linked and spaced by the molecular linker 16, wherein the molecular linker is composed of a molecular rod 22 linked by tethers 24, 26. Another particular example is shown in FIG. 1C, where the nanoprobe 30 includes first and second functional groups 12, 14 that are linked and spaced by the molecular linker 16, wherein the molecular linker is composed of multiple tethers 32, 34 linked by multiple molecular rods 36, 38, 40. Although the first and second functional groups shown in FIGS. 1A-C are shown as a single entity 12, 14, multiple functional groups can be attached to a single molecular rod or a single tether. In addition, each of the first and second functional groups can include multiple functional groups. In a specific example, each molecular rod is about 100 to 200 Å (such as about 120-140 Å), and each tether is about 23 to 187 Å (such as about 60 Å).

The functional groups include molecules that can interact with one another or with the target biomolecule (or both) to provide a predetermined reaction, such as a detectable signal or a modification of a target biomolecule. The functional groups can be maintained in a spatially separated orientation by a molecular linker so that the functional groups do not interact to provide the reaction in the absence of the target molecule. However, the molecular linker permits the functional groups, under predetermined conditions, to be brought into sufficient proximity with one another to interact and produce a predetermined reaction, such as a detectable signal or modification of a target biomolecule to which the probe binds or hybridizes, or both.

Examples of functional groups include targeting moieties and activating moieties, which are brought into activating proximity when the targeting moiety binds to the target biomolecule. In particular examples, a targeting moiety brings an activatable moiety into sufficient proximity to the target for the activatable moiety to act on the target. For example, if the activatable moiety is a non-specific proteinase, the target moiety upon interacting with the target protein brings the proteinase sufficiently close to the protein target biomolecule to cleave or degrade the target protein. Therefore, activatable moieties can be used to modify a target biomolecule, for example to decrease the activity of the target biomolecule. In another example, if the activatable moiety is an acceptor fluorophore, the target moiety upon interacting with the target biomolecule brings a donor fluorophore sufficiently close to the acceptor fluorophore to excite the acceptor fluorophore, thereby resulting in the production of a detectable acceptor emission signal. Therefore, activatable moieties can be used to permit detection of the interaction of a nanoprobe with the target biomolecule.

Particular examples of targeting moieties include, but are not limited to, antibodies, proteins, nucleotides, and nucleic acid molecules. Particular examples of activating moieties include, but are not limited to, labels (such as a fluorophore) and modifying agents (such as such as enzymes, for example nucleases, ligases, or proteases, and a crosslinkable group such as psoralen). In one example, the activating moiety is an agent that can cleave the target biomolecule (for example to decrease the biological activity of the biomolecule), such as a proteinase or a nuclease. In another example, the activating moiety is an agent that can stabilize the target biomolecule, such as a ligase.

One skilled in the art will appreciate that combinations of functional groups can be used. For example, the functional group can include both a targeting moiety and an activating moiety, such as in the example of a labeled antibody. Other particular combinations of functional groups that can be included on a nanoprobe include, but are not limited to: an antibody that can specifically bind to the target protein (such as a DNA binding protein), and one or more DNA binding sites that can specifically bind to the target protein; first and second antisense oligonucleotides that can hybridize to a target nucleic acid sequence under high stringency conditions; a nucleic acid sequence capable of specifically hybridizing to a target nucleic acid, thereby forming a nucleic acid complex (such as a DNA/RNA complex), and a protein capable of cleaving the nucleic acid complex; one or more DNA binding sites that can specifically bind to the target protein and a protein capable of cleaving the protein; and a polymerase and one or more non-hydrolyzable dNTPs (or other nucleosides or nucleoside analogues).

In particular examples, one of the functional groups is an activating moiety that permits detection of the nanoprobe interacting with the target biomolecule. One particular example is a label. In particular examples the label is a functional group, or part of a functional group (such as a labeled antibody). However, one skilled in the art will recognize that one or more labels can be attached to any part of the nanoprobe that results in a significantly decreased signal in the absence of the target biomolecule, and a detectable signal in the presence of the target biomolecule. In a specific example, the label includes an acceptor fluorophore or a donor fluorophore. For example, the acceptor fluorophore and the donor fluorophores can be part of the first and second functional groups, or can be linked or otherwise attached to the probe (for example to the molecular linker, such as to a tether or to a molecular rod). For example, the acceptor fluorophore can be linked to the first functional group and the donor fluorophore linked to the second functional group, or the reverse: the acceptor fluorophore linked to the second functional group and the donor fluorophore linked to the first functional group.

Functional Groups

As described above, functional groups may include targeting moieties and activating moieties, such as agents that interact with another functional group, with the target biomolecule, or both, to provide a predetermined reaction, such as a detectable signal or a modification of a target biomolecule. The disclosed nanoprobes can include two or more functional groups, such as three or more functional groups, such as 2, 3, 4, 5, 6, 7, 8, 9 or 10 different functional groups.

In some examples, a functional group is a targeting moiety, such as one that can specifically bind to a target biomolecule, such as a protein detection agent (for example a protein, nucleic acid molecule, or an antibody) or a nucleic acid molecule detection agent (for example a protein, nucleic acid molecule, or a nucleotide, for example a non-hydrolyzable dNTP). For example a functional group can include an antibody that specifically binds to a target protein. In one example, a functional group includes a protein (such as a polymerase, for example reverse transcriptase) that binds to a target nucleic acid molecule. In other examples, a functional group is one that can specifically hybridize to the target biomolecule, such as a nucleic acid molecule, for example an antisense sequence. For example a functional group can include an antisense molecule that specifically hybridizes to a target nucleic acid sequence (for example under high stringency conditions).

In yet other examples, a functional group is an activating moiety, such as one whose biological activity towards the target biomolecule increases or one that is activated in the presence of the target biomolecule. For example, the biological activity of the activating moiety towards the target biomolecule, on a nanoprobe that includes both a targeting moiety and an activation moiety, can increase upon the interaction of a targeting moiety with the target biomolecule, by bringing the activating moiety in sufficient proximity to the target biomolecule to have the desired effect on the biomolecule. Particular examples of activating moieties whose biological activity towards the target biomolecule increases in the presence of the target biomolecule, include but are not limited to, agents that can modify the target biomolecule, for example agents (such as enzymes) that cleave the target biomolecule (such as nucleases and proteinases, for example RNase H, proteinase K, and trypsin, as well as restriction enzymes), agents that alter the interaction between the target biomolecule and the functional group (such as ligase). For example, agents that cleave the target biomolecule can be used to decrease the biological activity of the target biomolecule.

In particular examples, a nanoprobe that includes both a targeting moiety and an activation moiety decreases non-specific damage (for example to other components in the cell or in the sample). For example, a nanoprobe used to degrade a target biomolecule can include a targeting moiety that will direct the probe to the biomolecule of interest, and an activation moiety (such as an enzyme) that can cleave the target biomolecule. Although some non-specific degradation may occur, this non-specific degradation is significantly reduced by the presence of the targeting moiety.

In other examples the activating moiety specifically recognizes and interacts with, modifies, and/or degrades a particular target such as a pathogen or pathogenic molecule, such as amyloid protein plaques of the type found in Alzheimer's disease or some prion disorders (such as spongiform encephalopathies). Hence the targeting moiety may be specific for the amyloid protein and the activating moiety may be a ubiquitinase that specifically interacts with the amyloid protein to target it to the proteasome without substantially nonspecifically degrading other intracellular proteins.

In one example, a functional group is an activating moiety that is activated in the presence of the target biomolecule. Particular examples of such activating moieties include labels, such as a fluorophore. For example if one of the activating moieties is a donor fluorophore, and another activating moiety is an acceptor fluorophore, binding of the nanoprobe to the target biomolecule brings the donor and acceptor fluorophores in sufficient proximity such that the donor fluorophore can activate the acceptor fluorophore, thereby producing a detectable acceptor fluorophore emission signal.

The functional groups selected will depend on the target biomolecule of interest, and whether the target biomolecule is to be detected, modified, or both. For example, if the target biomolecule is a protein, particular examples of targeting moieties include antibodies and proteins that specifically bind to the target protein. If the protein is a DNA binding protein, the targeting moieties can include one or more DNA sequences specific for the target protein. If the target biomolecule is a nucleic acid sequence, particular examples of targeting moieties include nucleic acid molecules that can specifically hybridize to the target nucleic acid sequence, such as an antisense molecule. In particular examples an antisense functional group can hybridize to a target nucleic acid sequence under high stringency conditions.

If detection of the biomolecule is desired, targeting agents that specifically bind to the target biomolecule can be used, such as a protein binding agent, for example a protein or an antibody or a nucleic acid sequence. For example, if detection of the target biomolecule is desired, even if the target molecule is destroyed or disassociates from the nanoprobe, a ligase can be used as an activating moiety to seal the probe after the probe binds to the target biomolecule. If modification of the biomolecule is desired, such as reducing the biological activity of the target biomolecule (such as a reduction of at least 50%, at least 80%, or even at least 95%), agents that specifically cleave the target biomolecule can be used. Examples of such agents include, but are not limited to: proteinases (for example if the target biomolecule is a protein), RNases (for example if the target biomolecule is an RNA or a DNA/RNA hybrid), and DNases (for example if the target biomolecule is a DNA sequence). In particular examples, the specific cleaving agents can, in addition to recognizing a particular class of target biomolecules (such as proteins or nucleic acid molecules), specifically recognize and act upon or cleave particular targets, such as an enzyme that acts upon a specific protein substrate.

Other targeting agents include aptamers, which are DNA, RNA, or protein domains that target proteins, small organic molecules, and even entire organisms. Such aptamers can serve as targeting moiety functional groups joined by the linker. For example, aptamers are known for many agents including IgE (Invitrogen, Catalog Number 02-9788) and hemagglutinin of influenza (Jeon et al., *J. Biol. Chem.* 279: 48410-9, 2004). In some examples, the aptamer is divided in half, and each half placed on the two sides of the rod-tether nanoprobe (for example FIG. 1B 12, 14). In the absence of the target, the nanoprobe would not hold together, but in the presence of the target the parts would come together and produce a signal.

Tethers

Molecular linkers can include one or more tethers, which can provide flexibility to the probe. Ideally, tethers are flexible enough to allow movement of the functional groups, for example to permit the functional groups to interact with one another, or to interact with a target biomolecule. The length of the tether should be sufficient to substantially avoid interaction of the functional groups in the absence of the target biomolecule, and allow interaction of the functional groups in the presence of the target biomolecule. However, the tether is ideally not so long as to result in entanglement of the tether or the functional groups. In particular examples, tethers are water soluble and non-toxic.

In particular examples, the length of the tether is long enough to separate the functional groups in the absence of the target biomolecule, but not so long as to result in tangling of the nanoprobe or the functional groups, and short enough to allow the functional groups to interact with the target biomolecule when present or with one another.

Examples of particular materials that can be used as tethers include, but are not limited to, single-stranded DNA molecules, sugar chains, peptides (such as the connector between two parts of the RecB protein), and polyethylene glycol (PEG) or any other flexible polymer having the properties disclosed herein. In a particular example, a tether is composed of two or more of these agents. In a specific example a tether includes, or in some examples consists of, PEG.

In particular examples, the tether is about 10-500 Å, such as 20-200 Å, 23-187 Å, 100-140 Å, or 70-94 Å, for example 120 Å.

In particular examples, the tether is composed of PEG, such as 3 to 7 units of 18-atom PEG spacers that are 23.4 Å long, such as 2-4 or 3-4 of such spacers. PEG is non-toxic, flexible, hydrophilic and can be inserted as spacers during DNA synthesis (SyntheGen, Glen Research).

In one example, the tether is a single-stranded DNA (ssDNA) molecule, for example having a length of 10-40 nucleotides, such as 10-30 nucleotides, 10-20 nucleotides, for example 10 nucleotides, 20 nucleotides, or 40 nucleotides. In particular examples, a ssDNA tether can anneal to another nucleic acid strand, thereby converting a flexible tether into a rigid molecular rod. Ideally, the sequence is one that does not specifically hybridize to itself, the functional groups, or to a nucleic acid sequence in the sample to be analyzed.

In one example, the tether is a sugar chain (for example having a length of 10-100 sugar moieties, such as 10-75, 10-50, or 20-40 sugar moieties).

Molecular Rods

Molecular linkers can include one or more molecular rods, which can provide sufficient rigidity to the probe to reduce interaction of the first and second functional groups in the absence of the target biomolecule. However, the length of the rod is sufficient to permit interaction of the functional groups in the presence of the target biomolecule. In some examples, the presence of a molecular rod in the nanoprobe reduces the likelihood of entanglement and can increase the speed of the binding of the nanoprobe to the target biomolecule.

The disclosed nanoprobes can include one or more molecular rods, such as at least two molecular rods, for example 1, 2, 3, 4, 5, 6, 7, 8, 9, or 10 molecular rods. In one example, use of one or more molecular rods reduces the required tether length, thereby reducing the cost and size of the device.

In a particular example, the molecular rod is a double-stranded DNA (dsDNA) sequence. The length of the dsDNA is one that allows interaction of the functional groups in the presence of the target biomolecule, but reduces their interaction in the absence of the target biomolecule. If the nanoprobe includes donor and acceptor fluorophores, the length of the dsDNA is one that allows interaction of the fluorophores in the presence of the target biomolecule, but reduces their interaction in the absence of the target biomolecule. In specific examples, the dsDNA molecular rod is a length that is about equal to the persistence length of 400-500 Å. However, one skilled in the art will recognize that lengths shorter or greater can be used, as long as the rod reduces the interaction of functional groups in the absence of the target biomolecule, and does not result in significant entanglement of a molecular linker. In specific examples, the dsDNA molecular rod is 150 to 200 nucleotides, such as 10-150 nucleotides, such as 10-140 nucleotides, 20-140 nucleotides, 20-100 nucleotides, 20-50 nucleotides, 30-50 nucleotides, or 30-40 nucleotides, for example 35, 36, 37, 38, 39, 40, 41, 42, 43, 44, or 45 nucleotides. In specific examples, the dsDNA molecular rod is at least 10 nucleotides, such as at least 20 nucleotides. In a particular example, the molecular rod is a dsDNA of 40 bases. Bases are 3.38 Å thick so 40 base pairs is 135 Å long, which is greater than the typical FRET distance. In a particular example, the sequence of the dsDNA is chosen using the NANEV program (Goodman et al., *BioTechniques*, 38:548-50, 2005).

In other particular examples, the molecular rod is composed of DNA molecules containing modifications or variants of the DNA, such as peptide backbone DNA (Peptide Nucleic Acid, PNA) or locked nucleic acids (LNAs). In particular examples, such DNA variants are used to alter the helix thermal stability and resistance to nucleases. In yet another example the molecular rod is composed of carbon nanotubes (for example nanotubes that are 100-200 Å in length). In yet other examples, the molecular rod includes bacteria, virus particles, or viral tail fibers.

Labels

In particular examples, nanoprobes disclosed herein include one or more detectable labels, for example to permit detection of the nanoprobe interacting with a target biomolecule. Exemplary labels that can be used include fluorophores, chemiluminescent agents, and charge. For example, a change in charge can be detected as the target biomolecule approaches a capacitor.

In a particular example, a nanoprobe includes an acceptor fluorophore and a donor fluorophore. Although the figures herein only show a single donor and acceptor fluorophore on the nanoprobe, multiple fluorophores can be included on the nanoprobe to increase the signal or to provide combinations of spectra. Ideally, the acceptor and donor fluorophores are attached to the nanoprobe in a position that decreases their interaction in the absence of the target biomolecule (thereby reducing detectable signal). However, in the presence of the target biomolecule, the interaction of the functional groups with the target biomolecule allows the acceptor and donor fluorophores to interact, such that the donor fluorophore excites the acceptor fluorophore and the acceptor emits at its characteristic wavelength, thereby generating a detectable signal.

In a particular example, the donor fluorophore has a large Stokes shift. This decreases the excitation of the acceptor fluorophore by the donor excitation light frequency. Appropriate filtration can also reduce or remove the excitation wavelength, leaving only the emission spectrum from the acceptor to be detected.

In a particular example, the donor fluorophore is Green Fluorescent Protein (GFP). In another particular example, the donor fluorophore is a chemiluminescent molecule, such as aequorin. Chelated lanthanides provide bright, large stokes shift, non-bleaching luminophores with sharp emission spectra, and can therefore be used as donors. The use of a chemiluminescent molecule as the donor fluorophore eliminates the need for an external light source.

Particular examples of acceptor and donor fluorophore pairs that can be used include, but are not limited to: GFP mutant H9-40 (Tsien, 1998, *Ann. Rev. Biochem.* 67:509) as a suitable donor fluorophore for use with BODIPY, fluorescein, rhodamine green, Oregon green, tetramethylrhodamine, Lissamine™, Texas Red and naphthofluorescein as acceptor fluorophores, and fluorophore, 3-(ϵ-carboxy-pentyl)-3'-ethyl-5,5'-dimethyloxacarbocyanine (CYA) as a donor fluorophore for fluorescein or rhodamine derivatives (such as R6G, TAMRA, and ROX) as acceptor fluorophores. Other particular examples of acceptor and donor fluorophore pairs include, but are not limited to: 7-dimethylaminocoumarin-4-acetic acid (DMACA) and fluorescein-5-isothiocyanate (FITC); 7-amino-4-methyl-3-coumarinylacetic acid (AMCA) and fluorescein-5-isothiocyanate (FITC); and fluorescein-5-isothiocyanate (FITC) and tetramethylrhodamine isothiocyanate (TRITC).

Examples of fluorescent dyes that can be particularly used for attaching a fluorophore to a molecular linker include the Alexa Fluor series (Molecular Probes, Eugene, Oreg.). In one example, Alexa Fluor 430 absorbs at 430 nm and, because of its high Stokes shift, emits far away at 540 nm, and can therefore be used as a donor fluorophore. Alexa Fluor 430 can be used in particular examples with Alexa Fluors 546, 555, 568, 594, 647, and BODIPY 630 as acceptor fluorophores since their excitation spectra overlap the 540 nm emission peak of Alexa Fluor 430.

Donor and acceptor molecules can also be designed using bimolecular fluorescence complementation (BiFC), a technique developed by Hu and Kerppola (Hu et al., *Nat. Biotechnol.* 21:539-45, 2003; Hu et al., *Mol. Cell.* 9(4):789-98, 2002). Two partial GFP fragments join to give a complementation and hence fluorescence. The complementation takes only a few moments but formation of the chromophore takes a long time, $t_{1/2}$=300 seconds. So the method can be slower than FRET. Because the chromophore forms permanently, it can be used in a nanoprobe to provide a long-lasting result.

Quantum Dots

In one example, one or more nanoprobes disclosed herein are attached to fluorescent nanoparticles referred to as quantum dots. The quantum dot or Cornell dot (silica coated fluorophores) can be the donor fluorophore, while the nanoprobes attached to the quantum dot can include one or more corresponding acceptor fluorophores. In particular examples, the nanoprobes are attached to the quantum dot directly, or via a linker, such as with antibodies coating the quantum dot.

The quantum dots can be tethered together, for example with a molecular linker of a sufficient length to prevent significant FRET. In another example, quantum dots are tethered together using a molecular linker. In another example, three dimensional molecular linkers (such as tetrahedron constructions) keep some nanoprobe functional groups a significant distance from the surface of a quantum dot such that when a functional group on the nanoprobe binds to the target biomolecule, the target biomolecule is brought to the quantum dot surface and is detected by FRET.

The quantum dot can part of the nanoprobe, thereby replacing a fluorophore, such as replace a donor, acceptor, or both.

Reducing Photobleaching

Methods of reducing photobleaching are known in the art, and the disclosed methods are not limited so particular reduction methods. In one example, confocal microscopy can be used to reduce photobleaching of fluorophores (described above). Another means that can be used to reduce photobleaching is to incubate the sample in a solution containing an oxygen scavenger system, for example as described by Kitamura et al. (*Nature*, 397:129, 1999); Okada and Hirokawa (*Science*, 283:1152, 1999); Harada et al. (*J. Mol. Biol.* 216:49, 1990). Examples of solutions include: 1% glucose, 0.05 mg/ml glucose oxidase and 0.1 mg/ml catalase; and 0.5% 2-mercaptoethanol, 4.5 mg/ml glucose, 216 μg/ml glucose oxidase, 36 μg/ml catalase, 2 mM ATP in buffer.

One method that can be used to reduce photobleaching is to coat fluorophores with calcium phosphate (also known as molecular dots, see Adair et al., Colloidal Lessons Learned for Dispersion of Nanosize Particular Suspensions, in Lessons in Nanotechnology from Traditional and advanced Genetics, 2005). For example, when trapped inside 60nm nanoparticles, fluorophores remain extremely stable and do not significantly decay. For the present probes, small nanoparticles of about 0.5-2 nm (such as 1 nm to 2 nm) having one amino group (or other unique attachment point) on the surface can be used. For example, a tethered fluorophore having an amino group (to permit attachment of the fluorophore to the desired location on the nanoprobe) can be coated and attached to a nanoprobe. The layering can be accomplished by incubating the fluorophore with carboxyl (-COOH) groups and then adding calcium or aluminum. On adding phosphate $H_2PO_4^-$, another layer is formed. In some examples, gold is used to coat the fluorophores. The resulting particles have plasmon resonance, possibly enhancing the fluorescence in addition to the protective coating (see Lakowicz, *Anal. Biochem.* 298: 1-24, 2001).

Yet other methods of reducing photobleaching include placing a nanoprobe proximal to metallic islands (Lakowicz, *Anal. Biochem.* 298: 1-24, 2001) and incubation in Trolox (Rasnik et al., *Nat. Methods* 3:891-3, 2006).

Exemplary Nanoprobes for Detection of Biomolecules

The present disclosure provides multiple examples of nanoprobes that can be used to detect one or more biomolecules. For example, such nanoprobes can be used to determine whether a target biomolecule is present or absent in a sample. In some examples, the target biomolecule is quantitated.

One particular example of a nanoprobe 50 includes two functional groups linked by a tether as shown in FIG. 2A. One functional group includes a protein binding agent 52 (such as an antibody or protein) and an acceptor fluorophore 54. The other functional group contains a DNA molecule having one or more protein binding sites 56, and a donor fluorophore 58. The functional groups are joined via a molecular linker 60 (such as a tether). Such a nanoprobe can be used to detect binding of a protein to DNA (FIG. 2B). The protein binding agent 52 specifically binds to the protein 62 that binds to the protein binding sites 56. One skilled in the art will appreciate that the positions of the donor fluorophore 58 and the acceptor fluorophore 54 can be switched. As shown in FIG. 2B, in the presence of the target biomolecule 62, the targeting moieties (the protein binding agent 52 and the protein binding sites 56) bind to the target biomolecule 62 in sufficient proximity to bring the activating moieties (donor fluorophore 58 and acceptor fluorophore 54) into sufficient proximity to allow the donor fluorophore 58 to transfer energy 64 to the acceptor fluorophore 54. This energy transfer activates the acceptor fluorophore 54 so that it emits at its characteristic wavelength, thereby generating a detectable signal 66.

The protein binding agent 52 is a targeting moiety that includes any agent that can specifically bind to a protein of interest, and ideally is capable of attaching to a tether and a label, such as a fluorophore. Examples of protein binding agents 52 include, but are not limited to, antibodies and proteins. Particular examples of protein binding agents include agents that can bind to a DNA binding protein. DNA binding proteins include any protein that binds to double- or single-stranded DNA. Examples include proteins involved in the regulation of gene expression (including transcription factors), proteins involved in the packaging of DNA within the nucleus (such as histones), and nucleic acid-dependent polymerases involved in DNA replication and transcription, as well as accessory proteins involved in these processes. One particular example of a DNA binding protein is p53.

In particular examples, the DNA binding protein is p53, and the protein binding agent 52 is an agent that can detect p53. Examples include, but are not limited to, an anti-p53 antibody (such as pAb421) or a p53-binding protein (such as P53BP1, MDM2, Rad51, TBP, P300, SRC1, and ACTr). In a particular example, a p53 activating or non-activating antibody is used. A nanoprobe using an activating antibody will activate p53 to bind to DNA and so will detect all p53 molecules while a non-activating antibody will only detect p53 that has been activated by another mechanism. By using these two nanoprobes with a common donor and different acceptor fluorophores, the ratio of non-activated to activated p53 can be monitored. Other p53 antibodies can be used to detect the various different phosphorylation and acetylation modifications of p53. In addition, antibodies can be used to detect particular p53 mutations.

The one or more protein binding sites 56 can include at least two protein binding sites, such as at least three DNA binding sites, for example 1, 2, 3, 4, 5, 6, 7, 8, 9 or 10 binding site sequences. The sequence of the protein binding site 56 will depend on the target protein to be detected. For example, if detection of p53 binding to DNA is desired, the protein binding site 56 can include or consist of the sequence GAACATGCCCGGGCATGTCC (SEQ ID NO: 1), GAACATGTCCCAAACATGTTG (SEQ ID NO: 2), or RRRCWWGYYYRRRCWWGYY (SEQ ID NO: 3) (wherein R is any purine, Y is any pyrimidine, and W is A or T). Other particular p53 binding sequences are known (for example see Miner and Kulesz-Martin *Nucleic Acids Res.* 25:1319-26, 1997; Kaku et al., *Nucleic Acids Res.* 29:1989-93, 2001, herein incorporated by reference as to the p53 binding sequences). As shown in FIG. 2A, the one or more protein binding sites 56 are represented by three rectangles with crosses. In one example, each rectangle represents half of a p53 site. p53 could bind to the left and middle as shown in FIG. 2B, or to the middle and right rectangles. Since there are two sites for p53 to bind on the nanoprobe 50 but only one can be bound at a time, the sensitivity of the p53 assay can be doubled (for example see U.S. Pat. No. 6,774,222).

Another particular example of a nanoprobe that includes two functional groups linked by a tether is shown in FIG. 3A. Each functional group includes both a targeting moiety 102, 104 and an activating moiety 106, 108 where the activating moiety serves as a label. Such a nanoprobe can be used to detect any antigenic compound of interest, such as a protein. The nanoprobe 100 includes at least two protein binding agents 102, 104 (such as an antibody or protein) linked via a molecular linker 110 (such as a tether). One antibody 102 carries a donor fluorophore 106 and the other antibody 104 carries an acceptor fluorophore 108 of a FRET pair. One skilled in the art will appreciate that the positions of the donor fluorophore 106 and the acceptor fluorophore 108 can be switched. As shown in FIG. 3B, in the presence of the target protein 112, the targeting moieties (protein binding agents 102, 104) specifically bind to the target protein 112, thereby bringing the two activating moieties (fluorophores 106, 108) into sufficient proximity to allow the donor fluorophore 106 to transfer energy 114 to the acceptor fluorophore 108. This energy transfer activates the acceptor fluorophore 108 so that it emits at its characteristic wavelength, thereby generating a detectable signal 116.

In particular examples, the protein binding agents 102, 104, are antibodies or proteins that can specifically bind to an antigenic compound of interest, such as a protein. For example, if the protein is p53, p53 antibodies or p53 binding proteins can be used in the nanoprobe shown in FIG. 3A, for example to measure total p53 concentration independently of p53 DNA binding ability. In contrast, the nanoprobe 50 shown in FIG. 2A would only detect p53 if it were bound to the DNA binding sequence. For example, nanoprobe 100 in FIG. 3A can be used even if p53 is mutated in a way that interferes with p53's ability to bind to DNA, and thus would not be detected by the nanoprobe 50 shown in FIG. 2A. In one example, the nanoprobe 100 is used for detecting modified proteins. For example, antibodies specific to a modified protein can distinguish between the wild type and a modified protein (such as a mutant protein). For example, anti-phospho-p53 and anti-acetylated-p53 antibodies are available from commercial sources (such as Cell Signaling Technology, Inc.). Using these antibodies, whether or not p53 has been activated and the specific way in which p53 has been activated can be determined.

In another specific example, the antibodies 102, 104 are matched antibody pairs. Matched antibody pairs are antibodies that recognize different domains (such as epitopes) of the same protein, and therefore can be used to detect an antigenic protein of interest (such as epidermal growth factor, human growth factor, Il-8, IL-16, and prostate specific antigen). Such antibodies are available from commercial sources such as Anogen (Mississauga, Ontario, Canada). In yet another example the antibodies 102, 104 are specific for biowarfare agents (such as *Bacillus anthracis*) and p450 variants. In one example, the antibodies 102, 104 detect a cancer-specific antigen, such as BRCA1 (for example to determine if a cancer is BRCA1 positive, or to determine if a particular treatment modality is appropriate for a subject having cancer), p53 (for example to determine if a cancer is p53 positive, to determine if a cancer expresses a particular p53 mutation, or to determine if a particular treatment modality is appropriate for a subject having cancer). In another example, the antibodies 102, 104 detect human chorionic gonadotropin (HCG) (for example as a pregnancy test).

In particular examples, a molecular linker includes a molecular rod, for example as shown in FIG. 4A. The inclusion of a molecular rod, such as a dsDNA molecule, can increase the rigidity of the molecular linker and further separate the functional groups in the absence of the target biomolecule. For example, a nanoprobe with a molecular rod can have at least two points about which the antibodies or other functional groups (such as a binding protein) will move by Brownian motion. That is, there will be at least two "cloud spheres" each of which represents all the possible locations of a functional group with respect to the end of a rod as allowed by tethers. By design, these spheres will intersect to some degree. In the absence of a target molecule, the nanoprobe can maintain substantial sphere separation, but ideally the distance between the two ends of the molecular rod is less than the sum of the two tether lengths and the target molecule size when held between the two 'hands'. In the presence of the target biomolecule, both "hands" hold onto the target, bringing the activatable moieties (such as the donor and acceptor fluorophores) together, thereby creating a detectable signal. In particular examples, the molecular rod is used to decrease FRET between the donor and acceptor fluorophores on the nanoprobe in the absence of the target biomolecule.

FIG. 4A shows the nanoprobe of FIG. 3A with the inclusion of a double-stranded DNA sequence as the molecular rod. The nanoprobe 200 includes functional groups 202, 204, 206, 208, linked by a molecular linker composed of tethers 210, 212 linked by a molecular rod 214. Each functional group includes both a targeting moiety 202, 204 and an activating moiety 206, 208 where the activating moiety serves as a label. Such a nanoprobe can be used to detect any antigenic compound of interest, such as a protein. One skilled in the art will appreciate that the positions of the donor fluorophore 206 and the acceptor fluorophore 208 can be switched. Similar to what is shown in FIG. 3B, in the presence of the target protein, the protein binding agents 202 204 will specifically bind to the target protein, thereby bringing the two fluorophores 206 208 into sufficient proximity to generate a detectable signal.

The molecular rod 214 can include a dsDNA sequence that increases the rigidity of the molecular linker, for example to reduce the interaction of the protein binding agents in the absence of the target antigenic compound. In particular examples the rod reduces the FRET signal in the absence of the target antigenic compound, while still allowing interaction of the donor and acceptor fluorophores in the presence of the antigenic compound. In a particular example, the molecular rod is a dsDNA sequence of 10 to 140 nucleotides, such as 20-100 nucleotides, for example 40 nucleotides. In a specific example the molecular rod is 120 angstroms (Å).

Figure 4B:
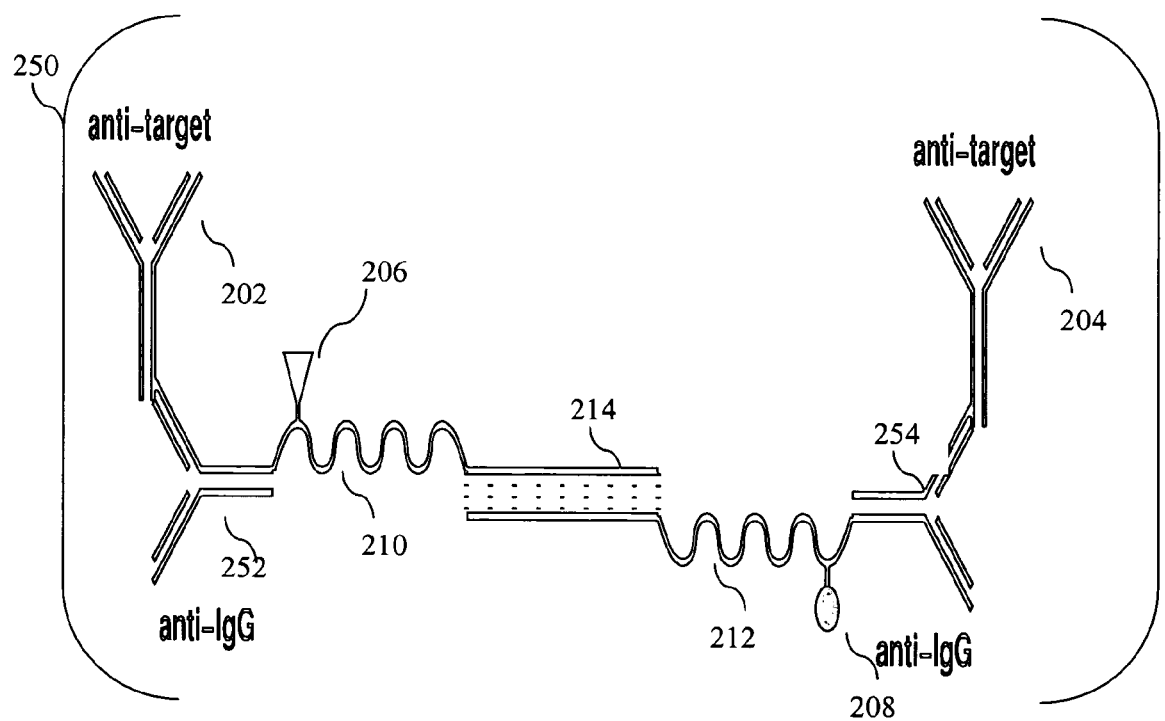
FIG. 4B is a schematic drawing showing an exemplary nanoprobe that includes anti-IgG molecules, which can be used to detect an antigenic compound. In particular examples, this nanoprobe does not include the anti-target moiety, and the anti-target moiety is selected by a user.

FIG. 4B shows a variation of the nanoprobe 200 shown in FIG. 4A. The nanoprobe 250 further includes anti-IgG antibodies 252 254. In a particular example, the anti-IgG antibodies 252 254 are anti-mouse IgG antibodies, such as a fluorescently labeled anti-mouse IgG antibody (for example available from Jackson ImmunoResearch Laboratories, Inc., West Grove, Pa.), which are bound to mouse anti-target biomolecule antibodies. This approach allows the anti-target biomolecule antibodies to be exchanged easily. Therefore, the nanoprobe 250 can be generated without the anti-target antibodies 202 204, and the end user can attach the desired mouse anti-target biomolecule antibodies of interest.

By making molecular rod 214 from dsDNA, the two halves of the nanoprobe can be constructed independently and then annealed to create rod 214. That is, anti-IgG 252 is attached to fluorophore 206, tether 210 and the upper DNA strand of rod 214 in one reaction. In a separate reaction anti-IgG 254 is joined to fluorophore 208, tether 212 and the lower DNA strand of rod 214. These two components provide a "kit" to an end user. The end user attaches anti-target antibody 202 to the left component in one reaction. In a separate reaction, the end user attaches anti-target antibody 204 to the right component. The end user then joins the left and the right components to create the final nanoprobe containing dsDNA rod 214. By this means the anti-IgGs 252 and 254 can be identical, but every nanoprobe contains one anti-target of type 202 and another anti-target of type 204.

Another particular example of a nanoprobe that includes a molecular rod is shown in FIG. 5A. In contrast to the nanoprobe 200 shown in FIG. 4, which showed the functional groups 202 and 204 attached directly to the tether 210, 212, the nanoprobe 300 shown in FIG. 5A shows functional groups 302, 304 attached directly to a dsDNA oligonucleotide 306 and functional groups 308, 310 attached directly to a dsDNA oligonucleotide 312. Each functional group of nanoprobe 300 includes both a targeting moiety 302, 308 and an activating moiety 304, 310 where the activating moiety serves as a label. By replacing part of the tether 314, 316 with a molecular rod 306, 312, as well as introducing a molecular rod 318 within the tether, the region of space explored by the functional group 302, 304, 308 or 310 is reduced to the surfaces of two spheres rather than the entire volume of two spheres. This can reduce or eliminate tangling of tethers 314, 316. In one example, oligonucleotide 306, 312 (which in some examples are molecular rods) are included in a nanoprobe, to allow for generation of a particular molecular linker. For example, DNA and PEG constructs can be synthesized commercially. Attachment of fluorophores and other functional groups to such a molecular linker can be accomplished by use of an amino group (for example an amino group at the end of the linker, or within the linker). In particular examples, the oligonucleotides 306, 312 are dsDNA with one amino group per DNA strand. In example, each amino group is used to attach a functional group. As shown in FIG. 5A, oligonucleotides 306, 312 connect the functional groups 302, 308 and fluorophores 304, 310, respectively, to the nanoprobe. Nanoprobe 300 therefore provides a means of construction in which only one amino group is needed for each strand of DNA/PEG synthesized.

The nanoprobe 300 can also be used to detect any antigenic compound of interest, such as a protein. In a particular example, the nanoprobe 300 includes at least two functional groups 302 and 308 (such as protein binding agents, for example antibodies or proteins), that are linked together via a molecular linker composed of two or more molecular rods 306, 312, 318 linked by two or more tethers 314, 316. The nanoprobe 300 includes a donor fluorophore 304 and an acceptor fluorophore 310. One skilled in the art will appreciate that the positions of the donor fluorophore 304 and the acceptor fluorophore 310 can be switched. In a particular example, at least two functional groups 302 and 308 are anti-mouse IgG antibodies, which allows anti-target biomolecule antibodies to be exchanged easily (as described above for FIG. 4B).

Figure 5B:
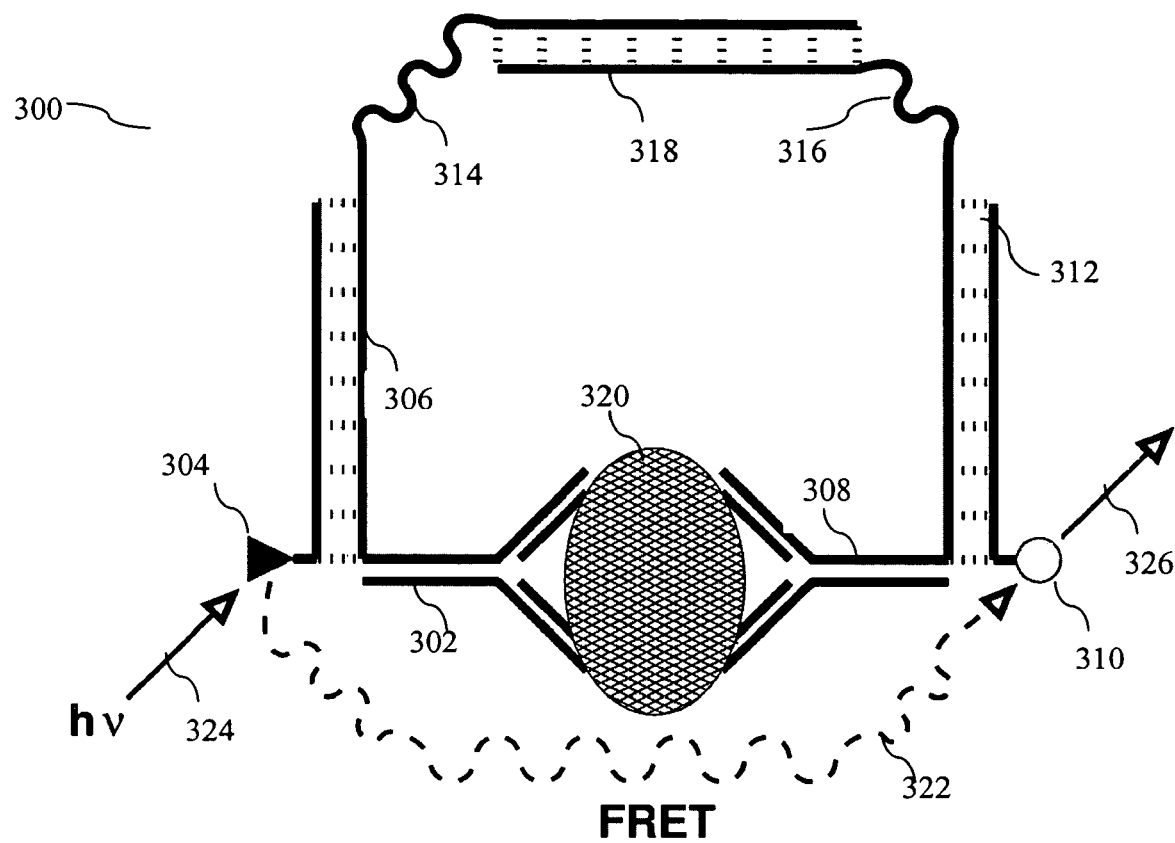
FIG. 5B is a schematic drawing showing binding of the exemplary nanoprobe of FIG. 5A to a target antigenic compound, thereby generating a detectable signal.

As shown in FIG. 5B, in the presence of the target biomolecule 320 (such as an antigenic compound), the protein binding agents 302, 308 will specifically bind to the target biomolecule 320, thereby bringing the two fluorophores 304, 310 into sufficient proximity to allow the donor fluorophore 304 to transfer energy 322 to the acceptor fluorophore 310, upon excitation 324 of the donor fluorophore 304. This energy transfer activates the acceptor fluorophore 310 so that it emits at its characteristic wavelength, thereby generating a detectable signal 326.

Figure 5C:
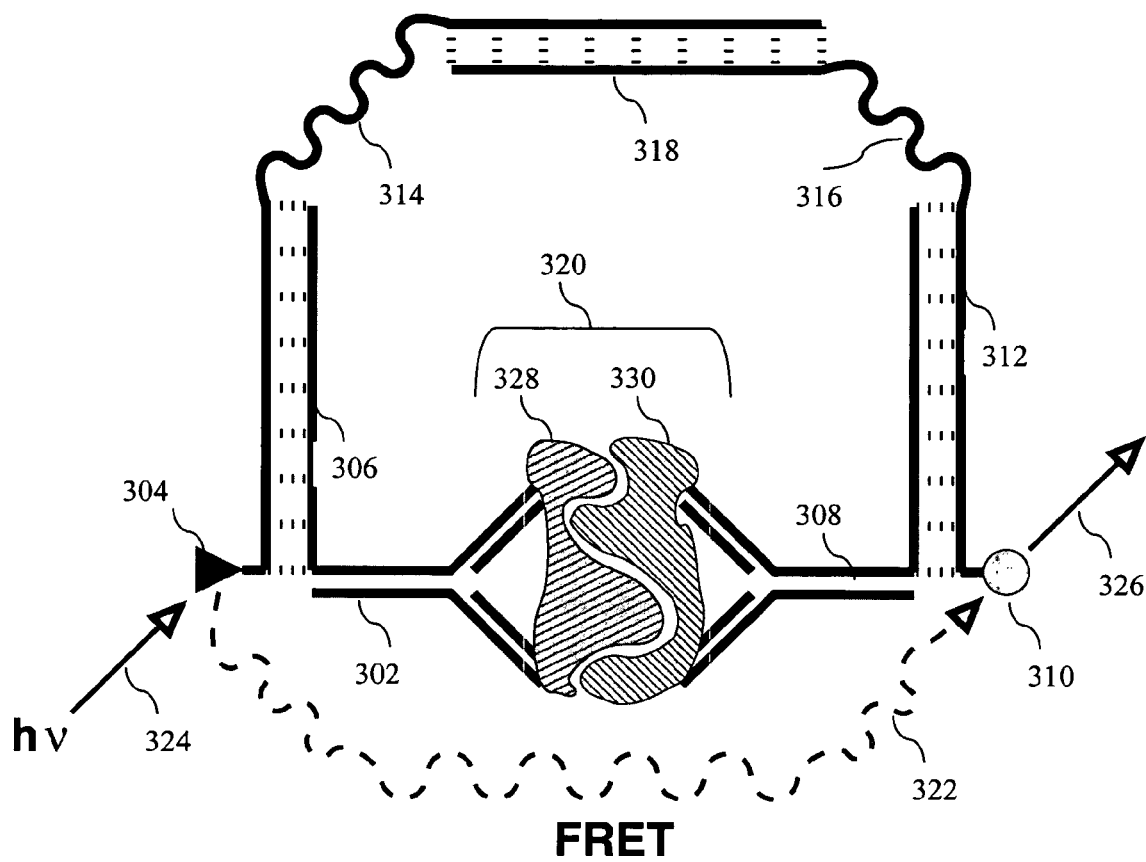
FIG. 5C is a schematic drawing showing binding of the exemplary nanoprobe of FIG. 5A to a target antigenic compound that is a complex of at least two biomolecules, thereby generating a detectable signal.

In a particular example, the nanoprobe 300 is used to detect a protein complex. For example, as shown in FIG. 5C, if the target biomolecule 320 is a protein complex that includes at least two different biomolecules 328, 330 that can interact and form a detectable complex, nanoprobes that include protein binding agents 302, 308 that can each specifically bind to one member of a protein complex can be used. For example, protein binding agent 302 can detect biomolecule 328 and protein binding agent 308 can detect biomolecule 330. If the biomolecules 328, 330 interact, then the distance between the fluorophores 304, 310 decreases, and a detectable signal 326 will be observed.

Figure 6:
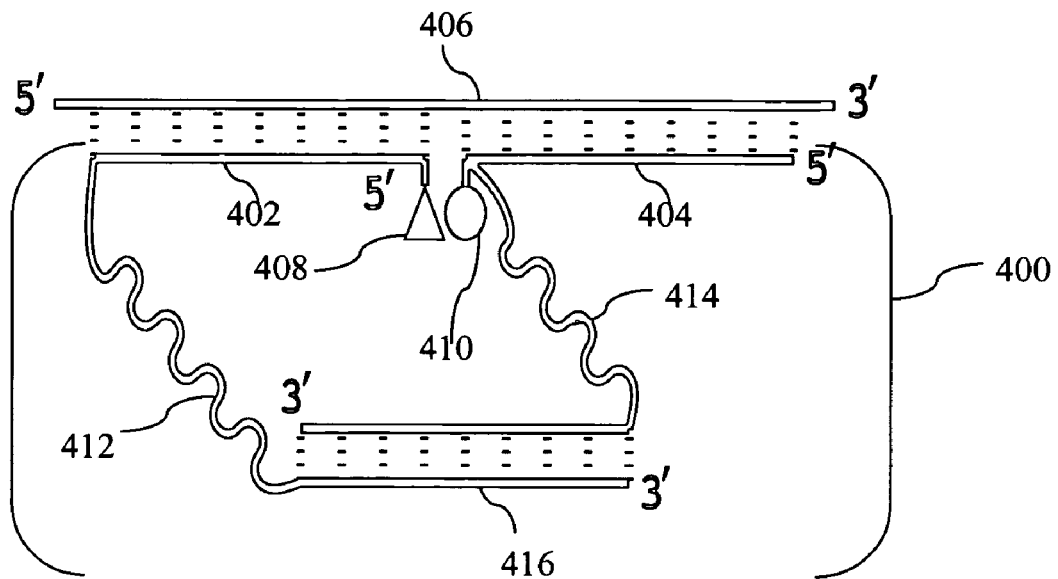
FIG. 6 is a schematic drawing showing an exemplary nanoprobe that includes antisense functional groups, which can be used to detect a target mRNA molecule.

Nanoprobes can also be used to detect target nucleic acid molecules, for example to determine whether a particular nucleic acid sequence is present or absent in a sample. FIG. 6 shows a nanoprobe 400 that includes targeting moieties as functional groups (antisense DNA oligonucleotides 402, 404 that can specifically hybridize to a target RNA sequence 406), as well as activating moieties (a donor fluorophore 408 is attached to the 5' end of one antisense oligonucleotide 402, and an acceptor fluorophore 410 is attached to the 3' end of the other antisense oligonucleotide 404). The antisense oligonucleotides 402, 404 are linked via a molecular linker that includes tethers 412 414 separated by a molecular rod 416. One skilled in the art will appreciate that the positions of donor 408 and acceptor 410 fluorophores can be reversed. In the absence of the mRNA target 406 (not part of the nanoprobe) there is little detectable signal. However, as shown in FIG. 6, when the antisense oligonucleotides 402, 404 specifically hybridize to the mRNA target 406, the donor 408 and an acceptor fluorophore 410 are in sufficient proximity to allow the acceptor fluorophore 410 to produce a characteristic wavelength of light, resulting in a detectable signal. In particular examples, the nanoprobe 400 shown does not require the use of high temperatures to melt a DNA helix, thereby permitting its use in vivo. For example, the nanoprobe 400 can be introduced into a living cell to detect mRNA inside the cell. The detectable signal can be measured using known methods in the art, such as fluorescence microscopy.

A variation of nanoprobe 400 is shown in FIG. 7. The nanoprobe 500 in FIG. 7 includes antisense oligonucleotides 502, 504 that can specifically hybridize to a target RNA sequence 506, which are linked via tethers 508 510 that are separated by a molecular rod 512. A dsDNA molecule 514 is used to attach the ligase 516 via a tether 518. The nanoprobe 400 includes three molecules, which are hybridized to form the nanoprobe. The first molecule includes fluorophore 520, antisense oligonucleotide 502, tether 508, the bottom strand of molecular rod 512, and the top strand of dsDNA molecule 514. The second molecule includes fluorophore 522, antisense oligonucleotide 504, tether 510, and the top strand of molecular rod 512. When the first and second molecules are hybridized, this results in the formation of molecular rod 512. Therefore, the sequence of the top and bottom strand of molecular rod 512 are complementary. The third molecule includes the bottom strand of dsDNA molecule 514, tether 518, and ligase 516. When the second and third molecules are hybridized, this results in the formation of dsDNA molecule 514. Therefore, the sequences of the top and bottom strand of dsDNA molecule 514 are complementary.

The nanoprobe 500 also includes activating moieties: donor fluorophore 520 attached to the 5' end of antisense oligonucleotide 502, and acceptor fluorophore 522 attached to the 3' end of antisense oligonucleotide 504. One skilled in the art will appreciate that the position donor and acceptor fluorophores can be reversed. In the absence of the mRNA target 506 (not part of the nanoprobe) there is little detectable emission signal from the acceptor fluorophore 522. However, as shown in FIG. 7, when the antisense oligonucleotides 502, 504 specifically hybridize to the mRNA target 506, the donor 520 and an acceptor fluorophore 522 are in sufficient proximity to allow the donor fluorophore 520 to transfer energy to the acceptor fluorophore 522. This energy transfer activates the acceptor fluorophore 522 so that it emits at its characteristic wavelength, thereby generating a detectable signal. A probe without ligase 516 will detect the target RNA 506 but eventually they may separate again by thermal motions and the detectable signal will be reduced or eventually disappear completely. By adding a ligase 516, when the target mRNA 506 is bound, the nanoprobe 500 is modified so that DNA 502 is joined to DNA 504 so that there is a detectable signal from the acceptor 522, even if the target RNA 506 is no longer bound to the nanoprobe. A particular example of a ligase that can be used is T4 DNA ligase, which can join DNA in DNA/RNA hybrids (Engler and Richardson, (1982) P. D. Boyer (Eds.), *The Enzymes*, 5, pp. 3. San Diego: Academic Press.).

Nanoprobes can also be used to determine the sequence of a target nucleic acid molecule. FIGS. 8A-C shows nanoprobes (herein referred to as medusa nanoprobes) that can be used to sequence a nucleic acid molecule. As shown in FIG. 8A, the nanoprobe 550 includes a targeting moiety (polymerase 552) linked to multiple nucleotides 554, 556, 558, 560 that cannot be added to a growing nucleic acid chain (such as a base that contains a non-hydrolyzable triphosphate) via molecular linkers 562. The nucleotides 554, 556, 558, 560 can be attached at the base, at the 3' hydroxyl of the sugar, at the 5' y phosphate or to any point on a nucleotide that does not interfere with specific nucleotide binding to the polymerase or complementary base pairing. The nucleotides 554, 556, 558, 560 can be different nucleotides (as shown in FIG. 8A), or can be the same nucleotides (in which case nanoprobes with each nucleotide would be included in the sequencing reaction). The polymerase 552 includes a donor fluorophore 564, and each nucleotide 554, 556, 558, 560 includes an acceptor fluorophore 566, 568, 570, 572. For example, if multiple types of nucleotides are on the same nanoprobe, each nucleotide can include a unique acceptor fluorophore.

A variation of the nanoprobe shown in FIG. 8A is shown in FIG. 8B. The nanoprobe 580 includes a polymerase 552 linked to multiple nucleotides 554, 556, 558, 560 via a molecular linker 562 composed of multiple molecular rods (for example 582) and tethers (for example 584). The nanoprobe 580 includes a donor fluorophore 564, and each nucleotide 554, 556, 558, 560 is associated with a different acceptor fluorophore 566, 572, 570, 568, respectively. In this example, primer 586 and target nucleic acid to be sequenced 588 are not part of the nanoprobe 580. However, if desired, primer 586 can be attached to the nanoprobe 580 via a molecular linker. Another variation is shown in FIG. 8C. The nanoprobe 590 includes a polymerase 552 linked to multiple nucleotides 554, 556, 558, 560 via a molecular linker 562 composed of molecular rods (for example 561, 563, 565, 569, 571, 575, 577, 581, 582) and tethers (for example 584, 567, 573, 579, 583, 585, 587, 589). The nanoprobe 590 includes a donor fluorophore 564, and each nucleotide 554, 556, 558, 560 is associated with a different acceptor fluorophore 566, 572, 570, 568, respectively. The primer 586 and target nucleic acid to be sequenced 588 are not part of the nanoprobe 590. However, if desired, primer 586 can be attached to the nanoprobe 580 via a molecular linker.

Nanoprobes can also be used to detect alternative splicing, for example as an alternative to molecular beacons. For example, a pair of nanoprobes with different acceptors can distinguish two alternative splice junctions (for example, this can be done with a nanoprobe containing three different molecular linkers). The nanoprobe can have long homology regions (high Tm) yet if it binds to a place which is not a target it gives no signal.

A nanoprobe that detected an alternative splice junction can be joined with a second nanoprobe on in the same molecule. For example, the left can include an upstream binding arm with a donor and the right can include two or more downstream binding arms with different acceptors. Such a probe can be generated using a single DNA to which and multiple "arms" are annealed by hybridization. For example, a molecular rod can include multiple tethers. The left-most tether is for the upstream part of a splice junction. The down stream two tethers are for the alternative splice junctions.

Exemplary Nanoprobes for Modification of Biomolecules

The present disclosure provides multiple examples of nanoprobes that can be used to modify one or more biomolecules. For example, such nanoprobes can be used to cleave a target biomolecule, for example to reduce the biological activity of the target biomolecule.

Figure 9:
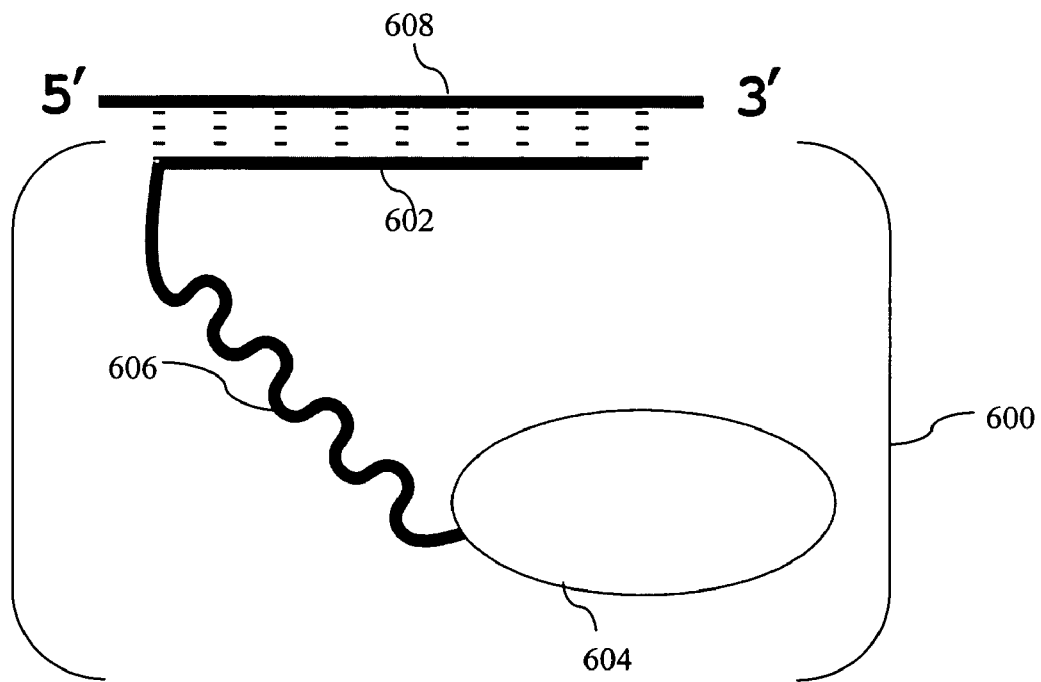
FIG. 9 is a schematic drawing showing an exemplary nanoprobe that includes antisense and RNase H functional groups, which can be used to destroy a target mRNA molecule.

One particular example of a nanoprobe that can be used to cleave a target RNA molecule (for example to inactivate the RNA) is shown in FIG. 9. The nanoprobe 600 includes two functional groups: a targeting moiety (an antisense oligonucleotide 602) and an activating moiety (RNase H 604). A molecular linker 606 (such as a tether) joins the antisense oligonucleotide 602 to the RNase H 604, wherein the antisense oligonucleotide 602 can hybridize to the RNA target 608. In the absence of the mRNA target 608 (not part of the nanoprobe), RNase H 604 will not cut the mRNA target, because RNase H cuts RNA only in RNA/DNA hybrids. However, in the presence of the mRNA target 608, the antisense oligonucleotide 602 finds the mRNA target 608 and will hybridize to the mRNA target. The RNase H 604 can then cleave the mRNA target 608 because the linker 606 holds them sufficiently close together for a sufficient period of time for the RNAse H to cut the RNA/DNA hybrid target.

One particular example of a nanoprobe that can be used to cleave a target protein (such as a DNA binding protein, for example a transcription factor) is shown in FIG. 10A. The nanoprobe 700 includes two functional groups: a targeting moiety (a dsDNA molecule 702) and an activating moiety (proteinase K 704). A molecular linker 706 (such as a tether) joins the dsDNA molecule 702 to the proteinase K 704, wherein the dsDNA molecule 702 includes a sequence that will specifically bind to the target protein 708 (not part of the nanoprobe). If desired, the nanoprobe 700 could also include a molecular rod (for example as part of the linker 706). In the absence of the target protein 708 (not part of the nanoprobe), the proteinase K 704 will not specifically cleave the protein target (though it may cleave proteins free in solution). However, in the presence of the target protein 708, the target protein 708 will specifically bind to the dsDNA 702, and be in close enough proximity to the proteinase K 704 such that the proteinase K 704 can then preferentially cleave the protein target 708, thereby significantly reducing the biological activity of the protein.

Another particular example of a nanoprobe that can be used to cleave a target protein (such as amyloids, virus or bacterial components) is shown in FIG. 10B. The nanoprobe 800 includes two functional groups: a targeting moiety (a protein binding agent 802) and an activating moiety (proteinase K or other proteinase 804). A molecular linker 806 joins the protein binding agent 802 to the proteinase 804, wherein the protein binding agent 802 (such as an antibody) specifically binds to the target protein 808 (not part of the nanoprobe). The molecular linker 806 includes tethers 810, 812 separated by a molecular rod 814.

In particular examples, the nanoprobe 800 can further include other activating moieties, such as a donor fluorophore 816 and an acceptor fluorophore 818, such as a donor fluorophore 816 attached to a tether 812 and an acceptor fluorophore 818 attached to another tether 810. In another example (not pictured), the probe 800 further includes a single-stranded nucleic acid molecule between tether 812 and the protein binding agent 802, as well as between tether 810 and the proteinase K 804. The donor fluorophore 816 is attached to an amino of a single stranded nucleic acid complementary to the single stranded nucleic acid molecule between tether 812 and the protein binding agent 802, and the acceptor fluorophore 818 is attached to an amino of a single-stranded nucleic acid complementary to the single stranded nucleic acid molecule between tether 810 and the proteinase K 804. The single-stranded nucleic acid molecules containing each fluorophore are hybridized to the nanoprobe, thereby attaching the fluorophores to the nanoprobe. One skilled in the art will appreciate that the positions of the donor and acceptor fluorophores can be reversed.

The molecular rod 814 ideally keeps the proteinase K 804 sufficiently separated from the protein binding agent 802, thereby reducing or preventing hydrolysis of the protein binding agent 802. When the target protein 808 (not part of the nanoprobe) is bound by the protein binding agent 802, it is held in place to be cleaved by the proteinase K 804. In particular examples, this cleavage can be observed by detecting a signal from an acceptor fluorophore. In the absence of the target protein 808, the donor and acceptor fluorophores 816, 818 will not be in sufficient proximity with one another to produce a detectable signal from the acceptor 818, and the proteinase K 804 will not be in sufficient proximity with the target protein 808 to degrade the target protein. In the presence of the target protein 808, the donor and acceptor fluorophores 816, 818 are in sufficient proximity with one another to produce a detectable signal from the acceptor 818, and the proteinase K 804 is in sufficient proximity with the target protein 808 to degrade the target protein. Therefore, detection of an emission signal from the acceptor fluorophore (or detection of loss of an emission signal from the donor fluorophore) indicates that the target protein is being cleaved.

In a particular example, the nanoprobe 800 shown in FIG. 10B can include a protein binding agent that specifically binds to proteinase K 804 (such as an anti-proteinase K antibody) on a tether that links the protein binding agent to the proteinase K, for example to reduce the biological activity of proteinase K (such as to reduce degradation of non-target biomolecules). However when the target protein 808 is bound to the protein binding agent 802, the protein binding agent that specifically binds to proteinase K 804 will sometimes not be bound to proteinase K, thereby releasing proteinase K, and permitting the proteinase K to cleave the target protein 808.

In particular examples, the disclosed nanoprobes that can modify a target biomolecule can be used as an alternative to siRNA-based gene silencing methods.

Exemplary Nanoprobes for Detecting and Modifying Biomolecules

The present disclosure also provides multiple examples of nanoprobes that can be used to both detect and to modify one or more biomolecules. For example, such nanoprobes can be used to detect a target biomolecule, for example quantitate an amount of the target biomolecule present, and also modify the detected biomolecules.

As described above, nanoprobe 800 shown in FIG. 10B can be used to detect cleavage of a target protein.

A variation of nanoprobe 600 in FIG. 9 is shown in FIG. 11. Similar to nanoprobe 600, nanoprobe 900 can be used to cleave a target mRNA molecule. However, nanoprobe 900 can also be used to quantitate an amount of mRNA present, for example to determine an amount of target mRNA present in a sample. The nanoprobe 900 in FIG. 11 includes activation moieties, a donor fluorophore 902 and acceptor fluorophore 904 that permit detection (and in some examples quantitation) of RNA as it is cleaved by the RNase 920 (such as RNase H). Nanoprobe 900 includes two antisense oligonucleotides 906, 908 that can specifically hybridize to a target RNA sequence 910 (not part of the nanoprobe), which are linked via a molecular linker that includes tethers 912, 914 that are joined by a molecular rod 916. A dsDNA molecule 918 is used to attach the RNase 920 via a tether 922. The nanoprobe 900 includes three molecules, which are hybridized to form the nanoprobe. The first molecule includes fluorophore 902, antisense oligonucleotide 906, tether 912, the bottom strand of molecular rod 916, and the top strand of dsDNA molecule 918. The second molecule includes fluorophore 904, antisense oligonucleotide 908, tether 914, and the top strand of molecular rod 916. When the first and second molecules are hybridized, this results in the formation of molecular rod 916. Therefore, the sequence of the top and bottom strands of molecular rod 916 are complementary. The third molecule includes the bottom strand of dsDNA molecule 918, tether 922, and RNase 920. When the first and third molecules are hybridized, this results in the formation of dsDNA molecule 918. Therefore, the sequences of the top and bottom strand of dsDNA molecule 918 are complementary.

The nonproven 900 includes a donor fluorophore 902 attached to the 5' end of antisense oligonucleotide 906 (such as the 5' nucleotide), and an acceptor fluorophore 904 attached to the 3' end of antisense oligonucleotide 908 (such as the 3' nucleotide). One skilled in the art will appreciate that the position donor and acceptor fluorophores can be reversed. In the absence of the mRNA target 910 (not part of the nonproven) there is little detectable signal from the acceptor fluorophore 904 (or alternatively, a strong, unquenched signal from the donor fluorophore 902). In addition, when RNase 920 is RNaseH, RNaseH will not cut any unbound mRNA target 910, because RNase H only cleaves RNA in RNA/DNA hybrids. However, as shown in FIG. 11, in the presence of the mRNA target 910 the antisense oligonucleotides 906, 908 specifically hybridize to the mRNA target 910, allowing the donor 902 and acceptor fluorophore 904 to be sufficient proximity to allow the donor fluorophore 902 to transfer energy to the acceptor fluorophore 904, thereby activating the acceptor fluorophore so that it emits at its characteristic wavelength, and generating a detectable signal. The detectable signal will be generated each time the nonproven 900 binds to the target RNA 910. In addition, when the antisense oligonucleotides 906, 908 specifically hybridize to the mRNA target 910, this brings the RNase 920 in sufficient proximity to the formed DNA/RNA hybrid between the mRNA target 910 and the antisense oligonucleotides 906, 908, so that the RNAse 920 can cleave the DNA/RNA hybrid, which will reduce or eventually eliminate the detectable signal. The nonproven 900 then can repeat the process on a new target RNA 910. Therefore, the cleavage of an mRNA is accompanied by a FRET signal burst, which can be monitored to count specific mRNA molecules. The mRNA molecules are destroyed after counting so there is no duplication. In particular examples, the total detectable signal is proportional to the number of destroyed target RNA molecules.

In addition, the nonproven 900 can be used to count specific kinds of splicing in the mRNA. For example, if the left half of the target RNA 910 is the 3' end of an exon and the right half is the 5' end of the next exon that have been joined by splicing, then the nonproven 900 will detect this particular splice alternative and generate a detectable signal from the acceptor fluorophore 904. Other splicing alternatives will not be detected. Therefore, nanoprobes that are specific for various alternative splice products (for example by having the sequences of the antisense oligonucleotides 906, 908 specific for each splice product to be detected) can be contacted with a sample, to determine which splice products are present in the sample. By including a different acceptor fluorophore 904 or combinations of acceptor fluorophores on each nonproven that each recognizes a particular splice product, two or more nanoprobes added to the sample can be differentiated by the different acceptor fluorophore signals produced. Therefore, the generation of specific alternative splicing products can be monitored in real time.

Purification of Bound Nanoprobes

In some examples, nanoprobes bound to their target molecule are purified. For example, the resulting complexes can be purified by applying the reaction mixture to a solid medium containing the target, such as a column containing beads coated with the target. This will remove free nonproven leaving in the flow-through nanoprobes complexed with the target. Such purification can in some examples reduce background. Alternativley, this can be done by conjugating the target to magnetic beads and removing excess nanoprobes by a magnet.

Generation of Nanoprobes

Many methods are available for generating the disclosed nanoprobes. For example, methods of attaching a fluorophore to another molecule are known. In addition, methods of generating DNA-PEG structures are known. Although particular methods are provided herein, the disclosure is not limited to these methods.

DNA/PEG Synthesis and Attachments

In examples where the molecular linker includes one or more DNA molecular rods and one or more PEG tethers, the following methods can be used. DNA of any desired sequence can be obtained from a variety of commercial sources (such as Invitrogen, Synthegen, Sigma). The sequence of the DNA can be determined using the NANEV program, which employs evolutionary methods for the design of nucleic acid nanostructure (Goodman et al., *BioTechniques*, 38:548-50, 2005). This program can be used to design DNA sequences in a nanoprobe so that only the desired structure forms by hybridization. In particular examples a PEG tether is incorporated as a standard phosphoramidite 'spacer' anywhere within the molecular linker. It is also possible to introduce an amino group anywhere in the DNA sequence.

By appropriate use of DNA-DNA hybridization, a nanoprobe can be constructed using only one amino group per DNA/PEG linker. This allows the amino group to be used to attach a fluorophore or protein on the nanoprobe, for example as shown in FIG. 5A.

DNA-Protein Conjugation Methods

A synthetic DNA containing an amino group can be attached to a protein via a unique cysteine (Kukolka and Niemeyer, *Org. Biomol. Chem.*, 2:2203-6, 2004) or a different chemically modified residue (Khidekel et al., *J. Am. Chem. Soc.*, 125:16162-3, 2003; Zhang et al., *Science*, 303: 371-3, 2004; and Klarmann et al., *Protein Expr. Purif.* 38:37-44, 2004).

In one example, a nanoprobe includes one antibody attached to a molecular linker. For example, the method of Kozlov et al. (*Biopolymers*, 73:621-30, 2004) can be used to make antibody-oligonucleotide conjugates. In addition, the complexes can be separated by the ratio of number of antibodies per oligonucleotide, to obtain those having a 1:1 ratio. A desired antibody that recognizes a target biomolecule can be attached to an oligonucleotide commercially (Biosyn, Lewisville, Tex.).

In one example, a single chain antibody (scFv) that recognizes a target biomolecule includes a Cys on the C-terminus (for example using the method of Hayashi et al., *Gene*, 160: 129-30, 1995), thereby allowing the antibody to be attached to an amino-modified oligonucleotide.

In another example, a monoclonal antibody that recognizes a target biomolecule (such as a commercially available monoclonal antibody), is attached to a molecular linker, for example by using the sugars on IgG antibodies to attach a PEG tether. The sugars are alkylated, and reduction and amination permits attachment of a PEG tether. In a particular example, one PEG tether is attached to the antibody.

In another example, a monoclonal antibody that recognizes a target biomolecule (such as a commercially available monoclonal antibody), is attached to a molecular rod, for example by using the two asparagine-linked oligosaccharides (one per chain) that has two mannose sugars connected to a GlcNAc and that GlcNAc is attached to another GlcNAc which is, in turn, attached to the asparagine residue at the Fc region of the antibody. The enzyme Endo-H (New England Biolabs) can be used to break the linkage between the two GlcNAc residues, leaving two GlcNAc residues (one per chain) attached to the asparagine residue of the Fc region of antibody. When oxidized, this reduces the number of attached PEG tethers to four. To reduce the number of tethers further, the Y286L mutant of the bovine Gal-T1 enzyme or Y289L mutant of the human Gal-T1 enzyme (Ramakrishnan and Qasba, *J. Biol. Chem.*, 277:20833-9, 2002) can be used to attach a modified galactose (Khidekel et al., *J. Am. Chem. Soc.*, 125:16162-3, 2003) resulting in only two PEG chains being attached to the antibody.

In an example where two PEG tethers are attached to an antibody, the PEG chains terminate in DNA strands that are complementary. When the PEG is attached, there are four possible combinations of DNA, but only two will anneal to each other. These are separable from the unannealed molecules. One of the two strands will continue with further PEG leading to the rest of the nanoprobe. Alternatively, the two tethers can have the same DNA part; these can be annealed to a DNA containing a direct repeat of the complementary sequence, which in turn is attached to the remainder of the nanoprobe. This approach allows for the use of commercially available antibodies.

In an example where an antibody that recognizes a target biomolecule is linked by multiple molecular rods, the nanoprobe is used to detect a DNA-binding protein. For example, a single antibody can have multiple PEG tethers attached thereto, followed by DNA. The DNA has a complementary strand and on the far end is the donor or acceptor fluorophore. The binding site for the protein is on the far end also (so that the double helix is a spacer).

A particular example of a method that can be used to attach one or more antibodies to a nanoprobe is provided in Martin and Papahadjopoulos (*J. Biol. Chem.* 257:286-8, 1982). Briefly, the method includes removing an Fc portion from an IgG using Pepsin. This generates two F(Ab')2 fragments. DTT is used to separate these, leaving a unique —SH group on each. Maleimidophenyl can be used to connect the —SH group to the nanoprobe (for example to a PEG tether or a rod) as described in Martin et al. (*Biochemistry*, 20:4229-38, 1981).

Methods of Using Nanoprobes to Detect Target Biomolecules

The disclosed nanoprobes can be used to detect biomolecules in vivo, ex vivo, in vitro or in situ. In particular examples, such methods are used to diagnose a disease, for example a disease that is caused by one or more known mutations in a target biomolecule. In some examples, the nanoprobe is attached to a surface, to provide a rapid-flow, reusable, parallel-detection method.

In particular examples, the method includes contacting a sample with one or more of the disclosed nanoprobes under conditions sufficient for one or more (such as two or more) functional groups to specifically interact with the target biomolecule, wherein interaction of the functional groups results in the production of a detectable signal by a label on the probe. The signal is detected, wherein the presence of a detectable signal indicates that the probe interacted with target biomolecule. This indicates that the target biomolecule is present in the sample. In contrast, the absence of a detectable signal (for example a signal that is at least twice the background signal) indicates that the probe did not interact with the target biomolecule. This indicates that the target biomolecule is not present in the sample (or that the target biomolecule is sequestered, protected or destroyed).

In a particular example, the target biomolecule is a DNA binding protein. DNA binding proteins include the zinc finger proteins, helix-turn-helix proteins, and leucine zipper proteins. Particular examples include, but are not limited to: p53, Tus, Fis, Lambda repressor, and Lac repressor. In this example, one functional group can include a protein binding agent (such as an antibody or protein that specifically binds to the DNA binding protein), and another functional group can include a nucleic acid sequence that can specifically bind to the DNA binding protein. For example, as shown in FIG. 2B, the nanoprobe 50 can be used to detect a DNA binding protein 62. When the DNA binding protein 62 binds to the binding sites 56 and the protein binding agent 52 binds to the DNA binding protein 62, the donor 58 fluorophore and acceptor 54 fluorophore are brought close enough to create FRET 64, which results in an emission signal 66 from the acceptor fluorophore 54 that can be detected. In contrast, in the absence of the DNA binding protein 62, there is no significant acceptor emission signal 66.

In a particular example, the probe includes a donor and an acceptor fluorophore, wherein interaction of the functional groups brings the donor and acceptor fluorophores into proximity to permit excitation of the acceptor fluorophore by resonance with the excited donor fluorophore. In this case, detecting the signal can include detecting the fluorescent signal emission from the acceptor fluorophore or detecting a decrease in the fluorescent signal emission from the donor. In a particular example, the acceptor fluorophore is a quencher, and interaction of the functional groups brings the donor and acceptor fluorophores into proximity to permit quenching of the donor fluorophore emission by the acceptor quencher. In this case, detecting the signal can include detecting a decrease in the fluorescent signal emission from the donor fluorophore.

In examples where the probe includes a donor and an acceptor fluorophore, the method can include exposing the sample to a light source, such as a laser, at the appropriate wavelength to excite the donor fluorophore. However, if the donor fluorophore is replaced or excited by a chemiluminescent molecule, the laser can be omitted.

The sample can include any biological sample that may contain the target biomolecule. For example, the sample can include a cell extract that contains one or more proteins or nucleic acid molecules. If desired, the proteins and nucleic acid molecules can be in a purified or concentrated form. In a particular example, the sample is a tissue section, such as a tissue slice. For example, a tissue array that includes specimens from many different subjects permits screening of a large number of such specimens, for example simultaneously. In one example, if detection of a nucleic acid molecule is desired, the sample can be exposed to one or more proteases. If desired, agents can be subsequently added to substantially neutralize the proteases, or the proteases can be removed. In another example, if detection of a protein is desired, the sample can be exposed to one or more nucleases. If desired, agents can be subsequently added to substantially neutralize the nucleases, or the nucleases can be removed. In some examples, the sample includes one or more cells that may contain the target biomolecule. In such examples, the sample is exposed to the probe under conditions that permit the probe to enter the cell. In particular examples, the nanoprobe is present in a liposome, thereby permitting entry of the nanoprobe into the cell.

In particular examples, the sample is obtained from a subject. A biological sample from a subject (such as a cheek swab) can be used directly, or can be manipulated, such as concentrated or purified. In one example, proteins or nucleic acid molecules are purified from the sample, prior to contact with the probe.

In some examples, one or more of the disclosed nanoprobes is administered to a subject, and the detection performed in vivo. For example, the nanoprobe can be administered on or under the skin, and a light source (such as a laser) directed to the skin, and the resulting fluorescence detected. In some examples where the detection is in vivo, one or more nanoprobes are introduced into a live cell, for example using a liposome. Upon introduction of a nanoprobe into a cell, it should take only seconds (or less) to detect (or modify) the target biomolecule.

One particular type of detection includes sequencing of a target nucleic acid molecule. In particular examples, one or more nanoprobes are used to sequence a target nucleic acid sequence. For example, referring to FIG. 8A, the method can include contacting a target nucleic acid sequence 574 with an oligonucleotide primer 576 and a nanoprobe 550 (or those shown in FIGS. 8B and 8C), in the presence of a mixture of non-labeled hydrolysable nucleotides. In the absence of a nucleic acid molecule to be sequenced 574 (not part of the nanoprobe) there is little detectable signal. When the polymerase 552 is bound to a target nucleic acid sequence 574 at a primer 576, a base 578 is exposed on the template strand 574. The nucleotides 554 556 558 560 at the ends of the molecular linkers 562 compete for binding to base 578, but only one of the four nucleotides (in this case 554) will be complementary to the exposed base 578. The non-complementary bases (in this case 556 558 560) will quickly dissociate, but the complementary base 554 will dwell for a substantial time in the binding pocket of the polymerase 552. During this time, the corresponding acceptor fluorophore 566 on the complementary base 554 will be in sufficient proximity to the donor fluorophore 564 attached to the polymerase 552 for FRET to occur, producing a characteristic acceptor emission signal. All of the nucleotides 554 556 558 560 will diffuse in and out of the active site, but the linker 562 with the base that is complementary to the template will dominate the signal because it occupies the active site the longest. Thus the nanoprobe will report the next base that would be incorporated into the target nucleic acid sequence 574, but since the nucleotides 554 556 558 560 cannot be added to a growing nucleic acid chain, no reaction will take place. A small concentration of hydrolysable dNTPs (or NTPs for an RNA polymerase) is provided in the reaction solution. The appropriate hydrolysable dNTP will eventually be incorporated into the nascent strand 576 and the nanoprobe 550 will step forward one position. This exposes the next complementary base and so a (possibly) different acceptor fluorophore signal will be emitted. The varying acceptor fluorophore signals correspond to the nucleotide sequence.

Methods of Using Nanoprobes to Modify Target Biomolecules

The disclosed nanoprobes can be used to modify biomolecules in vivo, ex vivo, in vitro or in situ. In particular examples, such methods are used to treat a disease, for example a disease that is caused by the undesired expression of a target biomolecule. For example, the disclosed nanoprobes can be used to cleave a target biomolecule, thereby reducing the biological activity or even inactivating the target biomolecule.

In particular examples, the method includes contacting a sample with one or more of the disclosed nanoprobes under conditions sufficient for the functional groups to specifically interact with the target biomolecule, wherein this interaction results in the modification of the target biomolecule. In particular examples, the method further includes detecting the modification of the target biomolecule, for example by detecting a signal generated by a label on the probe. For example, if the probe includes a donor and an acceptor fluorophore, interaction of the functional groups brings the donor and acceptor fluorophores into a proximity to permit excitation of the acceptor fluorophore by the donor fluorophore. In this case, detecting the signal can include detecting the fluorescent signal emission from the acceptor fluorophore.

In examples where the probe includes a donor and an acceptor fluorophore, the method can include exposing the sample to a light source, such as a laser, at the appropriate wavelength to excite the donor fluorophore. However, if the donor fluorophore is replaced by a chemiluminescent molecule, this step can be omitted.

In a specific example, one of the functional groups includes a nucleic acid sequence that can specifically hybridize to a target nucleic acid, thereby forming a complex, and one of the functional groups includes a protein that can cleave the complex. Upon hybridization of the nucleic acid sequence to the target biomolecule, for example forming a DNA/RNA complex, the protein (such as RNase), can cleave the complex.

As described above, the sample can include any biological sample that may contain the target biomolecule.

Methods of Using Nanoprobes for Treatment

The disclosed nanoprobes can be used to treat a subject having a disorder related to a target biomolecule. In particular examples, the methods are used to treat a disease, for example a disease that is caused by the undesired expression or biological activity of a target biomolecule. For example, the disclosed nanoprobes can be used to cleave a target biomolecule, thereby reducing the biological activity or even inactivating the target biomolecule.

In particular examples, the method includes administering a therapeutic amount of one or more of the disclosed nanoprobes to a subject, wherein the subject has a disorder that can be treated by decreasing the activity or expression of the target biomolecule. In some examples, the nanoprobe includes a protease or nuclease (such as RNAase) as one of the functional groups, and another functional group that can specifically bind to or hybridize to the target biomolecule.

Any mode of administration can be used, and the method can be determined by a skilled clinician.

EXAMPLE 1

Nanoprobe for Detecting DNA Binding by a Protein

This example describes a nanoprobe that includes as functional groups an agent that can specifically bind to a DNA binding protein (such as an antibody or a protein) and a nucleic acid molecule. Such a nanoprobe can be used to detect protein binding to a DNA molecule. Although particular functional groups are described for the detection of p53 binding to a target nucleic acid sequence, one skilled in the art will recognize that other p53 detection agents and other p53 target nucleic acid sequences can be used to detect the DNA/p53 protein interaction. Similarly, one skilled in the art will recognize that other binding agents and other nucleic acid sequences can be used to detect the DNA/protein interaction of interest.

FIG. 2A shows an exemplary nanoprobe that can be used to detect binding of p53 to a target nucleic acid sequence. For example, the protein binding agent 52 can be an anti-p53 antibody, and the protein binding site(s) 56 is a nucleic acid sequence that specifically binds to p53.

Antibodies that specifically bind to p53 are commercially available, or can be made using routine methods in the art. Particular examples of commercially available p53 antibodies include, but are not limited to, those shown in Table 2 (all available from Calbiochem):

TABLE 2 p53 antibodies

| Anti-p53 Abs | Anti-p53 Antibodies that detect phosphorylation at particular Serines | Fluorescein - anti-p53 conjugates |
|---|---|---|
| OP03 Anti-p53 (Ab-1) (Pantropic) Mouse mAb (PAb421) | PC386 PhosphoDetect ™ Anti-p53 (pSer15) (Ab-3) Rabbit pAb | OP03F Anti-p53 (Ab-1) (Pantropic) Mouse mAb (PAb421) Fluorescein Conjugate |
| OP104L Anti-p53 (Ab-11) (Pantropic) Mouse mAb (PAb1802) | PC461 PhosphoDetect ™ Anti-p53 (pSer15) (Ab-6) Rabbit pAb | OP43F Anti-p53 (Ab-6) (Pantropic) Mouse mAb (DO-1) Fluorescein Conjugate |
| OP140 Anti-p53 (Ab-12) (Pantropic) Mouse mAb (DO-7) | DR1023 PhosphoDetect ™ Anti-p53 (pSer20) Rabbit pAb | |
| OP09 Anti-p53 (Ab-2) (Pantropic) Mouse mAb (PAb1801) | PC387 PhosphoDetect ™ Anti-p53 (pSer392) (Ab-4) Rabbit pAb | |
| OP29 Anti-p53 (Ab-3) (Mutant) Mouse mAb (PAb240) | PC387T PhosphoDetect ™ Anti-p53 (pSer392) (Ab-4) Rabbit pAb | |
| OP32 Anti-p53 (Ab-4) (Wild type) Mouse mAb (PAb246) | 506133 PhosphoDetect ™ Anti-p53 (pSer392) Mouse mAb (9F4) | |
| OP33 Anti-p53 (Ab-5) (Wild type) Mouse mAb (PAb1620) | DR1024 PhosphoDetect ™ Anti-p53 (pSer46) Rabbit pAb | |
| OP43 Anti-p53 (Ab-6) (Pantropic) Mouse mAb (DO-1) | | |
| PC35 Anti-p53 (Ab-7) (Pantropic) Sheep pAb | | |
| OP73 Anti-p53 (Ab-8) (Pantropic) Mouse mAb (BP53.12) | | |

Both p53 activating and non-activating antibodies can be used. When a nanoprobe includes a p53 activating antibody, the nanoprobe can detect activated or non-activated p53 binding DNA. In contrast, if the nanoprobe includes a p53 antibody that does not activate p53, only previously activated p53 can be detected by its binding to the nanoprobe. In one example, the nanoprobe includes p53 antibodies that can detect different phosphorylation and acetylation modifications of the p53. In yet another example, the nanoprobe includes p53 antibodies that specifically bind to wild-type or mutated p53, permitting the detection of a particular p53 mutation. Particular examples of p53 antibodies that can be used include, but are not limited to: pAb421, and those available from Biodesign International (Saco, Me.), Calbiochem (San Diego, Calif.) and Epitomics (Burlingame, Calif.).

As an alternative to using an antibody as the protein binding agent 52 (FIGS. 2A and 2B), a p53-binding protein can be used. Examples of p53 binding proteins that can be used include, but are not limited to: p53BP1, p53BP2, MDM2, Rad51, TBP, P300, SRC1, BRCA1, and ACTr. Such proteins can be made recombinantly using standard molecular biology methods. For example, Origene (Rockville, Md.) commercially provides clones that can be used to produce the following p53 binding proteins: TC116621 NM__005657 Homo sapiens tumor protein p53 binding protein, 1 (TP53BP1); TC111040 NM__005426 Homo sapiens tumor protein p53 binding protein, 2 (TP53BP2), transcript variant 2; TC108990 NM__007294 Homo sapiens breast cancer 1, early onset (BRCA1), transcript variant BRCA1a; TC123899 NM__007296 Homo sapiens breast cancer 1, early onset (BRCA1), transcript variant BRCA1a'; TC108993 NM__007297 Homo sapiens breast cancer 1, early onset (BRCA1), transcript variant BRCA1-delta2-10; TC115590 NM__007306 Homo sapiens breast cancer 1, early onset (BRCA1), transcript variant BRCA1-exon4; and TC118660 NM__002392 Homo sapiens Mdm2, transformed 3T3 cell double minute 2, p53 binding protein (mouse) (MDM2), transcript variant MDM2.

The protein binding site(s) 56 that include a nucleic acid sequence that specifically binds to p53, can include at least one binding site, such as at least two, or at least three binding sites, for example 1, 2, 3, 4, or 5 binding sites. One particular example of a protein binding site sequence that can be used to detect p53 includes, but is not limited to:

(SEQ ID NO: 4)
GGACATGTCCGGAGATGTCCGCGAAGCGGACATGTCCGGACATGTCC.

In one example, the protein binding site(s) 56 includes at least two binding sites. For example, when a DNA binding protein 62 such as p53 has two adjacent sites that overlap, only one can be bound at a time, so the effective binding constant is doubled. As shown in FIG. 2A, each half binding site 56 is represented by a rectangle with a cross (so there are two distinct overlapping DNA binding sites shown in FIG. 2A). Each rectangle in one example represents half of a p53 site. p53 could bind to the left and middle as shown in FIG. 2B, or to the middle and right rectangles.

In a particular example, a nanoprobe that can be used to detect p53 is generated as follows. The protein binding agent 52 (such as an antibody) is attached to a PEG tether 60 of oligonucleotide containing p53 binding sites (such as SEQ ID NO: 4) by using a bifunctional cross-linker, such as succinimidyl 4-hydrazinonicotinateacetone hydrazone (SANH), EDC (1-ethyl-3-[3-dimethylaminopropyl]carbodiimide hydrochloride), or AMAS (N-(α-Maleimidoacetoxy) succinimide ester) (for example for amine-sulfhydryl cross-linking). For example the protein binding agent 52 includes a Cys, and the PEG includes an $NH_2$ group on the end, the $NH_2$ and Cys can be linked using AMAS as follows. Briefly, the protein binding agent 52 is dissolved in the manufacturer's Conjugation Buffer at 0.1 mM (such as 5 mg in 1 ml for a 50 kDa protein). The cross-linker is added to the protein binding agent 52 at 1 mM final (=10-fold molar excess) by dissolving 2.52 mg AMAS in 1 ml DMSO (makes 10 mM) and then adding 100 μl/ml of protein binding agent 52. The mixture is incubated for 30 minutes at room temperature or 2 hours at 4° C. Excess cross-linker is removed using a desalting column equilibrated with Conjugation Buffer. The commercial desalting column product instructions allow one to determine which fractions contain protein binding agent 52. Alternatively, the protein binding agent 52 can be located by measuring for fractions having peak absorbance at 280 nm; however, the NHS-ester leaving group also absorbs strongly at 280 nm. The protein binding agent 52-SH and desalted protein binding agent 52-$NH_2$ are combined and mixed in a molar ratio corresponding to that desired for the final conjugate and consistent with the relative number of sulfhydryl and activated amines that exist on the two proteins. Incubate the reaction mixture at room temperature for 30 minutes or 2 hours at 4° C. However, there is generally no harm in allowing the reaction to proceed for several hours or overnight, although usually the reaction will be complete in the specified time. To terminate the conjugation reaction before completion, add buffer containing reduced cysteine at a concentration several times greater than the sulfhydryls of antibody-SH.

A FRET pair will be placed on the protein binding site and the p53-binding agent (such as an antibody or protein) 58 such that proximity of the fluorophores will produce a characteristic signal after p53 binds to the DNA.

EXAMPLE 2

Nanoprobe to Detect Antigenic Compounds

This example describes a nanoprobe that includes as functional groups agents that can specifically bind to a protein (such as an antibody or a protein). Such a nanoprobe can be used to detect one or more target proteins. Although particular functional groups are described for the detection of p53 (for example total p53 concentration independent of p53 binding ability), one skilled in the art will recognize that other specific binding agents can be used to detect p53. Similarly, one skilled in the art will recognize that other binding agents can be used to detect the target protein of interest.

In a particular example, the nanoprobe shown in FIG. 3A includes anti-p53 antibodies as the protein binding agents 102, 104 that are connected by a PEG tether 110. In a particular example, the anti-p53 antibodies are pAb421, or those available from Biodesign International (Saco, Me.), Calbiochem (San Diego, Calif.) (see Table 2) and Epitomics (Burlingame, Calif.). One antibody 102 carries a donor fluorophore 106 and the other antibody 104 carries an acceptor fluorophore 108 of a FRET pair. In a particular example, the donor fluorophore 106 is FAM and the acceptor fluorophore 108 is Texas Red.

In one example, the nanoprobe 100 is used for detecting modified proteins. Antibodies specific to a modified protein can distinguish between the wild type and a modified protein. For example, anti-phospho-p53 and anti-acetylated-p53 antibodies are available from commercial sources (such as Cell Signaling Technology, Inc. and Calbiochem). Using these antibodies, whether or not p53 has been activated and the specific way in which p53 has been activated can be determined.

In a particular example, a nanoprobe that can be used to detect an antigenic compound is generated as follows. The protein binding agents 102, 104 are attached to a PEG tether 110 by using a bifuncational cross-linker, such as succinimidyl 4-hydrazinonicotinateacetone hydrazone (SANH), EDC (1-ethyl-3-[3-dimethylaminopropyl]carbodiimide hydrochloride), or AMAS (N-(α-Maleimidoacetoxy) succinimide ester), for example using the method described in Example 1.

A donor fluorophore is attached to one of the protein binding agents and the acceptor fluorophore is attached to the other protein binding agent. In one example, antibodies are labeled with a fluorophore using a commercially available kit, using the manufacturer's instructions (for example from Pierce, Rockford, Ill.).

The FRET pair will produce a characteristic signal upon binding of the protein binding agents 102, 104 to the antigenic compound, such as p53.

EXAMPLE 3

Nanoprobes with a DNA Separation Rod

This example describes a nanoprobe that includes a DNA sequence as the molecular rod. Such a nanoprobe can be used to detect a target antigenic compound, such as a protein.

Although particular DNA molecular rods are described, one skilled in the art will recognize that variations can be made. For example, the length of the molecular rod can be changed, and the exact sequence of the DNA can be changed.

In a particular example, the nanoprobe 200 shown in FIG. 4A is used to detect p53. For example, the nanoprobe 200 can include anti-p53 antibodies as the protein binding agents 202, 204 that are connected by a molecular rod that includes a PEG tether 210, 212 (each tether is 2-4 units of Spacer 18) separated by a dsDNA molecular rod 214 of 40 nucleotides (such as GACGCTAGTATCTTATGAAGCTTTCCT-GACTGCGGCATTA (SEQ ID NO: 5) hybridized to its complementary strand). In a particular example, the donor fluorophore 206 is 6-FAM and the acceptor fluorophore 208 is Texas Red.

In a particular example, the nanoprobe shown in FIG. 4A is generated by synthesizing half-nanoprobe molecules, which are then joined together by annealing complementary single stranded DNAs to form the molecular rod 214. Half-nanoprobe molecules are synthesized that have (1) —$NH_2$ or —SH groups on the terminus for attachment to an antibody, (2) one or more fluorescently labeled nucleotides (all donor or acceptor for a particular half-nanoprobe), (3) PEG linkers, and (4) 40 bases (for example) of unique DNA sequence (single copy sequence). Two such half-nanoprobes are constructed that have complementary single copy DNA sequences. After each half-nanoprobe is attached to a corresponding antibody, the two half-nanoprobes are annealed to create the full nanoprobe (FIG. 4A).

For example, the molecule $NH_2$-[PEG18][PEG18]-GACGCTAGTATCTTATGAAGCTTTCCT-GACTGCGGCATTA (SEQ ID NO: 6) and the molecule $NH_2$-[PEG18][PEG18]-TAATGCCGCAGTCAG-GAAAGCTTCATAAGATACTAGCGTC (SEQ ID NO: 7) are generated (for example by Integrated DNA Technologies), wherein [PEG18] is 1 unit of Spacer 18 (Integrated DNA Technologies). The antibodies are attached to the $NH_2$ group, and the two molecules incubated under conditions that permit the two complementary DNA strands to hybridize, thereby generating the nanoprobe shown in FIG. 4A. Exemplary incubation conditions include overnight incubation in binding buffer (100 mM NaCl, 10 mM Tris HCl pH=7.5, 100 µM EDTA) at room temperature.

The 40 bases of DNA separate the fluorescent donor from the acceptor well beyond the FRET limit. Bases are 3.38 Å thick so 40 base pairs are 135 Å long, which is greater than the typical FRET distance. However, the exact length used can be varied. Commercially available 18-atom PEG spacers are 23 Å long, so 2-4 of them are sufficient to bring the antibodies together at the center of the nanoprobe. This can significantly reduce the background FRET signal. Yet, when the two antibodies bind to a common target biomolecule, the FRET signal will be enhanced. By using multiple fluorescent nucleotides, the signal can be enhanced and become less sensitive to bleaching.

EXAMPLE 4

Nanoprobes with Further Separated Functional Groups

This example describes a nanoprobe that includes two or more tethers and two or more molecular rods, for example to permit further separation of the functional groups from one another. Although particular functional groups and molecular rods are described, one skilled in the art will appreciate that others can be used. For example, different antibodies can be used to detect the target biomolecule of interest.

FIG. 5A shows a nanoprobe 300 that further separates the protein binding agents 302, 308 in the absence of the target biomolecule. In a particular example, the protein binding agents 302, 308 are anti-p53 antibodies (for example see Example 1), the molecular rods 306, 312, 318 are dsDNA molecules (such as 40 nucleotides, for example SEQ ID NO: 5 hybridized to its complementary strand), and the tethers 314, 316 are PEG (such as 2-4 units of Spacer 18). A single amino group on the end of the molecular rods 306, 312, 318 can be used to attach the fluorophores 304, 310. For example Texas Red®-X NHS Ester (IDT) can be attached to an amino-modified oligonucleotide (Integrated DNA Technologies).

In addition, a single amino group on the end of the molecular rods 306, 312 can be used to attach the antibodies 302, 308. An antibody can be cross-linked to an amino group containing DNA by the following method. Briefly, a 5'-aldehyde group is introduced into molecular rods 306, 312, for example using 5'-aldehyde-modifier C2 phosphoramidite (Glen Research). The antibodies are reconstituted to a final concentration of 0.5 mg/mL in PBS. The antibodies are concentrated to 2 mg/mL in PBS, using a 50 000 MWCO Microcon filtration device (Millipore). Then, 20 mole equivalents of succinimidyl 4-hydrazinonicotinateacetone hydrazone (SANH; Solulink) prepared in DMF is added to the 2 mg/mL antibody solution and incubated in the dark at room temperature for 2.5 hours. Purification is performed by size exclusion chromatography using a NAP-5 column pre-equilibrated with 100 mM citrate buffer, pH 6.0, 150 mM NaCl. The eluent is concentrated in a 50 000 MWCO spin filter and the filter washed once with citrate buffer. The modified antibody is resuspended to 1 mg/mL in citrate buffer. To produce DNA—antibody conjugates, an oligonucleotide modified with an aldehyde moiety at the 5' end are added to the antibody solution at a minimum ratio of 10:1, DNA/Ab. The reaction is carried out overnight at room temperature.

Restriction sites can be placed in the dsDNA sequences 306, 312, 318 (for example to help characterize the nanoprobe to ensure it was properly constructed).

In a particular example, the nanoprobe shown in FIG. 5A is generated as follows. For example, the following molecules can be produced by Integrated DNA Technologies or Midland Certified Reagent Company, Inc., Midland, Tex.:

```
                                            (SEQ ID NO: 8)
1. GTGCCGTCGAATTCTCGCTA-[6-FAM]

(SEQ ID NO: 9)
2. [NH2]-TAGCGAGAATTCGACGGGAC-[PEG18][PEG18]-
GACGCTAGTATCTTATGAAGCTTTCCTGACTGCGGCATTA (SEQ ID NO: 10)
3. [NH2]-CGATAGGGATCCATTACTGC-[PEG18][PEG18]-
TAATGCCGCAGTCAGGAAAGCTTCATAAGATAGTAGCGTC (SEQ ID NO: 11)
4. GCAGTAATGGATCCCTATCG-[Texas Red]
```

[PEG18] is 1 unit of Spacer 18 (Integrated DNA Technologies). Molecule 1 will hybridize to molecule 2, molecule 3 will hybridize to molecule 4, and molecules 2 and 3 will hybridize, due to the complementarity of the nucleic acid sequences. Antibody 302 is attached to the $NH_2$ group of molecule 2, and antibody 308 is attached to the $NH_2$ group of molecule 3. After attaching the antibodies, the four molecules are incubated under conditions that permit the complementary DNA strands to hybridize, thereby generating the nanoprobe shown in FIG. 5A. Exemplary incubation conditions include overnight incubation in binding buffer (100 mM NaCl, 10 mM Tris HCl pH=7.5, 100 µM EDTA) at room temperature.

In one example, instead of using an $NH_2$ group to attach an antibody to an oligonucleotide sequence, the method of Niemeyer et al. is used (*Nucleic Acids Res.* 22:5530-9, 1994) or Kozlov et al. (*Biopolymers* 73:621-30, 2004) (all herein incorporated by reference as to these methods). In yet another example, to attach an antibody to an oligonucleotide, a single chain antibody (scFv) having a Cys on the C-terminus is attached to an amino-modified oligonucleotide (for example see Hayashi et al. *Gene.* 160(1):129-30, 1995)

EXAMPLE 5

Nanoprobes for Detecting Interactions Between Two Targets

This example describes a nanoprobe that includes at least two different protein binding agents, wherein each protein binding agent recognizes different target biomolecules that can interact. Although particular functional groups, molecular rods, and tethers are described, one skilled in the art will appreciate that others can be used. For example, different antibodies can be used to detect the target biomolecules of interest.

FIG. 5C shows how the nanoprobe 300 of FIG. 5A can be used to detect a protein complex that is the target biomolecule 320 (not part of the nanoprobe). The protein complex 320 includes at least two different biomolecules 328, 330 that can interact, thereby forming a detectable complex. The nanoprobe 300 includes protein binding agents 302, 308 which are antibodies that each specifically bind to two members of a protein complex. Particular examples of protein complexes, and the corresponding antibodies that can be used in the nanoprobe, are listed in Table 3. The molecular rods and tethers can be as described in Example 4.

TABLE 3

Exemplary protein complexes that can be detected with the disclosed nanoprobes, and the antibodies that can be used.

| Protein Complex | Antibodies* |
|---|---|
| p53-p53BP1 | Anti-p53 Binding Protein 1 Mouse mAb (BP13) |
| p53-BRCA1 | Anti-BRCA1 (Ab-1) Mouse mAb (MS110) |
| p53-Mdm2 | Anti-MDM2 (Ab-1) Mouse mAb (IF2) |
| p53-p300 | Anti-APC (Ab-1) Mouse mAb (FE9) |
| p53-SV40 T antigen | Anti-SV40 T Antigen (Ab-1) Mouse mAb (PAb419) |

*All available from EMD Biosciences, Inc., San Diego, CA. Particular examples of p53 antibodies are provided in Table 2.

The nanoprobe shown in FIG. 5C can be generated using the methods disclosed in Example 4, wherein the antibodies are selected for their ability to specifically bind to a particular member of the target biomolecule complex.

EXAMPLE 6

Nanoprobes for Detecting DNA

This example describes a nanoprobe that can be used to detect DNA, for example in vivo, in situ, or in vitro. Although particular sequences are described, one skilled in the art will recognize that other sequences can be used to detect any target biomolecule of interest, and the sequence of such molecules can be determined by those skilled in the art. In addition, although this example describes a molecule to detect DNA, one skilled in the art will appreciate that similar methods can be used to construct a nanoprobe that can detect mRNA.

A variant of the nanoprobe 400 shown in FIG. 6 is shown in FIG. 12A. The nanoprobe 1000 shown in FIG. 12A includes a dsDNA rod 1002 with PEG tethers 1004, 1006 at both ends of the molecular rod 1002. As shown in FIG. 12A, the dsDNA rod 1002 can be different lengths, such as 20 nucleotides (m), 30 nucleotides (nml), or 40 nucleotides (onmlk). Attached to the PEG tethers 1004, 1006 are antisense oligonucleotides 1008, 1010. To each of the oligonucleotides 1008, 1010, an oligonucleotide 1012, 1014 complementary to at least a portion of oligonucleotides 1008, 1010 is hybridized, respectively. One of the complementary oligonucleotides 1012 includes a donor fluorophore 1016 and the other complementary oligonucleotide 1014 includes an acceptor fluorophore 1018. In a particular example, the donor fluorophore 1016 is 6-FAM and the acceptor fluorophore 1018 is Texas Red.

In one example, the nanoprobe shown in FIG. 12A is used to detect the target sequence TCTATACGGATCCT-TACGCTCACCCAGTCTCGCGAATTCCGGCCTT (SEQ ID NO: 12) 1020 (not part of the probe). In such an example, the nanoprobe shown in FIG. 12A can be generated as follows. For example, the following molecules can be produced by Integrated DNA Technologies, Invitrogen, IBA GmbH (Germany) or Midland Certified Reagent Company, Inc. (Midland, Tex.).

```
                                           (SEQ ID NO: 13)
1. TAGCGAGAATTCGACGGCACAGCGTAAGGATCCGTATAGA-
[PEG18][PEG18][PEG18]-

GACGCTAGTATCTTATGAAGCTTTCCTGACTGCGGCATTA-
[PEG18][PEG18][PEG18]-

AAGGCCGGAATTCGCGAGACCGATAGGGATCCATTACTGC
(FIG. 12A, 1010, 1006, 1002, 1004, 1008).

(SEQ ID NO: 14)
2. [5' 6-FAM]-GTGCCGTCGAATTCTCGCTA
(FIG. 12A, 1014)

(SEQ ID NO: 15)
3. GCAGTAATGGATCCCTATCG-[3' Texas Red]
(FIG. 12A, 1012)

(SEQ ID NO: 16)
4. TAATGCCGCAGTCAGGAAAGCTTCATAAGATACTAGCGTC;

(SEQ ID NO: 17)
CCGCAGTCAGGAAAGCTTCATAAGATACTA;
or
                                           (SEQ ID NO: 18)
GTCAGGAAAGCTTCATAAGA.
```

Each of the molecule 4 sequences will hybridize to molecule 1, thereby producing a molecular rod of different lengths, depending which molecule 4 sequence is used. [PEG18] is 1 unit of Spacer 18 (Integrated DNA Technologies), wherein three units are about 7 nm long. Molecules 2 and 3 will hybridize to molecule 1, and molecule 4 will hybridize to molecule 1, due to the complementarity of the nucleic acid sequences. The four molecules are incubated under conditions that permit the complementary DNA strands to hybridize, thereby generating the nanoprobe shown in FIG. 12A. Exemplary incubation conditions include overnight incubation in THE binding buffer (50 mM NaCl, 10 mM Tris HCl pH=8.0, 1 mM EDTA) at room temperature. Molecule 1 (SEQ ID NO: 13) can be biotinylated to permit purification of the bound nanoprobe by streptavidin coated magnetic beads.

This design makes constructing variations of the nanoprobe possible, because different parts can be made separately and exchanged with other parts having different properties. For example, fluorophores can be easily replaced by resynthesizing the oligonucleotides 1014, 1012 (e.g. SEQ ID NOS: 14 and 15).

Figure 12B:
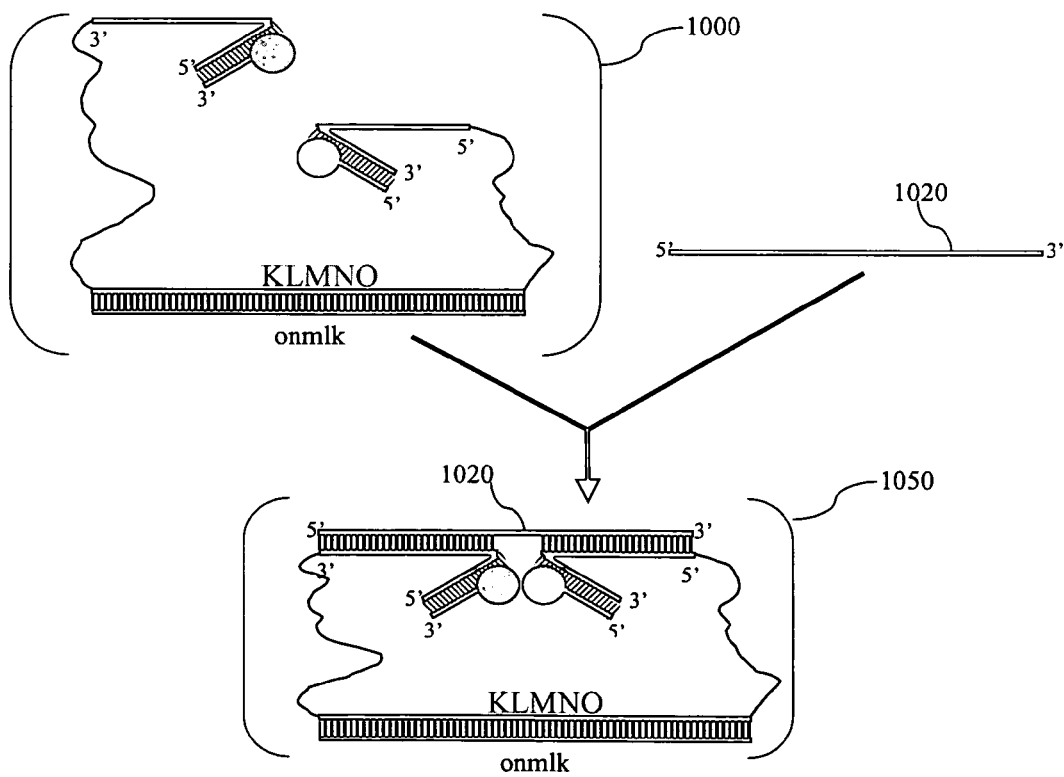
FIG. 12B is a schematic drawing showing how an exemplary nanoprobe 1000 can be used to detect a target mRNA molecule 1020, thereby forming a bound nanoprobe 1050.

The nanoprobe shown in FIG. 12A can be used to detect a target sequence (such as SEQ ID NO: 12) as shown in FIG. 12B. The nanoprobe 1000 can bind to the target 1020, thereby generating the bound nanoprobe 1050.

Figure 13A:
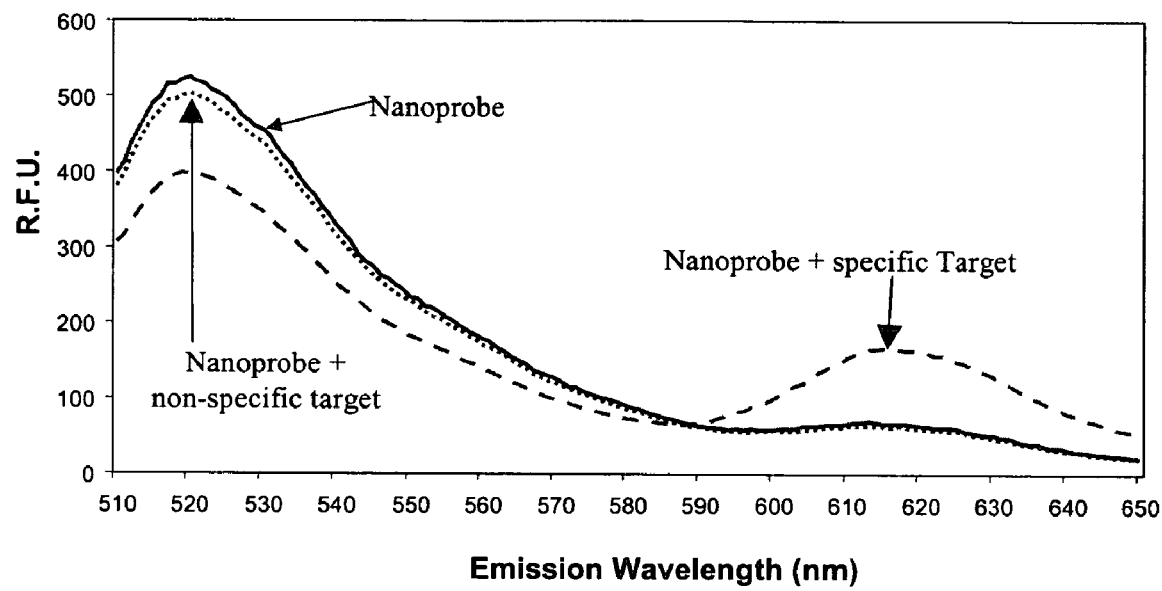
FIG. 13A is a plot showing the relative intensity of emission at different wavelengths for the two states of the nanoprobe of FIG. 12A (see FIG. 12B) in the presence or absence of the target sequence. The peak at 520 nm is 6-FAM emission and the peak at 620 nm is Texas Red emission.

The nanoprobe 1000 shown in FIG. 12A (1 µM) was incubated with (1) 1 µM of the target oligonucleotide (SEQ ID NO: 12), (2) 1 µM of a non-specific oligonucleotide (CCCG-GACGATATTGAACAATGGTTCACTGAA-GACCCAGGTCCAGATGAAGCT; SEQ ID NO: 96), or (3) with no DNA, in 20 µl 1xTNE buffer at room temperature for 1 hour, followed by emission scans (FIG. 13A). The spectra were measured on a SpectraMax Gemini EM microplate spectrofluorometer (Molecular Devices). Emission scans for a combination of 6-FAM and Texas Red fluorophores were made using the following parameters: excitation wavelength 470 nm, excitation cut-off filter wavelength 495 nm, emission wavelength range 505-650 nm.

As shown in FIG. 13A, when excited at 470 nm, the nanoprobe alone and nanoprobe incubated with non-specific target show both the 6-FAM donor emission at 520 nm and a low 615 nm emission background of the acceptor (Texas Red) excitation. In contrast, the nanoprobe incubated with the specific target shows decreased fluorescence at 520 nm and increased fluorescence at 615 nm caused by FRET between the donor and acceptor fluorophores that are kept close to each other by the target sequence. Therefore, the nanoprobe specifically recognizes the target oligonucleotide, but not a non-specific oligonucleotide.

That the appearance of the 615 nm FRET signal is mediated by DNA was confirmed by incubating the complexes with DNaseI. The nanoprobe (1 µM) 1000 was incubated with or without 1 µM of the target oligonucleotide (SEQ ID NO: 12) at room temperature overnight in TNE buffer. Half of each sample was treated with 0.2 u/µl DNaseI (2 u/µl, Ambion, Inc.) for 1 hour and emission spectra were scanned as described above.

Figure 13B:
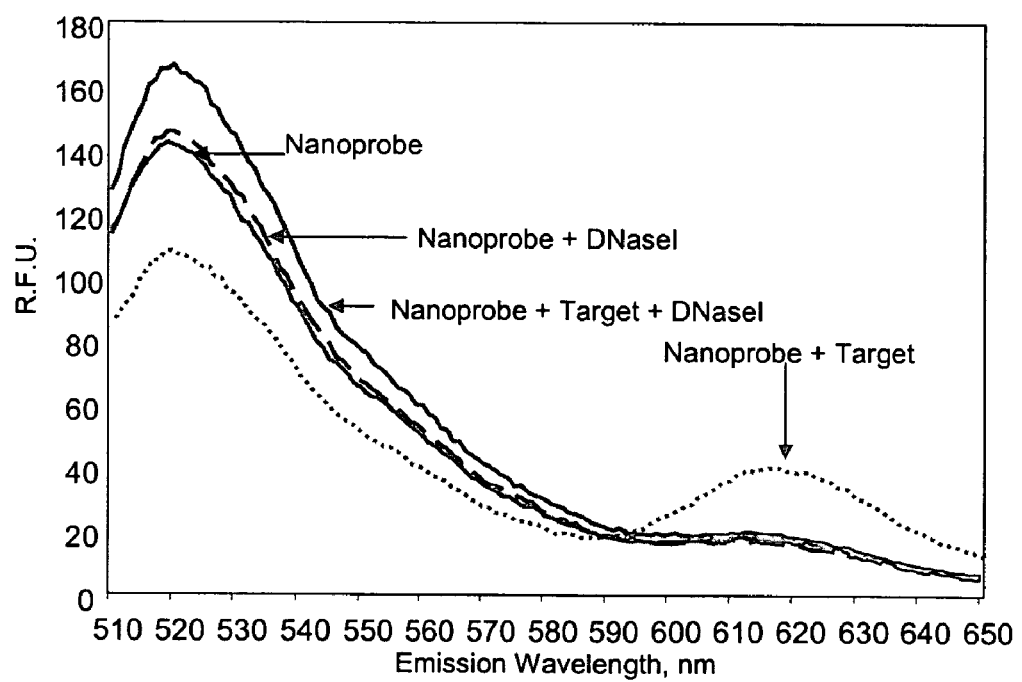
FIG. 13B is a plot showing the relative intensity of emission at different wavelengths for the two states of the nanoprobe of FIG. 12A (see FIG. 12B) in the presence or absence of the target sequence, and in the presence or absence of DNaseI. The peak at 520 nm is 6-FAM emission and the peak at 620 nm is Texas Red emission.

As shown in FIG. 13B, DNaseI added to the nanoprobe alone does not affect the emission spectrum because in the unbound state the donor and acceptor fluorophore are sufficiently apart and do not significantly interact. This is unchanged when the unbound nanoprobe is destroyed, completely separating the fluorophores. The nanoprobes form a complex with the target sequence resulting in 615 nm FRET emission. DNaseI treatment destroys the nanoprobe-target complex, and the 615 nm signal disappears. Therefore, the nanoprobe complex 1050 is sensitive to DNaseI, demonstrating that the observed FRET signal in FIGS. 13A and 13B is mediated by DNA contacts.

EXAMPLE 7

Universal Nanoprobe

This example describes methods that can be used to generate a universal nanoprobe. In particular examples, such a universal nanoprobe does not require rebuilding the entire "core" each time a new sequence is targeted. For example, the nanoprobe 2000 shown in FIG. 14A is a universal probe that can be used to detect a target DNA or RNA molecule, such as a p53 mRNA or DNA sequence. Although particular DNA targeting sequences are described, one skilled in the art will recognize that the targeting sequences can be altered to any sequence that will specifically bind to the target sequence of interest. In addition, other changes to the probe can be made, without significantly affecting the function of the probe. For example, the length of the molecular rod can be changed, and the exact sequence of the DNA rod can be changed.

The nanoprobe 2000 shown in FIG. 14A is similar to the nanoprobe shown in FIG. 12A. The nanoprobe 2000 includes a dsDNA rod 2002 with PEG tethers 2004, 2006 at both ends of the molecular rod 2002. As shown in FIG. 14A, the dsDNA rod 2002 can be different lengths, such as 20 nucleotides (m), 30 nucleotides (nml), or 40 nucleotides (onmlk). Attached to the PEG tethers 2004, 2006 are antisense oligonucleotides 2008, 2010. To each of the oligonucleotides 2008, 2010 an oligonucleotide 2012, 2014 complementary to at least a portion of oligonucleotides 2008, 2010 is hybridized, respectively. One of the complementary oligonucleotides 2014 includes a donor fluorophore 2016 and the other complementary oligonucleotide 2012 includes an acceptor fluorophore 2018. In a particular example, the donor fluorophore 1016 is 6-FAM and the acceptor fluorophore 2018 is Texas Red.

Oligonucleotides 2020, 2022 that contain a portion that is complementary to the core portion of the nanoprobe (for example to a portion of 2010 and 2008) and a portion that is complementary to the target sequence 2024 can be generated by an end user, and hybridized to probe 2000, thereby generating a complete probe as shown in FIG. 14A. This makes probe 2000 universal, as any target oligonucleotide sequences can be used. For example, oligonucleotide 2020 includes portion 2026 that is complementary to a portion of 2010 and portion 2028 that is complementary to a portion of target sequence 2024. Similarly, oligonucleotide 2022 includes portion 2030 that is complementary to a portion of 2008 and portion 2032 that is complementary to a portion of target sequence 2024. Therefore, to generate a nanoprobe specific for a different sequence new oligonucleotides 2020 and 2022 can be designed.

In one example, the nanoprobe shown in FIG. 14A is used to detect the target sequence (SEQ ID NO: 17, a fragment of p53) 2024 (not part of the probe). In such an example, the nanoprobe shown in FIG. 14A can be generated as follows. For example, the following molecules can be produced by Integrated DNA Technologies, Invitrogen, IBA GmbH (Germany) or Midland Certified Reagent Company, Inc., Midland, Tex.

```
                                         (SEQ ID NO: 13)
1. TAGCGAGAATTCGACGGCACAGCGTAAGGATCCGTATAGA-
[PEG18][PEG18][PEG18]-
GACGCTAGTATCTTATGAAGCTTTCCTGACTGCGGCATTA-
[PEG18][PEG18][PEG18]-
AAGGCCGGAATTCGCGAGACCGATAGGGATCCATTACTGC
(FIG. 14A, 2010, 2006, 2002, 2004, 2008).

(SEQ ID NO: 14)
2. [5' 6-FAM]-GTGCCGTCGAATTCTCGCTA
(FIG. 14A, 2014)

(SEQ ID NO: 15)
3. GCAGTAATGGATCCCTATCG-[3' Texas Red]
(FIG. 14A, 2012)

(SEQ ID NO: 16)
4. TAATGCCGCAGTCAGGAAAGCTTCATAAGATACTAGCGTC;

(SEQ ID NO: 17)
CCGCAGTCAGGAAAGCTTCATAAGATACTA;
or (SEQ ID NO: 18)
GTCAGGAAAGCTTCATAAGA.
(FIG. 14A, bottom strands for 2002)

(SEQ ID NO: 19)
5. TCTATACGGATCCTTACGCTCCATTGTTCAATATCGTCCG;

(SEQ ID NO: 20)
TCTATACGGATCCTTACGGTTCCATTGTTCAATATCGTCCG;

(SEQ ID NO: 21)
TCTATACGGATCCTTACGCTTTCCATTGTTCAATATCGTCCG
(FIG. 14A, 2020, first underlined portion is 2026
and italicized portion is 2028)

(SEQ ID NO: 22)
6. TCATCTGGACCTGGGTCTTCGTCTCGCGAATTCCGGCCTT;

(SEQ ID NO: 23)
TCATCTGGACCTGGGTCTTCTGTCTCGCGAATTCCGGCCTT;

(SEQ ID NO: 24)
TCATCTGGACCTGGGTCTTCTTGTCTCGCGAATTCCGGCCTT
(FIG. 14A, 2022, first italicized portion is 2032
and second underlined portion is 2030)
```

[PEG18] is 1 unit of Spacer 18 (Integrated DNA Technologies). Each of the molecule 4 sequences will hybridize to molecule 1, thereby producing a molecular rod of different lengths, depending which molecule 4 sequence is used. Molecules 2 and 3 will hybridize to molecule 1 due to the complementarity of the nucleic acid sequences. Molecules 5 and 6 will hybridize to molecule 1 (as well as to a target nucleic acid). The difference between the oligonucleotide sequences within the sets (molecules 5 and 6) is the sequence between the part recognizing the nanoprobe core and the part responsible for target sequence recognition.

Figure 14B:
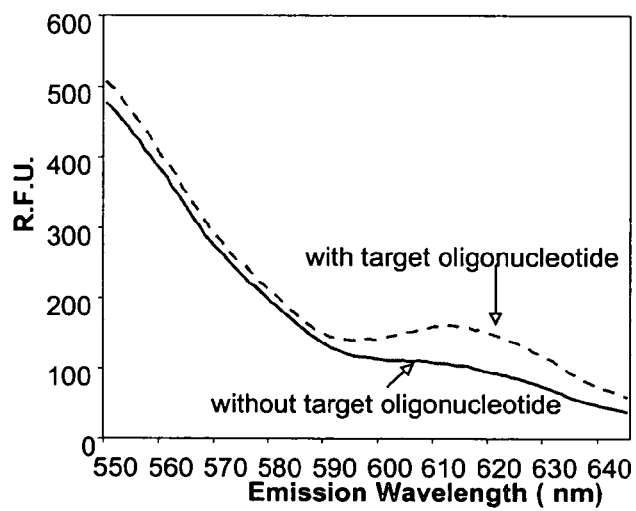
FIG. 14B is a graph showing the relative intensity of emission at different wavelengths for the two states of the universal nanoprobe of FIG. 14B in the presence or absence of the target sequence. The peak at 615nm is Texas Red emission.

All components of the nanoprobe (1 µM each) were incubated in the presence or absence of the target sequence (SEQ ID NO: 17) under conditions that permit the complementary DNA strands to hybridize, thereby generating the nanoprobe shown in FIG. 14A (one skilled in the art will appreciate that the probe can be constructed in one or more steps). The molecules were incubated overnight in buffer containing 10 mM Tris 8.0, 50 mM NaCl, and 1 mM EDTA at room temperature in a reaction volume of 20 µl. The resulting nanoprobe 2000 included p53 target-specific sequences 2028, 2032 (portions of molecules 5 and 6 above) that hybridize to the p53 target nucleic acid sequence 2024 (SEQ ID NO: 17). The donor fluorophore 2016 was 6-FAM and the acceptor fluorophore 2018 was Texas Red. Emission spectra were scanned using λex=484 nm, λCut off filter=530 nm as described in Example 6. The best ratio between the 615 nm signals of nanoprobe with and without the target sequence was observed with the combination of oligonucleotide 2020 (SEQ ID NOS: 19-21) and oligonucleotide 2022 (SEQ ID NOS: 22-24) (FIG. 14B). As shown in FIG. 14B, emission signal at 615 nm was only observed in the presence of the target sequence. It was also observed that the combination of SEQ ID NOS: 19 and 23 provided the best signal.

EXAMPLE 8

Effect of PEG Tethers

This example describes a nanoprobes with and without PEG tethers that can be used to detect a nucleic acid molecule (such as DNA or mRNA), for example in vivo, in situ, or in vitro. Although particular sequences are described, one skilled in the art will recognize that other sequences can be used to detect a target biomolecule of interest, and the sequence of such molecules can be determined by those skilled in the art.

To demonstrate the role of PEG tethers 100 nM of the nanoprobe described in Example 6 (FIG. 12A, 1000), or a tetherless nanoprobe 3000 (FIG. 15A) were incubated with and without 100 nM of the target sequence (SEQ ID NO: 12) in a buffer containing 10 mM Tris 8.0, 50 mM NaCl, 1 mM EDTA at room temperature for 2 hours and emission spectra were scanned as described in Example 6.

Figure 15A:
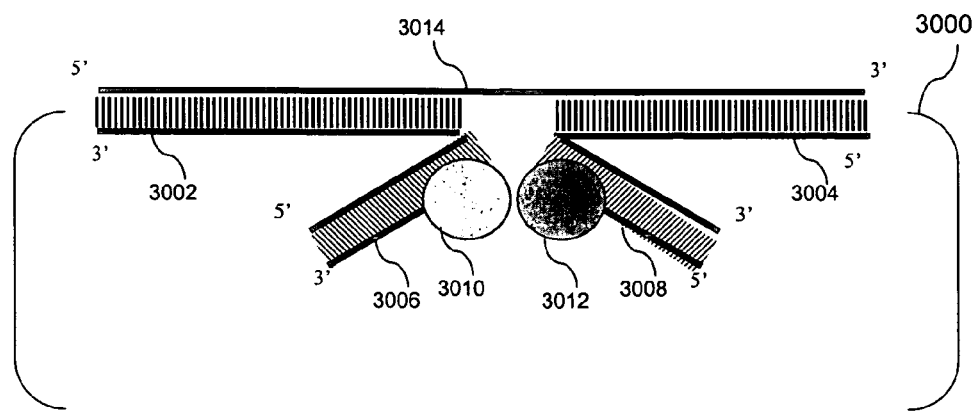
FIG. 15A is a schematic drawing showing an exemplary tetherless nanoprobe that includes antisense and fluorophore functional groups, but not tethers, which can be used to detect a target mRNA molecule.

FIG. 15A shows a tetherless nanoprobe 3000 that includes antisense oligonucleotides 3002, 3004. To each of the oligonucleotides 3002, 3004 an oligonucleotide 3006, 3008 complementary to at least a portion of oligonucleotides 3002, 3004 is hybridized, respectively. One of the complementary oligonucleotides 3006 includes a donor fluorophore 3010 and the other complementary oligonucleotide 3008 includes an acceptor fluorophore 3012. In a particular example, the donor fluorophore 3010 is 6-FAM and the acceptor fluorophore 3012 is Texas Red. In one example, the nanoprobe 3000 shown in FIG. 15A is used to detect the target sequence shown in SEQ ID NO: 12 3014 (not part of the probe). In such an example, the nanoprobe shown in FIG. 15A can be generated as follows. For example, the following molecules can be produced by Integrated DNA Technologies, Invitrogen, IBA GmbH (Germany) or Midland Certified Reagent Company, Inc. (Midland, Tex.).

```
                          (nucleotides 1-40 of SEQ ID NO: 13)
1. TAGCGAGAATTCGACGGCACAGCGTAAGGATCCGTATAGA
   (FIG. 15A, 3002).

(nucleotides 83-122 of SEQ ID NO: 13)
2. AAGGCCGGAATTCGCGAGACCGATAGGGATCCATTACTGC
   (FIG. 15A, 3004).
```

-continued
```
                                              (SEQ ID NO: 14)
3. [5' 6-FAM]-GTGCCGTCGAATTCTCGCTA
   (FIG. 15A, 3006)

(SEQ ID NO: 15)
4. GCAGTAATGGATCCCTATCG-[3' Texas Red]
   (FIG. 15A, 3008)
```

Molecules 3 and 4 will hybridize to molecules 1 and 2, respectively, due to the complementarity of the nucleic acid sequences. The four molecules are incubated under conditions that permit the complementary DNA strands to hybridize, thereby generating the tetherless nanoprobe shown in FIG. 15A. Exemplary incubation conditions include overnight incubation in THE buffer (10 mM Tris 8.0, 50 mM NaCl, 1 mM EDTA) for one hour.

Figure 15B:
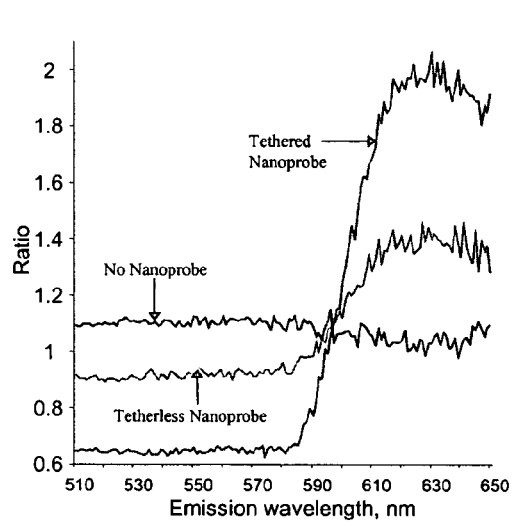
FIG. 15B is a graph showing the ratio of emission fluorescence between nanoprobes that include and omit a PEG tether and the thermodynamics of nanoprobe-target sequence complex formation.

FIG. 15B shows the ratio of fluorescence between a nanoprobe in the presence or absence of a target sequence (SEQ ID NO: 12). In the absence of a nanoprobe, the ratio is flat and close to 1.0. Tetherless nanoprobes (3000 FIG. 15A) show decreased fluorescence at 520 nm and increased FRET signal at 615 nm resulting from binding to the target sequence. However, this effect is much greater for nanoprobes containing a tether (1000 FIG. 12A). Therefore the thermodynamics of target binding by the nanoprobe is enhanced by the presence of PEG tethers.

Figure 15C:
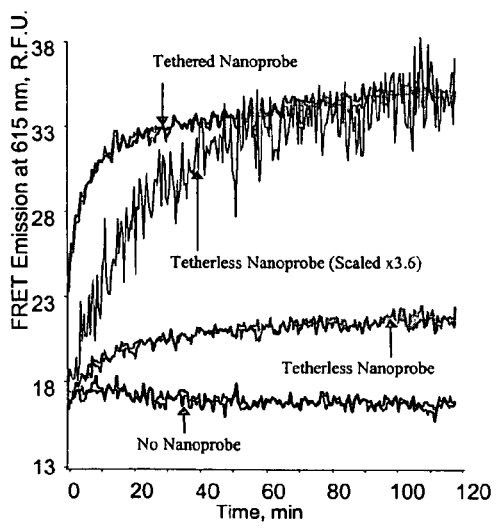
FIG. 15C is a graph comparing the kinetics of nanoprobe-target sequence complex formation between nanoprobes that include and omit a PEG tether.

The presence of tethers also enhanced the kinetics of nanoprobe-target sequence complex formation, as shown in FIG. 15C. Tethered (1000, FIG. 12A) and tetherless nanoprobes (3000, FIG. 15A) were incubated with the target sequence (SEQ ID NO: 12) as described above, and FRET signals at 615 nm detected. In the absence of a nanoprobe, the signal does not change with time. As shown in FIG. 15C, tetherless nanoprobes show slow binding kinetics, while the kinetics of tethered nanoprobe formation is faster.

EXAMPLE 9

Effect of NaCl and MgCl$_2$ of Nanoprobe-Target Sequence Complex Formation

This example describes methods used to determine the effect of NaCl and MgCl2 concentration on the formation of complexes between a nanoprobe and its target sequence.

Figure 16A:
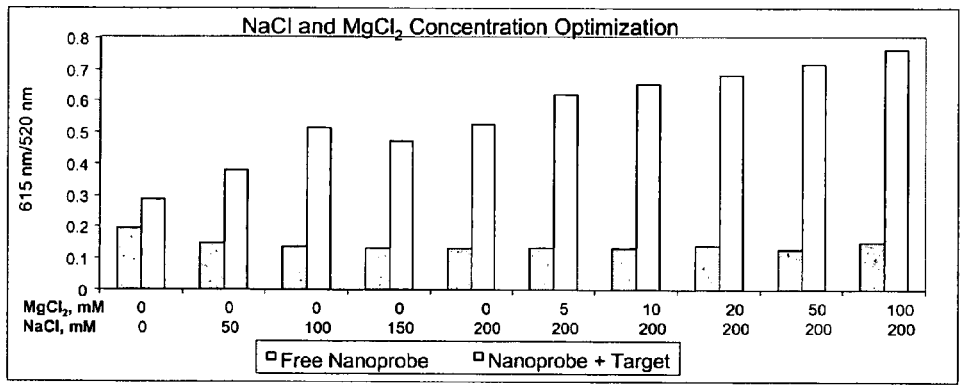
FIG. 16A is a bar graph showing the effect of NaCl and $MgCl_2$ concentration on nanoprobe-target sequence complex formation.

The nanoprobe shown in FIG. 12A (see Example 6) (100 nM) was incubated with 100 nM of a target oligonucleotide (SEQ ID NO: 12) at room temperature for 5 minutes in 50 mM Tris-HCl pH 8.0 with different concentrations of NaCl and MgCl$_2$ (see FIG. 16A). Emission spectra were obtained as described in Example 6. As shown in FIG. 16A, both NaCl and MgCl$_2$ enhance nanoprobe-target sequence complex formation.

Figure 16B:
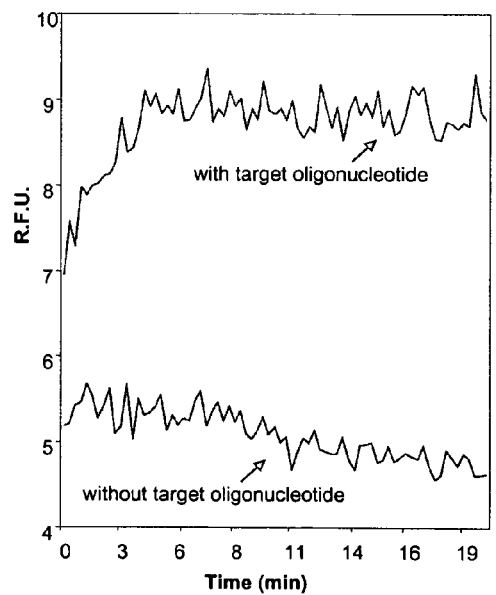
FIG. 16B is a graph showing the kinetics of nanoprobe-target sequence complex formation in the presence of 250 mM NaCl and 100 mM $MgCl_2$.

The effect of NaCl and MgCl$_2$ on kinetics was determined by incubating the nanoprobe shown in FIG. 12A (see Example 6) (50 nM) with and without 50 nM target oligonucleotide (SEQ ID NO: 12) in buffer containing 25 mM Tris-HCl pH8.0, 250 mM NaCl, 100 mM MgCl$_2$ and FRET emission at 615 nm was measured as a function of time as described in Example 6. As shown in FIG. 16B, formation of the nanoprobe-target sequence complex was completed in five minutes. In contrast, in the absence of MgCl$_2$, the formation of the nanoprobe-target sequence complex took at least 15 minutes and was not saturated by an hour (see FIG. 15C). Therefore, the presence of Mg$^{2+}$ ions enhances the kinetics of nanoprobe-target sequence complex formation, and thus Mg$^{2+}$ ions can be included in reaction buffers (for example providing MgCl$_2$ at a concentration of at least 10 mM, at least 50 mM, or at least 100 mM in the reaction buffer).

EXAMPLE 10

Nanoprobe for Detecting Ligation-Mediated mRNA-Antisense Complexes

This example describes a variant of the nanoprobe described in Example 6, that can also be used to detect target mRNA molecules, for example in vivo or in vitro. Although particular antisense sequences are described, one skilled in the art will recognize that other antisense sequences can be used to detect the RNA target biomolecule of interest, and the sequence of such antisense molecules determined by those skilled in the art. Similarly, one skilled in the art will recognize that modifications can be made to the ligase, molecular rods and tethers.

The nanoprobe 500 shown in FIG. 7 includes a DNA ligase 516. In a particular example, the nanoprobe 500 in FIG. 7 includes antisense oligonucleotides 502, 504 that can specifically hybridize to a target RNA sequence 506, which are linked via PEG tethers 508, 510 separated by a molecular rod 512. In one example, the nanoprobe shown in FIG. 7 is used to detect the target sequence 506 CGATAGGGATCCAT-TACTGCTAGCGAGAATTCGACGGCAC (SEQ ID NO: 25). In such an example, the nanoprobe shown in FIG. 7 can be generated as follows. For example, the following molecules can be produced by Integrated DNA Technologies or Midland Certified Reagent Company, Inc.

```
                                              (SEQ ID NO: 26)
1. [6-FAM]- GCAGTAATGGATCCCTATCG [PEG18][PEG18]-
TAATGCCGCAGTCAGGAAAGCTTCATAAGATACTAGCGTC (SEQ ID NO: 27)
2. GTGCCGTCGAATTCTCGCTA-[T-Texas Red]-[PEG18]
[PEG 18]-GACGCTAGTATCTTATGAA (SEQ ID NO: 28)
3. ligase-[PEG18][PEG18]-GCTTTCCTGACTGCGGCATTA
```

[PEG18] is 1 unit of Spacer 18 (Integrated DNA Technologies). When the first and second molecules are hybridized, this results in the formation of molecular rod 512, and when the first and third molecules are hybridized, this results in the formation of dsDNA molecule 514. This provides a detectable label on the nanoprobe. All of the molecules are incubated under conditions that permit the complementary DNA strands to hybridize, thereby generating the nanoprobe shown in FIG. 7. If desired, the nanoprobe can be generated in stages, by hybridizing different portions at different times. Exemplary incubation conditions include overnight incubation in THE buffer (50 mM NaCl, 10 mM Tris HCl pH=8, 1 mM EDTA) at room temperature.

When using this construct, in particular examples the incubation conditions include ATP (for a T4 ligase) or NADH (for an E. coli ligase). Manganese ions can be used to increase ligase efficiency.

EXAMPLE 11

Nanoprobe for Gene Silencing by mRNA Degradation

This example describes a nanoprobe that can be used to decrease gene expression, for example in vivo or in vitro. Such a nanoprobe can be used as an alternative to (or in addition to) antisense- or siRNA-based therapies. Although particular antisense sequences are described, one skilled in the art will recognize that other antisense sequences can be used to hybridize to the RNA target biomolecule of interest, and the sequence of such antisense molecules determined by those skilled in the art.

FIG. 9 shows a nanoprobe 600 that in particular examples includes a PEG tether 606 of 2-4 units of Spacer 18, with RNase H 604 on one end of the tether 606, and an antisense oligonucleotide 602 that can hybridize to an mRNA target 608 (not part of the nanoprobe) on the other end of the tether 606. RNase H proteins can be produced using commercially available clones (for example from the E. coli Genome Project, University of Wisconsin, Madison, Wis., such as clone pEKGb0214).

Particular examples of targets, and the corresponding antisense sequence that can be used in the nanoprobe, are listed in Table 4. For example, the antisense sequence can be attached to 2-3 units of Spacer 18, and RNase H attached to the other end of the tether, for example by using a bi-functional cross-linking reagent (see Example 1).

TABLE 4

Exemplary target sequences and the corresponding antisense sequence.

| Protein | Exemplary Target Sequence (SEQ ID NO) | Antisense sequence on nanoprobe (SEQ ID NO) |
|---|---|---|
| p53 | CGGACGATATTGAACAATGGTTC (29) | CCATTGTTCAATATCGTCCG (39) |
|  | ACTGAAGACCCAGGTCCAGATGA (30) | TCATCTGGACCTGGGTCTTC (40) |
| Hypoxia inducible factor 1 (HIF1) | TCAGCTATTTGCGTGTGAGGAAA (31) | CCTCACACGCAAATAGCTGA (41) |
|  | CTTCTGGATGCTGGTGATTTGGA (32) | TCCAAATCACCAGCATCCAG (42) |
| hexose-6-phosphate dehydrogenase (glucose 1-dehydrogenase) (H6PD) | GCCAGTACCGCCAACTGAAGACG (33) | CTTCAGTTGGCGGTACTGGC (43) |
|  | GCCGAGGACTATCAGGCCCTGAA (34) | TTCAGGGCCTGATAGTCCTC (44) |

TABLE 4-continued

Exemplary target sequences and
the corresponding antisense sequence.

| Protein | Exemplary Target Sequence (SEQ ID NO) | Antisense sequence on nanoprobe (SEQ ID NO) |
|---|---|---|
| leucine proline-enriched proteoglycan (leprecan) 1 (LEPRE1) | TGGTGATGGACGGCGTAATCTCT (35) GACCACGAGTGTCAGGAGCTGCA (36) | GATTACGCCGTCCATCACCA (45) TGCAGCTCCTGACACTCGTG (46) |
| Homo sapiens chromosome 1 open reading frame 50 (C1orf50), | TGGGCTTTGACAAACAGCTCTCA (37) CAGGACCTGGCTGTCAACCTCCT (38) | GAGCTGTTTGTCAAAGCCCA (47) AGGAGGTTGACAGCCAGGTC (48) |

EXAMPLE 12

Nanoprobe for Quantitating mRNA

This example describes a nanoprobe that can be used to quantitate specific mRNA molecules, for example in vivo or in vitro. Although particular antisense sequences are described, one skilled in the art will recognize that other antisense sequences can be used to hybridize to the RNA target biomolecule of interest, and the sequence of such antisense molecules determined by those skilled in the art.

FIG. 11 shows a nanoprobe 900 that includes donor fluorophore 902 and acceptor fluorophore 904 that permit detection (and in some examples quantitation) of RNA as it is cleaved by the RNase H 920. In a particular example, the nanoprobe 900 in FIG. 11 includes antisense oligonucleotides 906, 908 that can specifically hybridize to a target RNA sequence 910 (not part of the probe), which are linked by PEG tethers 912, 914 separated by a molecular rod 916. In one example, the nanoprobe shown in FIG. 11 is used to cleave SEQ ID NO: 25. In such an example, the nanoprobe shown in FIG. 11 can be generated as follows. For example, the following molecules can be produced by Integrated DNA Technologies or Midland Certified Reagent Company, Inc.

(SEQ ID NO: 26)
1. [6-FAM]-GCAGTAATGGATCCCTATCG[PEG18][PEG18]-TAATGCCGCAGTCAGGAAAGCTTCATAAGATACTAGCGTC (SEQ ID NO: 27)
2. GTGCCGTCGAATTCTCGCTA-[T-Texas Red]-[PEG18][PEG18]-GACGCTAGTATCTTATGAA (SEQ ID NO: 49)
3. RNaseH-[PEG18][PEG18]-GCTTTCCTGACTGCGGCATTA.

[PEG18] is 1 unit of Spacer 18 (Integrated DNA Technologies). When the first and second molecules are hybridized, this results in the formation of molecular rod 916, and when the first and third molecules are hybridized, this results in the formation of dsDNA molecule 918. This provides a detectable label on the nanoprobe. All of the molecules are incubated under conditions that permit the complementary DNA strands to hybridize, thereby generating the nanoprobe shown in FIG. 11. If desired, the nanoprobe can be generated in stages, by hybridizing different portions at different times. Exemplary incubation conditions include overnight incubation in THE buffer (50 mM NaCl, 10 mM Tris HCl pH=8, 1 mM EDTA) at room temperature.

EXAMPLE 13

Nanoprobe for Cleaving DNA-Binding Proteins

This example describes a nanoprobe that can be used to reduce the activity of a DNA-binding protein, for example in vivo or in vitro. Such a nanoprobe is an alternative to antisense- or siRNA-based therapies. Although particular DNA binding site sequences and PEG tethers are described, one skilled in the art will recognize that other sequences and tethers can be used. For example, the DNA binding site sequence can be selected based on the target DNA binding protein to be inactivated.

FIG. 10A shows a nanoprobe 700, which in particular examples includes a protein binding site sequence 702 linked to proteinase K 704 via a PEG linker 706 of 2-4 units of Spacer 18. The DNA containing a binding site 702 linked to proteinase K 704 will bind and then destroy a DNA-binding protein 708 (not part of the nanoprobe), such as a transcription factor. Although the proteinase K can cleave other proteins in the sample or the subject into which it is administered, it will attack the bound target protein at a higher rate because of the high effective concentration.

In a specific example, the nanoprobe 700 includes a DNA binding site sequence that can specifically hybridize to a DNA binding protein. Particular examples of targets, and the corresponding sequence that can be used in the nanoprobe, are listed in Table 5. For example, the nucleotide sequence can be attached to 2-3 units of Spacer 18, and a proteinase (such as proteinase K) attached to the other end of the tether (for example using a bi-functional cross-linker as described in Example 1).

TABLE 5

Exemplary target sequences and the corresponding nanoprobe sequence.

| Protein | Exemplary Target Sequence (SEQ ID NO) | | Sequence on nanoprobe (SEQ ID NO) | |
|---|---|---|---|---|
| p53 | GGACATGTCCGGACATGTCC | (50) | GGACATGTCCGGACAT | (58) |
| | GGACATGTCCGGACATGTCCGCGAAGC | (51) | GTCC | |
| Hypoxia inducible factor 1 (HIF1) | TCTCACACACGTACACACACGTGTC | (52) | GACACGTGTGTGTACG | (59) |
| | TCTCACACACGTACACACACGTGTCGCGAAGC | (53) | TGTGTGAGA | |
| NF-Kappa B consensus | GGGACATTCCGGGACATTCC | (54) | GGAATGTCCCGGAATG | (60) |
| | GGGACATTCCGGGACATTCCGCGAAGC | (55) | TCCC | |
| STAT 1 | GTCGACATTTCCCGTAAATCGTCGA | (56) | TCGACGATTTACGGGA | (61) |
| | GTCGACATTTCCCGTAAATCGTCGAGCGAAGC | (57) | AATGTCGAC | |

EXAMPLE 14

Nanoprobe for Cleaving Target Proteins

This example describes a nanoprobe that can be used to reduce the activity of a target protein, for example in vivo, in situ, or in vitro. Such a nanoprobe is an alternative to antisense- or siRNA-based therapies. Although particular protein binding agents, PEG tethers, and molecular rods are described, one skilled in the art will recognize that other binding agents, tethers, and molecular rods can be used. For example, the protein binding agent can be selected based on the target protein to be cleaved, thereby decreasing the biological activity of the target protein.

FIG. 10B shows a nanoprobe 800, which in particular examples includes proteinase K 804 linked to an antibody that recognizes an amyloidogenic or prion target protein 808 (for example an anti-Prion Protein (PrP) (Ab-3) Mouse mAb (F89/160.1.5) from EMD Biosciences, Inc.) via a PEG tethers 810, 812 each composed of 2-4 units of Spacer 18 separated by a dsDNA molecular rod 814 having the sequence shown in SEQ ID NO: 66 hybridized to its complementary strand. The nanoprobe 800 also includes a donor fluorophore 816 attached to the PEG tether 812 and an acceptor fluorophore 818 attached to PEG tether 810.

In a particular example, the nanoprobe 800 shown in FIG. 10B can include a second antibody on a tether that binds to the proteinase K, for example to reduce the function of proteinase K. However when the target protein is bound, the close proximity of the proteinase K to the target protein results in an increased activity of the proteinase K towards the target protein. For example, the following molecule can be produced by Integrated DNA Technologies or Midland Certified Reagent Company, Inc.: [PEG18][PEG18]-TAATGCCGCAGTCAG-GAAAGCTTCATAAGATACTAGCGTC [PEG18] [PEG18]-[Texas Red] (SEQ ID NO: 62)

[PEG 18] is 1 unit of Spacer 18 (Integrated DNA Technologies). The antibody 808 can be fluorescently labeled with 6-FAM using a commercial kit, and attached to the PEG using the methods described in Example 1. In addition, the proteinase K can be attached to the other end using the methods described in Example 1.

EXAMPLE 15

Nanoprobe for Sequencing Nucleic Acid Molecules

This example describes a particular probe that can be used to sequence a target nucleic acid molecule. Although particular fluorophores, molecular linkers, and polymerases are described, one skilled in the art will appreciate that variations to these can be made, based on the teachings herein.

The design is based on FIG. 8C, but the method of attachment of the molecular linker to the polymerase is changed by removing the tethers and dsDNA 582 that link the polymerizing agent 552 to the molecular linker 562. dsDNA 582 is replaced by a continuous dsDNA, without any break, that contains a binding site (ter) for the Tus protein. The Tus protein is translationally fused to HIV-1 RT.

The DNA sequences were designed using the NANEV program and checked to ensure that the restriction sites shown in FIG. 8C are unique. In addition, a MaeIII restriction site naturally appears in the ter sequence and this is unique in the probe. The Tus sequence used is the consensus bases from nine known Tus sites. Given the constraints that certain pairs of ssDNA sequences are complementary to each other and that some sequences contain the restriction sites shown in FIG. 8C, the NANEV program was used to evolve structure.

NANEV uses single letter names for dsDNA strands. Lower case letters (a, c, g, t, e, h, b, p, m) represent a segment of ssDNA that is to be hybridized to the corresponding ssDNA labeled with an upper case letter (A, C, G, T, E, H, B, P, M). Each dsDNA branch is named by the corresponding non-hydrolyzable base (A, C, G, T) while the 'hub' parts are named by restriction enzymes that cut them (E, H, B, P, M). For example, for the branch 561 that has a non-hydrolyzable adenosine 554, one oligonucleotide is named 566-561-1a, and it is bound to fluorophore 566. 566-561-1a will anneal with 563-584-561-585-554-11E-2A.

The 14 dsDNA parts designed using NANEV are shown in Table 6:

TABLE 6

Sequences to generate nanoprobe

| # | name | Sequence | SEQ ID NO: |
|---|---|---|---|
| 1 | a | GGCCTCCGTCCTCGGCAGTA | 63 |
| 2 | A | TACTGCCGAGGACGGAGGCC | 64 |
| 3 | c | CGATAATGCCTGTCATGCAT | 65 |
| 4 | C | ATGCATGACAGGCATTATCG | 66 |
| 5 | g | GAACGTCTAGACTTATCGC | 67 |

TABLE 6-continued

Sequences to generate nanoprobe

| # | name | Sequence | SEQ ID NO: |
|---|------|----------|------------|
| 6 | G | GCGATAAGTCTAGACGTTCC | 68 |
| 7 | t | CTCTCGCTCCGTGCCGTAAG | 69 |
| 8 | T | CTTACGGCACGGAGCGAGAG | 70 |
| 9 | eMh | CGCTCCTGAATTCGACGTACGC-TATATATTTA GT ATGTTGTAACTAAAGTCCAGCGCGAAGCTTA ATGACT | 71 |
| 10 | pmb | ATTCAGTCTGCAGGAAGGCCGACTTTAGTTA CAA CATACTAAATATATAGCCAGTAAGGGATCCG ATCTCG | 72 |
| 11 | E | GTACGTCGAATTCAGGAGCG | 73 |
| 12 | B | CGAGATCGGATCCCTTACTG | 74 |
| 13 | H | AGTCATTAAGCTTCGCGCTG | 75 |
| 14 | P | GGCCTTCCTGCAGACTGAAT | 76 |

Some of these 14 components are joined by PEG and linked to appropriate fluorophores to create ten oligonucleotides. The ten oligonucleotides can be synthesized commercially by IDT (Coralville, Iowa) or Midland (Midland, Tex.) as follows:

```
>566-561-1a:
                                    (SEQ ID NO: 77)
[fluorophore-566]-GGCCTCCGTCCTCGGCAGTA
where [fluorophore-566]is Rhodamine Red(TM)-X
(Absorbance Max: 574 nm, Emission Max: 594)
"GREEN"

>572-569-3c:
                                    (SEQ ID NO: 78)
CGATAATGCCTGTCATGCAT-[fluorophore-572]
where [fluorophore-572]is Cy3® (Absorbance Max:
550 nm, Emission Max: 564) "BLUE"

>570-571-5g:
                                    (SEQ ID NO: 79)
GGAACGTCTAGACTTATCGC-[fluorophore-570]
where [fluorophore-570]is Texas Red®-X
(Absorbance Max: 598 nm, Emission Max: 617)
"YELLOW"

>568-581-7t:
                                    (SEQ ID NO: 80)
[fluorophore-568]-CTCTCGCTCCGTGCCGTAAG
where [fluorophore-568]is Cy5(TM) (Absorbance
Max: 648 nm, Emission Max: 668) "RED"

>563-584-561-585-N112-11E-2A:
                                    (SEQ ID NO: 81)
GTACGTCGAATTCAGGAGCG-[PEG18]-[PEG18]-[PEG18]-
TACTGCCGAGGACGGAGGCC-[PEG9]-NH2

>NH2-583-569-567-565-4C-12B:
                                    (SEQ ID NO: 82)
NH2-[PEG9]-ATGCATGAGAGGCATTATCG-[PEG18]-[PEG18]-
[PEG18]-CGAGATCGGATCCCTTACTG

>NH2-587-571-573-575-6G-13H:
                                    (SEQ ID NO: 83)
NH2-[PEG9]-GCGATAAGTCTAGAGGTTCC-[PEG18]-[PEG18]-
[PEG18]-AGTCATTAAGCTTCGCGCTG

>577-579-581-589-NH2-14P-8T:
                                    (SEQ ID NO: 84)
GGCCTTCCTGCAGACTGAAT-[PEG18]-[PEG18]-[PEG18]-
CTTACGGCACGGAGCGAGAG-[PEG9]-NH2

>563-582-575-9eMh:
                                    (SEQ ID NO: 85)
CGCTCCTGAATTGGACGTACGCTATATATTTAGTATGTTGTAACTAAAGT
CCAGCGCGAAGCTTAATGACT

>577-582-565-10pmb:
                                    (SEQ ID NO: 86)
ATTCAGTCTGCAGGAAGGCCGACTTTAGTTACAACATACTAAATATATAG
CCAGTAAGGGATCCGATCTCG
```

Four non-hydrolyzable dNTPs are synthesized (for example by Jena Bioscience): dGMPCPP, dAMPCPP, dCMPCPP, and TMPCPP, where C represents a $CH_2$ group instead of the oxygen between the α and β phosphates. Note that the older terminology TMPCPP means dTMPCPP that is, deoxyribo-TMPCPP. Jena Bioscience can also provide dGMPNPP, dAMPNPP, dCMPNPP, and TMPNPP where N represents an NH group instead of the oxygen between the α and β phosphates. Note that the older terminology TMPNPP means dTMPNPP that is, deoxyribo-TMPNPP. In addition, Jena Bioscience provides aminoallyl-dUpCpp (NU-826) labeled with various fluorescent dyes.

Each non-hydrolyzable dNTP is covalently attached by its γ phosphate to an amino group on the corresponding oligonucleotide branch using the following reaction protocol derived from Pierce Technical Resource TR0030.1 "Modify and label oligonucleotide 5' phosphate groups" except that the roles of label and oligonucleotide are reversed.

1. Dissolve the non-hydrolyzable dNTP in 10 µl reaction buffer. (The reaction buffer recommended by Pierce is "Reaction Buffer, such as phosphate buffered saline (PBS) with EDTA: 10 mM sodium phosphate, 0.15 M NaCl, 10 mM EDTA, pH 7.2. Avoid using PBS with >10 mM phosphate, which will interfere with the intended reaction. Other amine free and carboxylate-free buffers can be substituted, but avoid Tris, which contains a primary amine that will quench the reaction.")

2. Dissolve the oligonucleotide to a final concentration of 1 mM in 10 µl of 0.1 M Imidazole, pH 6.

3. Weigh 1.25 mg (6.52 micromol) of EDC (1-ethyl-3-[3-dimethylaminopropyl]carbodiimide hydrochloride, Pierce Product No. 22980.) into a microcentrifuge tube.

4. Add 7.5 µl of the prepared non-hydrolyzable dNTP to the tube containing the EDC and immediately add 5 µl of the oligonucleotide/imidazole solution.

5. Vortex tube until contents are completely dissolved, and then briefly centrifuge the tube to gather contents.

6. Add an additional 20 µl of 0.1 M imidazole, pH 6.

7. Incubate the reaction overnight at Room Temperature.

8. Separate the unreacted oligonucleotide from the reaction product on a 10% polyacrylamide gel.

It is also possible to purify the product by its ability to bind to a DNA polymerase. The unreacted nucleotides are first removed by using a size-exclusion column or dialysis. Then a column is created that has HIV-1 RT or another polymerase attached (for example HIV-1 RT with a histidine-6 tag bound to a nickel column). A template DNA and annealed primer DNA can be added. This polymerase column should retard the oligonucleotide to which is attached a nucleotide, compared to the unreacted oligonucleotide that does not have a tethered nucleotide. A description of the carbodiimide cross-linking reaction described above is given in Chatterji and Gopal (*Methods Enzymol.* 274:456-78, 1996). This protocol is performed separately for each oligonucleotide.

The oligonucleotide: is attached to:

563-584-561-585-NH2-11E-2A (SEQ ID NO: 81) non-hydrolyzable dAMPCPP

NH2-583-569-567-330-4C-12B (SEQ ID NO: 82) non-hydrolyzable dCMPCPP

NH2-587-571-573-575-6G-13H (SEQ ID NO: 83) non-hydrolyzable dGMPCPP 577-579-581-589-NH2-14P-8T (SEQ ID NO: 84) non-hydrolyzable TMPCPP This creates the following structures:

```
>563-584-561-585-554-11E-2A:
                                     (SEQ ID NO: 87)
GTACGTCGAATTCAGGAGCG-[PEG18]-[PEG18]-[PEG18]-
TACTGCCGAGGACGGAGGCC-[PEG9]-NH2-POOH-O-POoH-CH2-
POOH-deoxyadenosine >577-579-581-589-560-14P-8T:
                                     (SEQ ID NO: 88)
GGCCTTCCTGCAGACTGAAT-[PEG18]-[PEG18]-[PEG18]-
CTTACGGCACGGAGCGAGAG-[PEG9]-NH-POOH-O-POOH-CH2-
POOH-deoxythymidine >558-587-571-573-575-6G-13H:
                                     (SEQ ID NO: 89)
deoxyguanosine-POOH-CH2-POOH-O-POOH-NH-[PEG9]-
GCGATAAGTCTAGACGTTCC-[PEG18]-[PEG18]-[PEG18]-
AGTCATTAAGCTTCGCGCTG >556-593-569-567-565-4C-12B:
                                     (SEQ ID NO: 90)
deoxycytidine-POOH-CH2-POOH-O-POOH-NH-[PEG9]-
ATGCATGACAGGCATTATCG-[PEG18]-[PEG18]-[PEG18]-
CGAGATCGGATCCCTTACTG
```

The 10 oligonucleotides: 563-584-561-585-554-11E-2A (SEQ ID NO: 87); 577-579-581-589-560-14P-8T (SEQ ID NO: 88); 558-587-571-573-575-6G-13H (SEQ ID NO: 89); 556-583-569-567-565-4C-12B (SEQ ID NO: 90); 566-561-1a (SEQ ID NO: 77); 572-569-3c (SEQ ID NO: 78); 570-571-5g (SEQ ID NO: 79); 568-581-7t (SEQ ID NO: 80); 563-582-575-9eMh (SEQ ID NO: 85); 577-582-565-10pmb (SEQ ID NO: 86); are then hybridized together to form the molecular linker 562 of the probe shown in FIG. 8C. The molecular linker 562 is then purified by gel electrophoresis, an exclusion column or sucrose gradient. The structure of the generated molecular linker 562 can be tested by digesting with the five restriction enzymes separately and in combinations and by observing the products on polyacrylamide gels.

The tus (termination utilization substance) gene from *E. coli* has been cloned in pBAD33tus (Henderson et al., *Mol. Genet. Genomics* 265:941-53, 2001, Guzman et al., *J. Bacteriol.* 77:4121-30, 1995). The HIV-1 RT p66 subunit has been cloned and modified to replace all solvent-accessible cysteine residues with serine residues (C38S and C280S) and to substitute a unique cysteine for the lysine at 287, 1(287C (Kensch et al., *J. Mol. Biol.* 301:1029-39, 2000). The unique cysteine at 287 is on the "thumb" of the polymerase, close to the active site of the polymerase, but far enough away so as not to interfere with DNA binding or the active site. There are only two cysteines in the Tus protein at CYS99 and CYS255 and they are both completely buried, (PDB 1ECR Kamada et al., *Nature* 383:598-603, 1996), so it is not necessary to engineer Tus to avoid exposed cysteines. Tus is cloned in a translational fusion with the mutated HIV-1 RT.

As seen in the three dimensional structures of HIV-1 RT (PDB entry 1RTD Huang et al., *Science* 282:1669-1675, 1998) and Tus bound to DNA (1ECR Kamada et al., *Nature* 383:598-603, 1996) the N and C termini of both proteins are on their surfaces well away from the active sites, so fusion of the two proteins will not interfere with their structures or functions. The hydrophylic polypeptide that connects the two parts of the RecB protein (PDB entry 1W36, Singleton et al., *Nature* 432:187-93, 2004) is used to connect Tus to HIV-1 RT to create Tus-HIV-1 RT.

Those skilled in the art will recognize that either Tus or HIV-1 RT protein can be placed at the N terminus of the fusion and that they can be interchanged. Those skilled in the art will also recognize that 6-histidine tags can be placed on either end of the construction to help isolation. A 6-histidine tag on the N terminus of Tus has little effect on binding, while a 6-histidine tag on the C terminus of HIV-1 has no known effect on polymerase activity.

The donor fluorophore is attached to the unique cysteine in Tus-HIV-1 RT by using the maleimide labeling reagent Fluorescein-5-Maleimide (Pierce, Rockford, Ill., using the manufacturer's instructions). This donor fluorophore forms FRET pairs with each of the four acceptor pairs described above. Those skilled in the art will also recognize that additional acceptor fluorophores can be added to the corresponding oligonucleotides to adjust for the relative signal strength, if desired. Those skilled in the art will recognize that many other possible combinations of fluorophores are possible.

The Tus-HIV-1 RT protein is added to the core to create the completed probe. The probe is then purified by gel electrophoresis, an exclusion column or sucrose gradient. The final probe structure is checked by digesting with the five restriction enzymes separately and in combinations and by observing the products on polyacrylamide gels.

In a second example, the reverse transcriptase is modified by directed mutagenesis of F227A to reduce its error frequency (Wisniewski et al., *J. Biol. Chem.* 274:28175-84, 1999). In a third example, the connection between Tus and HIV-1 RT is determined as it is for single chaing Fv (scFv) linker sequences. The classical sequence used is $(Gly_4Ser)_3$, but phage display technology can be used to obtain other variations (Tang et al., *J. Biol. Chem.* 271:15682-6, 1996; Hennecke et al., *Protein Eng.* 11:405-10, 1998).

Those skilled in the art will recognize that many other design variations are possible for the nanoprobe of the present disclosure.

EXAMPLE 16

Calculation of Distance between Fluorophores with Different Rod Lengths

As described above, the disclosed nanoprobes can include two or more functional groups connected by a tether, for example a tether composed of PEG (for example see FIGS. 2A and 3A). However, with no force to keep them separated, the free PEG chains may condense to form cloud around the same point. Therefore, as described in some of the examples above, the addition of one or more molecular rods to the nanoprobe (for example as shown in FIGS. 1B, 4A, 4B, 5A-C, 6, 7, 8B, 8C, 10B, and 11) can be included to further separate the functional groups, for example to further separate the fluorophores.

This example describes computer simulations used to determine how a FRET signal is affected by the length of a molecular rod, which can be, for example, composed of dsDNA. FIG. 1B shows the situation in the simulation. Two tethers 22, 24 are connected to a rod 26 and the distance between fluorophores 12 and 14 is measured. For a single tether, assuming that the tether is infinitely thin (does not have a problem intersecting with itself) the distance from the attachment point to the end of the tether is a random walk in three dimensions. In each single dimension this is the sum of small random steps, which would give a Gaussian distribution. In three dimensions it will be the spherically symmetric Maxwell gas distribution (Schneider, *J. Theor. Biol.*, 148:83-123, 1991). It is not appropriate to merely integrate over the intersection of two such distributions with a given separation because individual molecules will be at specific directions and distances. For this reason, an explicit simulation was performed.

To summarize the method, for each rod length, the two tethers were grown and the distance between the tips and then the FRET efficiency was computed. In the simulation, encoded by the program Bite (bi-tether), two polymers were attached to the ends of a fixed rod. Each polymer was generated by a series of random steps, starting from a rod end. The size of the steps is given by the persistence length of the chain. For PEG, the persistence length is 3.8±0.02 Å. The direction of each step was chosen randomly. The FRET signal was computed for each pair of randomly extended chains. This signal is a function the final distance between the tether chain ends R, and the FRET radius $R_0$ according to the FRET efficiency, $$E=1/(R/R_0)^6+1) \quad (1)$$

Figure 17:
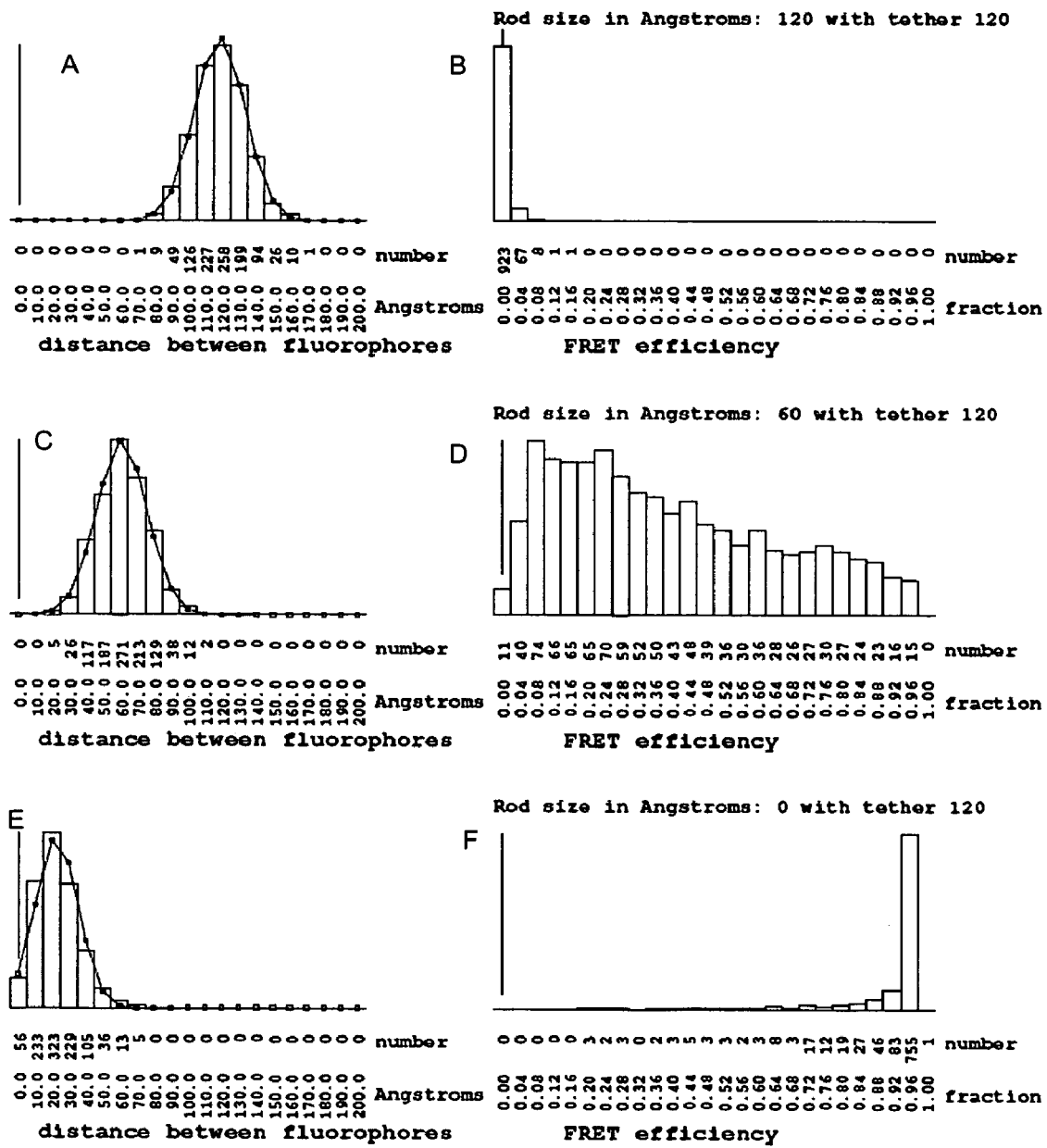
FIGS. 17A-F are graphs showing the distance between fluorophores and FRET at several molecular rod lengths. A rod has two tethers and FRET is measured between the tether tips. This is a computer simulation. The tethers are 120 Å long and consist of segments that have the persistence length of PEG (3.8 Å). (E and F) rod length 0 Å. (C and D) rod length 60 Å. (A and B) rod length 120 Å. The data were generated using the bite program and graphed using the genhis and genpic programs.

The parameters used by the program include the persistence length, the length of the tethers L and the rod length D that separates the tether points. This process was repeated 1000 times to obtain the distributions shown in FIG. 17.

When the distance, R, between the fluorophores is $R_0$, the transfer efficiency is 50%. For example, for a FRET pair with an $R_0$=60 Å, which is a typical distance, and a tether length of 120 Å, FIGS. 17A-F show the effect of varying the rod length. With a rod length of 0 (FIGS. 17E and 17F) the tethers gather around a common point (FIG. 17E) leading to a large FRET signal (FIG. 17F). As the rod length is increased to 60 Å (FIG. 17C), the FRET distribution signal spreads out (FIG. 17D). Sometimes the two ends are close and some FRET will be observed. Strikingly, when the rod length is 120 Å (FIGS. 17A and 17B), the FRET signal is almost completely eliminated (FIG. 17B). This happens when the tether length is twice the rod length, so there is plenty of potential overlap of the tethers, allowing the tethers to bind to the target. Yet the FRET signal is almost undetectable. These results demonstrate particular advantages of including a rod in a molecular linker.

EXAMPLE 17

FRET with Different Tether Lengths

This example describes methods used to determine the effect of changing the length of a tether on a FRET signal.

Figure 18:
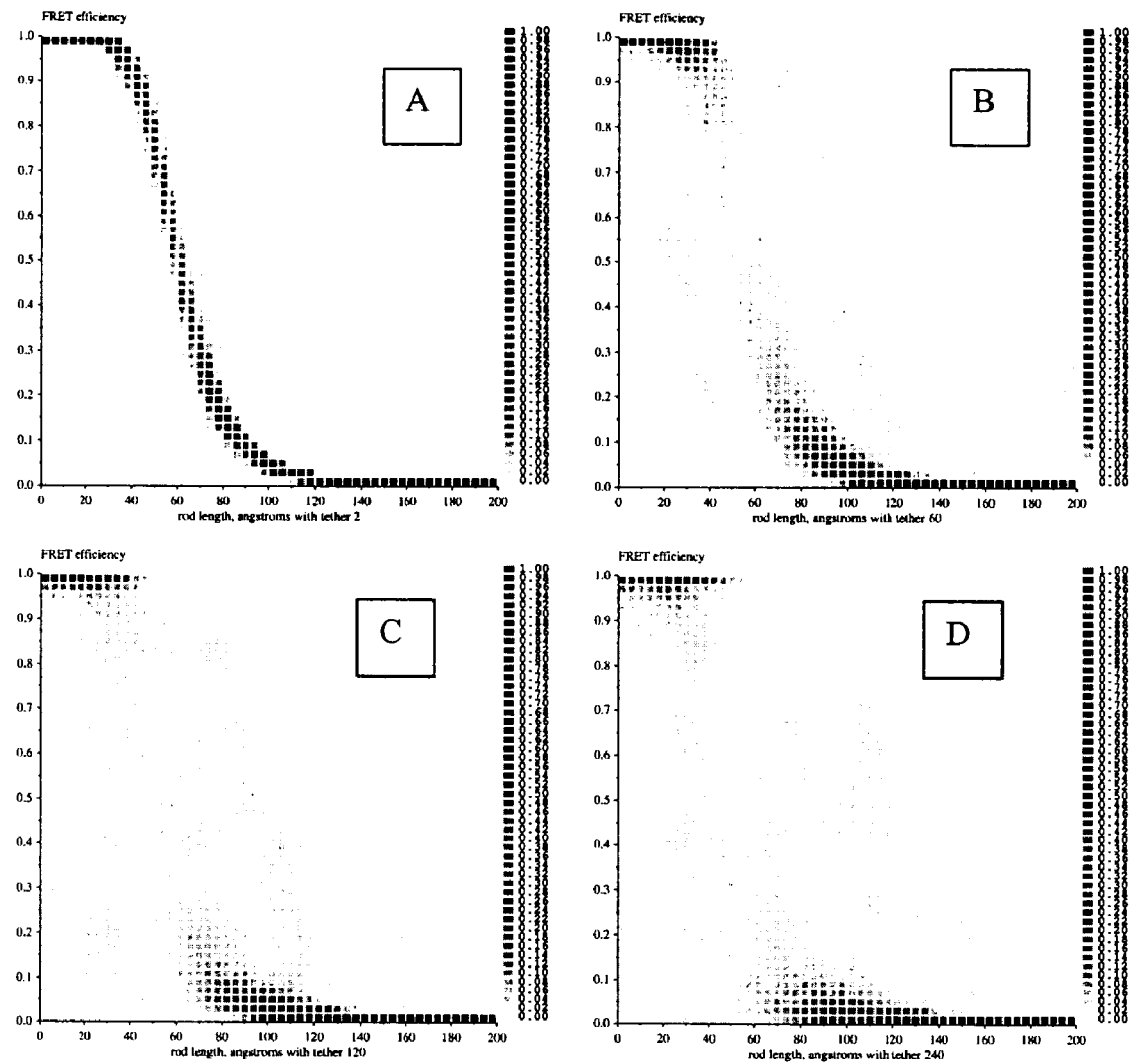
FIGS. 18A-D are graphs showing the effect of tether length on FRET at various rod lengths. The FRET distance, $R_0$, is 60 Å. Each graph shows the FRET efficiency versus the rod length. The color corresponds to the frequency that the nanoprobe gives a particular FRET signal. (A) tether length 2 Å; (B) tether length 60 Å; (C) tether length 120 Å; (D) tether length 240 Å. The data of the graphs of FIG. 17 can be obtained from the lower left part of FIG. 18 (such as FIG. 18C, with a tether length of 120 Å) by taking vertical slices at rod lengths of 0 Å, 60 Å and 120 Å. The data were generated using the bite program and graphed using programs genhis and denplo.

The Bite program was run with various tether lengths (FIG. 18). In the upper left (FIG. 18A) a very short tether of 2 Å results in the basic FRET curve given by equation (1). As the tether length is increased from 2 to 60 ∈, 120 Å and then 140 Å (FIGS. 18 B, C and D), the basic FRET curve remains, but the distribution becomes more spread out. With a molecular rod length of about 120 Å and tethers of 120 Å, there is little FRET even though the tethers could overlap significantly. Therefore, use of a molecular rod of about 120 Å and tethers of 120 Å, results in almost no FRET until the two tethers are brought together by binding to the target molecule.

Even with tethers that are 240 Å long (FIG. 18D), the right side of the distribution is almost the same as with 120 Å long tethers (FIG. 18C). That is, tether length makes little difference to the FRET results, but molecular rod length has a significant effect.

In summary, the length of the tether had little effect on FRET, while the length of the molecular rod made a significant difference. Including a rod in the molecular linker of a nanoprobe reduces FRET to almost undetectable levels, even when tethers are more than sufficiently long to reach the target. In contrast, in the presence of a target the FRET signal can be large. This provides a strong molecular switch on the output signal based on the presence or absence of the target. An example of a useful rod-tether combination for a nanoprobe uses a rod of 120 Å with two tethers also of 120 Å. These are conveniently constructed from 40 nucleotides of dsDNA, to create the rod, and 5 to 6 PEG 18 spacers of 23 Å each, to create tethers.

Two time scales can be considered in understanding the operation of molecular nanoprobes. On the time scale of molecular vibrations, picoseconds, the tethers will explore a large variety of possibilities and the joining of two tether tips that are separated by a molecular rod appears to take a long time. For example, this process could take several orders of magnitude longer than molecular vibrations, for example, 100 milliseconds. Although 100 milliseconds is a long time from the viewpoint of molecular motions, it is only ¹/₁₀th of a second on the human time scale. Thus a detection process using a molecular probe may appear to be quite rapid.

EXAMPLE 18

Targeted Nanoprobes

Nanoprobes can include molecules that can be used to direct the nanoprobe to a particular cell, or to a particular cellular compartment.

For example, commercially available fluorescent proteins that localize to actin filaments, mitochondria, endoplasmic reticulum, nuclei, Golgi apparatus, peroxisomes, and endosomes (for example from BD Biosciences—Clontech) can be used as a targeting moiety attached to a nanoprobe (see Table 7). Similarly, nanoprobes that include a targeting moiety (such as an antibody) can be used to direct a nanoprobe to a particular type of cell. Such antibodies are known in the art, and can be attached to a nanoprobe using the methods described herein.

TABLE 7

Exemplary targeting moieties from Clontech

| Product | Catalog number |
|---|---|
| pAcGFP1-Actin | 632453 |
| pAcGFP1-Endo | 632490 |
| pAcGFP1-Golgi | 632464 |
| pAcGFP1-Hyg-C1 | 632492 |
| pAcGFP1-Hyg-N1 | 632489 |
| pAcGFP1-Mem | 632491 |
| pAcGFP1-Mito | 632432 |
| pAcGFP1-Nuc | 632431 |
| pAcGFP1-Tubulin | 632488 |
| pDsRed-Monomer-Actin | 632479 |
| pDsRed-Monomer-F | 632493 |
| pDsRed-Monomer-Golgi | 632480 |
| pDsRed-Monomer-Hyg-C1 | 632495 |
| pDsRed-Monomer-Hyg-N1 | 632494 |
| pDsRed2-Mito | 632421 |
| pDsRed2-Nuc | 632408 |
| pDsRed2-Peroxi | 632418 |
| pHcRed1-Mito | 632434 |
| pHcRed1-Nuc | 632433 |

EXAMPLE 19

Reaction Rate Acceleration

In this nanomachine design, the ends of the molecular linker contain two different enzymes. There are also antibodies for a target on the ends of the molecular linker. The solution contains an initial substrate. The molecular linker can include one or more tethers separated by a molecular rod, so that when the target biomolecule is absent the reaction proceeds, but slowly. When the target biomolecule is present the reaction is accelerated. By this means alternative metabolic pathways could be selected using arbitrary external controlling substances.

EXAMPLE 20

Methods of Detecting a Biomolecule

This example describes methods that can be used to detect a biomolecule, for example in vitro, in situ, or in vivo. Although particular examples are provided for the detection of particular biomolecules (such as proteins or nucleic acid molecules), one skilled in the art will appreciate that based on the teachings herein, other biomolecules can be detected, for example by modifying the particular nanoprobes disclosed herein. In contrast to currently available assays, which can take hours to obtain a result, it should only take a few seconds to detect a signal using a nanoprobe following introduction into a cell or following contact with a sample.

In one example, the nanoprobe shown in FIG. 2A that includes the particular functional groups described in Example 1, is used to detect p53. Generally, the method includes incubating one or more nanoprobes for detecting p53 binding to DNA with a sample (for example from a subject), under conditions that permit the nanoprobe(s) to specifically bind to p53 when bound to DNA. One or more signals generated from the nanoprobe are then detected, and in some examples quantitated. For example, the presence or absence of an acceptor fluorophore emission signal can be detected.

In some examples, multiple nanoprobes are incubated with a sample. For example, if the sample is incubated with two nanoprobes having a common donor and different acceptor fluorophores, wherein one nanoprobe has an antibody that detects non-activated p53 and the other has an antibody that detects activated p53, the ratio of non-activated to activated p53 can be determined, by comparing the two FRET signals. In another example, if the sample is incubated with two nanoprobes having a common donor and different acceptor fluorophores, wherein one nanoprobe has an antibody that detects one p53 mutation and the other has an antibody that detects a different p53 mutation, the presence of a particular p53 mutation can be determined, by determining which of the two acceptor fluorophore emission signals is detected.

In a particular example, p53 binding to DNA is detected in vivo. In some examples, the nanoprobe is introduced into cells using liposomes or targeted to certain cells with immunoliposomes (for example see Yu et al., *Nucleic Acids Res.* 32:e48).

In some examples, detection of the target molecule is performed in vitro. For example, as shown in FIGS. 19A and 19B, one or more nanoprobes 4000 can be attached to a surface 4002 (such as the surface of an array, glass slide, plastic slide, or membrane). Such a surface can include controls. For example, a control nanoprobe can include an additional molecular linker with the target molecule attached on the end. Methods of attaching a probe to a surface are known. For example, as shown in FIG. 19B, DNA 4000 can be synthesized onto the surface 4002, and then two molecular linkers 4004 4006 containing fluorophores 4008 4010 are annealed. In another example, the nanoprobe 4000 includes a biotinylated oligonucleotide or a PEG tether tether terminated with a biotin, which can be attached to a surface 4002 containing streptavidin.

The biological sample can be added to the surface 4002, and an emission signal detected (for example using a photometer), wherein the presence of a signal indicates the presence or absence of the target molecule (such as p53) (depending on the type of fluorophore used). In some examples, the biological sample is applied using a capillary tube.

If desired, the biological target can be quantitated. In some examples, the nanoprobe-target complexes are allowed to form, and then the complexes detected and quantitated. In another example, the nanoprobes are monitored continuously, and the initial slope of the exponential saturation curve observed. The initial slope will depend on the concentration, independently of the total volume.

In some examples, nanoprobes are attached to the surface of an optic fiber or a flat glass or plastic (such as a slide or array) and illuminated using total internal reflection (TIR), which excites fluorophores within about 100 nm of the surface. When the biological sample is placed on the surface, the target molecules bind, leaving other components in solution. For example, red blood cells are large compared to the nanoprobes and therefore would not significantly interfere with binding because they mostly stay away from the surface (out of the excitation range of TIR). Some of the output FRET light signal will pass through the surface to a detector on the other side. In some examples, the sample is treated with a DNase to remove DNA when detecting proteins or proteinase to remove proteins when detecting nucleic acids, before application to the surface.

In some examples, the sample is concentrated. For example, a thin electrode (such as gold) can be evaporated or attached to the glass surface. A second electrode is placed elsewhere, behind the sample so that the sample is between the electrodes. Electrophoresis can then be used to drive any charged molecules, including target molecules, to the detection surface that has the immobilized nanoprobes. This allows removal of the target molecules from the biological sample to concentrate them near the nanoprobes. If target molecules contact the electrodes they may be oxidized. To reduce this possibility, the electrode surface can be coated or covered with a membrane that will not allow the DNA to reach the electrode. In some examples, the electrodes are used to extract target molecules from cells in the sample by 'reverse electroporation' of the samples. A strong but short electrical pulse will open the membranes of cell. For example, cells can be exposed to a pulse voltage of about 1-20 kV/cm for a pulse time of about 1-10 seconds. This can be followed by passive diffusion or by active transport of the molecules by electrophoresis to bring the targets to the nanoprobe detection surface.

In some examples, addition of the biological sample rehydrates a dried nanoprobe on a surface. For example, adding saliva or blood would supply moisture to the dried probes. A signal from the probe will be generated if the target is present.

EXAMPLE 21

Nanoprobe for Detecting Prostate Specific Antigen (PSA)

This example describes a nanoprobe that can be used to detect PSA.

In one example, the nanoprobe shown in FIG. 4A includes antibodies that can specifically bind to PSA as the targeting moieties 202, 204. PSA antibodies are commercially available and known in the art (such as those available from GeneTex Inc., San Antonio, Tex. and Abcam, Cambridge, Mass.). In another example matched antibody pairs are used that bind to two distinct epitopes on the target (such as those available from Anogen—YES Biotech Laboratories Ltd., Mississauga, Ontario). Such a nanoprobe can be generated using the methods disclosed herein (for example using the methods described in Example 3, except that PSA antibodies are used instead of p53 antibodies).

Generally, the method includes incubating one or more nanoprobes for detecting PSA with a sample (for example from a subject) under conditions that permit the nanoprobe(s) to specifically bind to PSA. Particular examples of samples include, but are not limited to, saliva and blood (or a fraction thereof such as serum). One or more signals generated from the nanoprobe are then detected, and in some examples quantitated. For example, the presence or absence of an acceptor fluorophore emission signal can be detected, wherein the presence of detectable signal indicates the presence of PSA.

EXAMPLE 22

Methods of Modifying a Biomolecule

This example describes methods that can be used to modify a biomolecule, for example in vitro or in vivo. Although particular examples are provided for the modification of particular biomolecules (such as proteins or nucleic acid molecules), one skilled in the art will appreciate that based on the teachings herein, other biomolecules can be modified, for example by changing the activating moiety used on the particular nanoprobes disclosed herein.

In one example, the nanoprobe shown in FIG. 9 or 11 that includes the particular functional groups described in Examples 8 and 9, is used to degrade a p53 RNA sequence, for example to decrease expression of a p53 protein. Generally, the method includes incubating one or more nanoprobes for cleaving p53 with a sample (for example from a subject), under conditions that permit the nanoprobe(s) to specifically hybridize to p53 RNA, for example under high stringency conditions. In some examples, one or more signals generated from the nanoprobe are detected, for example to quantitate an amount of p53 RNA in the sample. For example, the presence or absence of an acceptor fluorophore emission signal can be detected.

In a particular example, the p53 RNA is degraded in vivo. In some examples, the nanoprobe is introduced into cells using liposomes or targeted to certain cells with immunoliposomes (for example see Yu et al., *Nucleic Acids Res.* 32:e48).

EXAMPLE 23

Nanoprobes with Specific and Non-Specific Recognizers

This example describes nanoprobes that include a specific and a non-specific targeting moiety instead of two specific targeting moieties. Such nanoprobes can be used to detect target molecules, such as target proteins or target nucleic acid molecules (such as a target mRNA). Although particular examples are provided, those skilled in the art will recognize how to make appropriate substitutions.

Detection of a Target Protein

As shown in FIG. 20, the nanoprobe 5000 includes oligonucleotides 5002, 5004. To each of the oligonucleotides 5002, 5004 an oligonucleotide 5006, 5008 complementary to at least a portion of oligonucleotides 5002, 5004 is hybridized, respectively. One of the complementary oligonucleotides 5006 includes a donor fluorophore 5010 and the other complementary oligonucleotide 5008 includes an acceptor fluorophore 5012. In a particular example, the donor fluorophore 5010 is 6-FAM and the acceptor fluorophore 5012 is Texas Red. The nanoprobe 5000 also includes a molecular linker 5014 attached to the oligonucleotides 5002, 5004 that can be used to separate the specific targeting moiety 5030 and the non-specific targeting moiety 5026. In some examples, the molecular linker includes PEG molecules 5016, 5018 and a molecular rod 5020. The nanoprobe 5000 further includes an oligonucleotide 5022, 5024 complementary to at least a portion of oligonucleotides 5002, 5004, respectively. One of the oligonucleotides 5022 includes a non-specific targeting moiety (for example dodecyl sulfate) 5026 attached via a molecular linker 5028. Other exemplary non-specific targeting moieties 5026 that can be used include ionic and non-ionic detergents, SYPRO Ruby or SYPRO Rose dyes, and poly-arginine or poly-glutamate polypeptides. The other oligonucleotide 5024 includes a specific targeting moiety 5030 (for example an antibody).

In one example, the nanoprobe 5000 shown in FIG. 20 is used to detect a protein 5032 (not part of the probe). The hydrophobic part of dodecyl sulfate 5026 penetrates the protein core and remains inside the protein 5032. The dodecyl sulfate group 5026 and the antibody 5030 specific for the target protein 5032 bring a FRET acceptor 5012 and a donor 5010 together, resulting in a FRET signal (FIG. 20). In some examples, an aptamer is used in place of the antibody 5030.

Detection of a Target Nucleic Acid Molecule

Figures 21A, 21B:
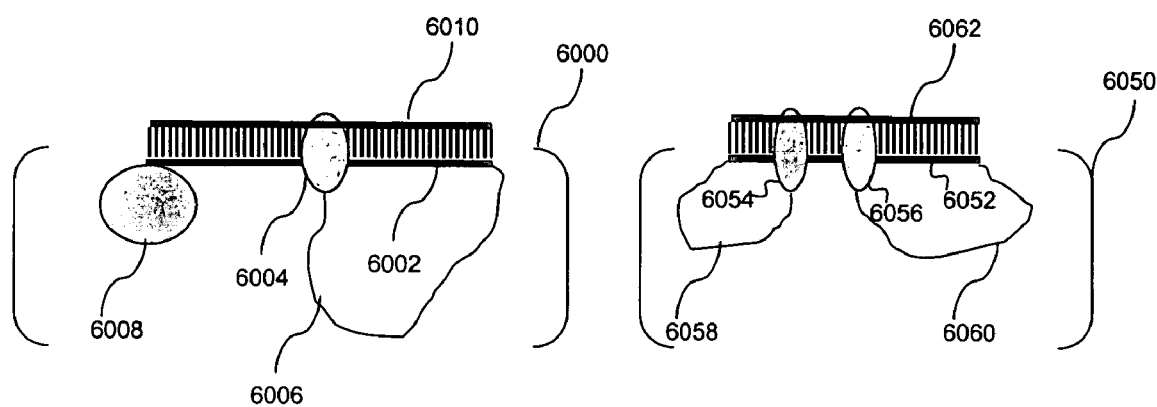
FIGS. 21A-C are a schematic drawings showing nanoprobes that include a non-specific targeting moiety (such as a intercalating fluorophore) and a specific targeting moiety (such as a complementary nucleic acid molecule) that can be used to detect a mRNA molecule.

A specific example of a nanoprobe containing specific and a non-specific recognizers that can be used to detect a target mRNA is shown in FIG. 21A. As shown in FIG. 21A, the nanoprobe 6000 contains a specific complementary oligonucleotide 6002 linked to a dsDNA intercalating fluorophore 6004 by a molecular linker 6006 (such as a PEG tether, for example a PEG tether of 5 nm to 10 nm). In some examples, the dsDNA intercalating fluorophore 6004 can act as a FRET donor, such as a FRET donor of Texas Red. A specific example of a dsDNA intercalating fluorophore 6004 that can be used is SYBR Green. The oligonucleotide 6002 also includes a fluorophore 6008, such as a FRET acceptor (for example Texas Red or TAMRA).

Binding of the oligonucleotide 6002 to its complementary target sequence 6010 (not part of the probe) results in FRET between the donor 6004 and the acceptor 6006. The fluorescence intensity of SYBR Green is enhanced over 100-fold on binding to double stranded DNA, therefore there is no background fluorescence before DNA binding.

Another specific example of a nanoprobe containing specific and non-specific recognizers that can be used to detect a target mRNA is shown in FIG. 21B. As shown in FIG. 21B, the nanoprobe 6050 contains a specific complementary oligonucleotide 6052 linked to two dsDNA intercalating fluorophores 6054 6056 (the non-specific targeting moieties) by a molecular linker 6058 6060 (such as a PEG tether, for example a PEG tether of 5 nm to 10 nm), respectively. In one example, the dsDNA intercalating fluorophores 6054 6056 are a red and a green intercalating fluorophore, such as ethidium bromide and SYBR Green. Upon binding of the nanoprobe 6050 to its target mRNA 6062 (not part of the probe), the two intercalating dyes form a FRET pair that can be detected. There is no significant donor or acceptor fluorophore background fluorescence before the specific binding.

Figure 21C:
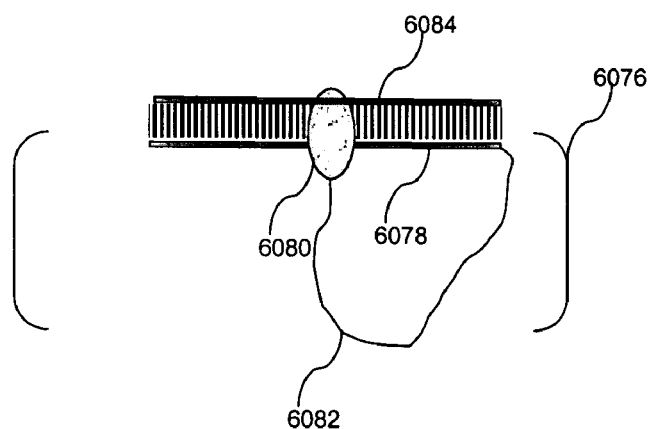

Another specific example of a nanoprobe containing specific and a non-specific recognizers that can be used to detect a target mRNA is shown in FIG. 21C. As shown in FIG. 21C, the nanoprobe 6076 contains a specific complementary oligonucleotide 6078 linked to a dsDNA intercalating fluorophore 6080 (the non-specific targeting moiety) by a molecular linker 6082 (such as a PEG tether, for example a PEG tether of 5 nm to 10 nm). Upon binding of the specific complementary oligonucleotide 6078 to the mRNA target 6084 (not part of the probe), the dsDNA intercalating fluorophore 6080 (such as SYBR Green) intercalates the complex formed between the oligonucleotide 6078 and its target 6084, thereby producing a detectable fluorescent signal.

EXAMPLE 24

Generating Nanoprobes In Vivo

This example describes methods that can be used to produce a nanoprobe in vivo. For example, the nanoprobes disclosed herein can be produced in a eukaryotic or prokaryotic host cells, such as E. coli or a yeast cell. Methods of making recombinant molecules are known in the art.

In particular examples the nanoprobes expressed in vivo include only nucleic acid and protein elements. For example, tmRNAs which attach an RNA to a protein, can be used to make an RNA nanoprobe. Nanoprobes having single chain antibodies, such as ssAB-CFP-YFP-ssAB, can be generated in vivo. In addition, such a construct can be used to detect a target protein in vivo. In one example the nanoprobe has the structure: ssAB-CFP-RecBCD tether-YFP-ssAB. The ssABs can be replaced by RNA binding proteins. The RNA can be synthesized inside the cell and would automatically bind, so nucleic acid detecting nanoprobes could also be grown.

In one example, the nanoprobe includes proteins, such as two protein-based fluorophores (such as CFP 477 nm/YFP 514 nm, EGFP 508 nm/YFP), two single chain antibodies and a tether or tethers with a separating rod or other protein. The nanoprobe could include a purification tag, such as streptavidin or a His tag, to permit purification of the probe from the cells.

EXAMPLE 25

"Self-Staining" Nanoprobes

This example describes nanoprobes that include coomassie brilliant blue as a label. Such molecules can avoid the use of a fluorometer for signal detection.

Molecules that change their absorbance spectrum after binding to another molecule and a spectrophotometer can be used for signal detection. An example of such a molecule is Coomassie protein stain. Coomassie dye (Coomassie Brilliant Blue G-250) in acid solution has an absorbance shift from 465 nm to 595 nm when it is bound to protein. This dye specifically binds to proteins at arginine, tryptophan, tyrosine, histidine and phenylalanine residues. One target for Coomassie is Poly-Arg.

Figure 22A:
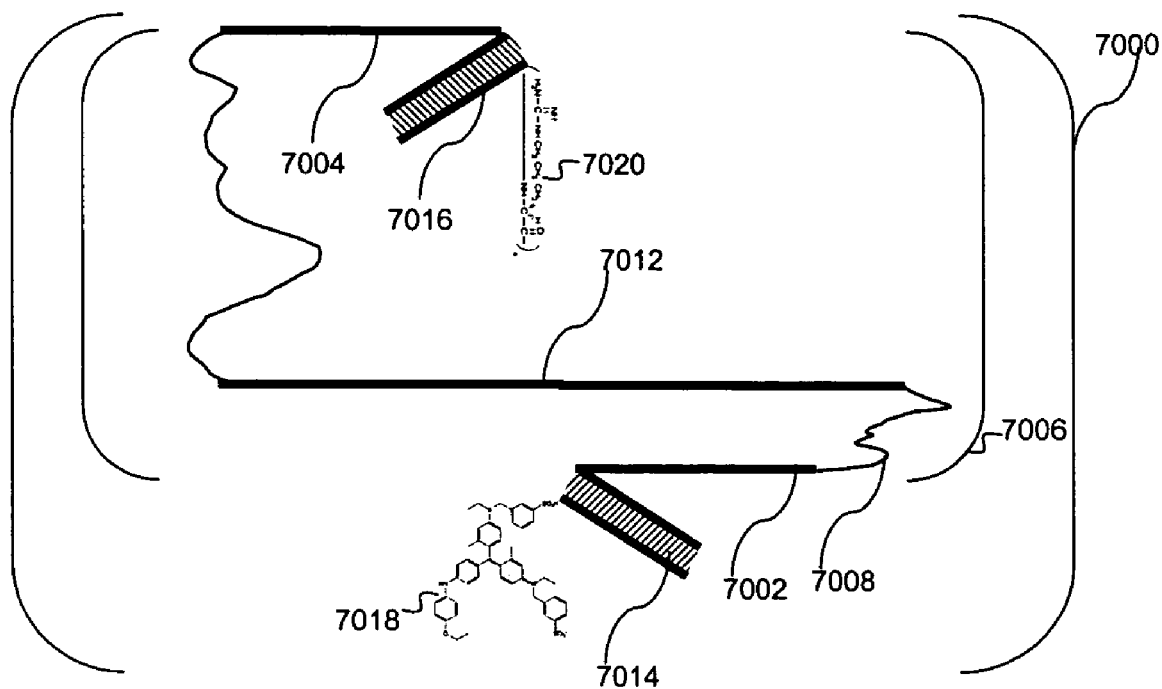
FIGS. 22A and B show an exemplary nanoprobe that uses coomassie as an alternative to a fluorophore in the (A) absence or (B) presence of the target molecule.

As shown in FIG. 22A, the nanoprobe 7000 contains specific complementary oligonucleotides 7002, 7004 attached to one another via a molecular linker 7006 that can include PEG tethers 7008, 7010 and a DNA rod 7012. To each of the oligonucleotides 7002, 7004 an oligonucleotide 7014, 7016 complementary to at least a portion of oligonucleotides 7002, 7004 is hybridized, respectively. One of the complementary oligonucleotides 7014 includes Coomassie 7018 and the other complementary oligonucleotide 7016 includes Poly-Arg 7020. The molecular linker 7006 can be used to separate the Coomassie 7018 and the Poly-Arg 7020 in the absence of the target molecule. In the absence of the target molecule, the Poly-Arg 7020 and Coomassie 7018 groups are significantly separated and no significant amount of blue color is detected (FIG. 22A).

Figure 22B:
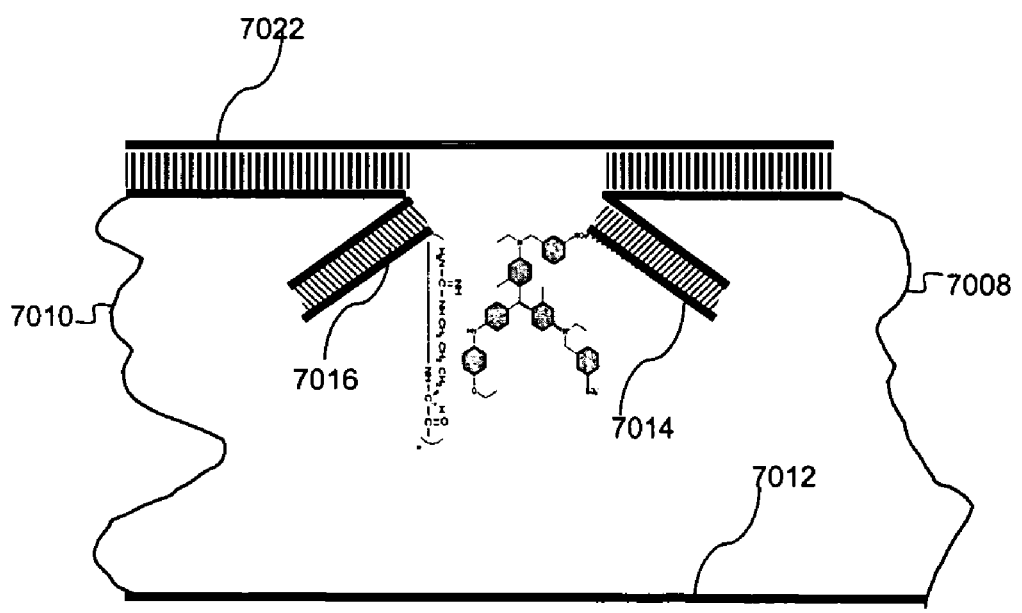

As shown in FIG. 22B, after binding to the target molecule 7022 (not part of the probe), Poly-Arg 7020 and Coomassie 7018 interact, and Coomassie 7018 changes color to blue (FIG. 22B).

The Coomassie moiety 7018 can be substituted with a pH-sensitive dye, for example phenolphthalein. Phenolphthalein is white if pH is lower than 8, and it becomes pink if pH is above 10. A Poly-Lys or any basic group can make high "local" pH. If phenolphthalein is near the basic group, it turns pink. Also, low pH-sensitive molecules, and Poly-Glu or any acidic group can be used.

In some examples, a molecular linker is included between the Coomassie moiety 7018 and oligonucleotide 7014, between the Poly-Arg 7020 and oligonucleotide 7016, or combinations thereof.

The approach described in this example can be extended to detecting target biological molecules by providing suitable adapters for connection between such biomolecules and activation compounds. For example, the dye can be used for DNA recognition if an adapter, that binds to the phosphate groups, also includes an arginine residue(s).

EXAMPLE 26

Reducing Background

This example describes methods used to reduce background signal detected from a nanoprobe in the absence of a target molecule. Although particular examples are provided for when the target is a nucleic acid molecule, such methods can be used for any target (such as a protein) (for example by attaching a quencher attached to a protein instead of a quencher-containing oligonucleotide).

In FIG. 13A, the nanoprobe bound to the target shows an increased 615 nm FRET emission and a decreased 520 nm donor emission. The fraction of the nanoprobe which is not bound to the target shows a strong 520 nm emission signal of the donor and background fluorescence of the acceptor due to the direct excitation at 470 nm. Therefore the unbound nanoprobe produced strong background signals.

Figure 23:
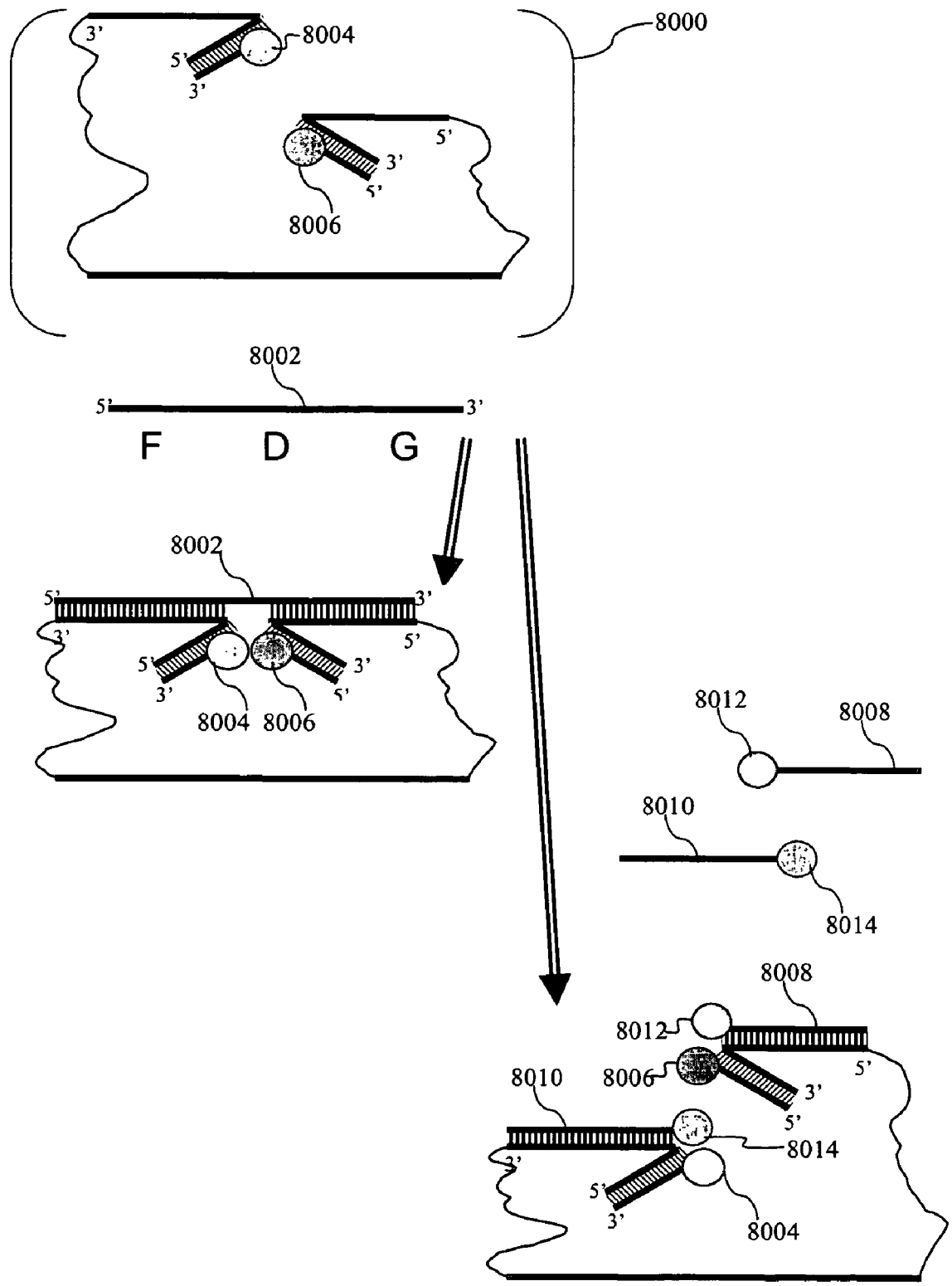
FIG. 23 is a schematic drawing showing how quencher containing-oligonucleotides can be used to decrease background fluorescence from a nanoprobe.

As shown at the top of FIG. 23, when nanoprobe 8000 is not bound it its target molecule 8002, background fluorescence can be detected from the donor 8004 and acceptor 8006 fluorophores. As shown at the bottom left of FIG. 23, when nanoprobe 8000 binds to its target 8002, FRET can be detected due to the interaction between the donor 8004 and acceptor 8006 fluorophores.

Background signals can be reduced or even eliminated by treatment of the reaction mixture after binding of the target 8002 to the nanoprobe 8000 with quencher-containing oligonucleotides 8008 8010 that are complementary to the F and G parts of the nanoprobe core. As shown at the bottom right of FIG. 23, when nanoprobe 8000 binds to the oligonucleotides 8008 8010, fluorescence of the donor 8004 and acceptor 8006 are significantly quenched by the quenchers 8012 and 8014, respectively. Integrated DNA Technologies provides quenchers that can be used on the oligonucleotides 8008 8010 (Table 8). Attaching the quencher containing oligonucleotides 8008

8010 by a tether to the nanoprobe 8000 can be used to increase the binding affinity and speed of binding.

TABLE 8

Exemplary quenchers

| Name | Extinction Coefficient | Absorbance Max | Dye to quench | Position |
|---|---|---|---|---|
| Iowa Black FQ ™ | 13344 | 531 nm | 6-FAM | 5', 3' |
| Iowa Black RQ ™ | 50457 | 656 nm | Texas Red | 5', 3' |
| Black Hole Quencher ™ 1 | 8000 | 534 nm | 6-FAM | 3' |
| Black Hole Quencher ™ 2 | 8000 | 578 nm | Texas Red | 3' |

Specific non-limiting examples of quencher-containing oligonucleotides that can be used to quench when the target sequence is SEQ ID NO: 12 are: TCTATACGGATCCT-TACGCT-[Iowa Black FQ(™)] (SEQ ID NO: 91); [Iowa BlackRQ(™)]GTCTCGCGAATTCCGGCCTT (SEQ ID NO: 92); TCTATACGGATCCTTACGCT[Black Hole Quencher™ 1] (SEQ ID NO: 93); [Black Hole Quencher™ 2]GTCTCGCGAATTCCGGCCTT (SEQ ID NO: 94); TCTATACGGATCCTTACGCT[Tamra] (SEQ ID NO: 95).

In view of the many possible embodiments to which the principles of our invention may be applied, it should be recognized that the illustrated examples are only examples of the disclosure and should not be taken as a limitation on the scope of the invention. Rather, the scope of the invention is defined by the following claims. We therefore claim as our invention all that comes within the scope and spirit of these claims.

We claim:

1. A single probe molecule for a target biomolecule, comprising:
   a molecular linker comprising a tether and a molecular rod, wherein the length of the rod is shorter than the persistence length of the rod material and the length of the tether is greater than the persistence length of the tether material;
   a first functional group at one end of the molecular linker; and
   a second functional group at the other end of the molecular linker, wherein the first and second functional groups are linked and spaced by the molecular linker, wherein the functional groups are capable of interacting with one another or with the target biomolecule in a predetermined reaction, wherein the molecular linker links the first and second functional groups sufficiently spaced from one another such that the functional groups do not substantially interact in an absence of the target biomolecule but interact in a presence of the target biomolecule to provide a signal of the presence of the biomolecule.

2. The probe of claim 1, wherein the molecular linker maintains the first and second functional groups sufficiently spaced a distance from one another to avoid substantial entanglement of the first and second functional groups in an absence of the target biomolecule.

3. The probe of claim 1, wherein at least a portion of the molecular linker is of a sufficient rigidity to reduce interaction of the first and second functional groups in the absence of the target biomolecule.

4. The probe of claim 3, wherein at least a portion of the molecular linker comprises a molecular rod having a persistence length at least as great as a persistence length of a double-stranded DNA (dsDNA) of at least 10-150 nucleotides.

5. The probe of claim 1, wherein the molecular linker is of a sufficient length to substantially avoid interaction of the first and second functional groups in the absence of the target biomolecule, and allow interaction of the first and second functional groups in the presence of the target biomolecule.

6. The probe of claim 3, wherein the molecular linker of sufficient rigidity comprises multiple molecular rods linked by tethers.

7. The probe of claim 3, wherein the molecular linker of sufficient rigidity comprises multiple tethers linked by molecular rods.

8. The probe of claim 1, wherein the tether comprises polyethylene glycol (PEG).

9. The probe of claim 8, wherein the tether consists of PEG.

10. The probe of claim 1, wherein the tether is less than 187 Å in length.

11. The probe of claim 2, wherein the molecular rod comprises a double-stranded DNA (dsDNA) molecule of at least 10 nucleotides.

12. The probe of claim 11, wherein the dsDNA molecule comprises 10-140 nucleotides.

13. The probe of claim 1, wherein the functional groups permit detection or modification of the target biomolecule.

14. The probe of claim 1, wherein the functional groups comprise a nucleic acid molecule, a protein detection agent, a protein, a label, or combinations thereof.

15. The probe of claim 14, wherein the protein detection agent comprises an antibody that specifically binds to a target protein.

16. The probe of claim 14, wherein the nucleic acid molecule comprises an antisense molecule that specifically hybridizes to a target nucleic acid sequence.

17. The probe of claim 15, wherein the first functional group comprises an antibody that can specifically bind to the target protein, and the second functional group comprises one or more DNA binding sites that can specifically bind to the target protein.

18. The probe of claim 17, wherein the target protein comprises a DNA binding protein.

19. The probe of claim 14, wherein the first and second functional groups comprise antibodies that can specifically bind to a target protein.

20. The probe of claim 16, wherein the first functional group comprises a first antisense oligonucleotide, and wherein the second functional group comprises a second antisense oligonucleotide, wherein the first and second antisense oligonucleotides can hybridize to a target nucleic acid sequence under high stringency conditions.

21. The probe of claim 14, wherein the first functional group comprises a nucleic acid sequence capable of specifically hybridizing to the target nucleic acid, thereby forming a nucleic acid complex, and wherein the second functional group comprises a protein capable of cleaving the nucleic acid complex.

22. The probe of claim 21, wherein the nucleic acid sequence comprises an antisense DNA sequence that can hybridize to a target RNA under highly stringent conditions, thereby forming a DNA/RNA nucleic acid complex and wherein the protein comprises an RNase H that can cleave RNA in the DNA/RNA nucleic acid complex.

23. The probe of claim 14, wherein the first functional group comprises one or more DNA binding sites that can specifically bind to a target protein, and wherein the second functional group comprises a protein capable of cleaving the protein.

24. The probe of claim 14, wherein the first functional group comprises a polymerase, and wherein the second functional group comprises a non-hydrolyzable dNTP.

25. The probe of claim 24, further comprising multiple functional groups linked and spaced by the molecular linker to the polymerase, wherein the multiple functional groups comprise non-hydrolyzable dNTPs.

26. The probe of claim 14, wherein the functional group comprises a label.

27. The probe of claim 26, wherein the first functional group comprises an acceptor fluorophore and the second functional group comprises a donor fluorophore.

28. A method of detecting a target biomolecule, comprising:
contacting a sample with the probe of claim 1 under conditions sufficient for the functional groups to specifically interact with the target biomolecule, wherein interaction of the functional groups results in the production of a signal by a label on the probe; and
detecting the signal when the probe interacts with target biomolecule.

29. The method of claim 28, wherein the label comprises an acceptor fluorophore and wherein when interaction of the functional groups brings the acceptor fluorophore into a proximity with a donor fluorophore to permit excitation of the acceptor fluorophore by the donor fluorophore.

30. The method of claim 29, wherein detecting a signal comprises detecting a fluorescent signal emitted from the acceptor fluorophore.

31. The method of claim 28, wherein the sample comprises a cell, and wherein contacting the sample with the probe comprises contacting the cell with the probe under conditions sufficient for the probe to enter the cell.

32. The method of claim 31, wherein the sample is obtained from a subject, and the method is performed ex vivo.

33. The method of claim 28, wherein contacting the sample with the probe comprises administration of the composition to a subject.

34. The method of claim 28, wherein the target biomolecule comprises a protein or a nucleic acid sequence.

35. The method of claim 34, wherein the protein comprises one or more mutations associated with disease.

36. A method of modifying a target biomolecule, the method comprising: exposing a sample to the probe of claim 19 under conditions sufficient for the nucleic acid sequence to bind to the target molecule and sufficient for the protein to cleave the target biomolecule.

37. The method of claim 36, further comprising detecting the cleaving of the target biomolecule.

* * * * *